(12) United States Patent
Camphausen et al.

(10) Patent No.: US 9,920,108 B2
(45) Date of Patent: Mar. 20, 2018

(54) TARGETED THERAPEUTICS BASED ON ENGINEERED PROTEINS THAT BIND EGFR

(71) Applicant: BRISTOL-MYERS SQUIBB COMPANY, Princeton, NJ (US)

(72) Inventors: Ray Camphausen, Wayland, MA (US); Brent Morse, Newton, MA (US); Stuart Emanuel, Doylestown, PA (US); David Fabrizio, South Hamilton, MA (US)

(73) Assignee: BRISTOl-MYERS SQUIBB COMPANY, Princeton, NJ (US)

( * ) Notice: Subject to any disclaimer, the term of this patent is extended or adjusted under 35 U.S.C. 154(b) by 178 days.

(21) Appl. No.: 14/954,596

(22) Filed: Nov. 30, 2015

(65) Prior Publication Data

US 2016/0152688 A1 Jun. 2, 2016

Related U.S. Application Data

(63) Continuation of application No. 13/956,952, filed on Aug. 1, 2013, now Pat. No. 9,234,028, which is a continuation of application No. 12/867,406, filed as application No. PCT/US2009/000830 on Feb. 10, 2009, now Pat. No. 8,524,244.

(60) Provisional application No. 61/065,955, filed on Feb. 14, 2008.

(51) Int. Cl.
| | |
|---|---|
| *C07K 14/78* | (2006.01) |
| *C07K 16/28* | (2006.01) |
| *C07K 14/76* | (2006.01) |
| *C07K 14/765* | (2006.01) |
| *C07K 14/79* | (2006.01) |
| *C07K 19/00* | (2006.01) |
| *A61K 38/00* | (2006.01) |

(52) U.S. Cl.
CPC ............ *C07K 14/78* (2013.01); *C07K 14/765* (2013.01); *C07K 14/79* (2013.01); *C07K 16/2863* (2013.01); *C07K 19/00* (2013.01); *A61K 38/00* (2013.01); *C07K 2317/31* (2013.01); *C07K 2318/20* (2013.01); *C07K 2319/30* (2013.01)

(58) Field of Classification Search
CPC .... A61K 39/3955; A61K 38/00; A61K 38/16; A61K 38/17; A61K 38/39; A61K 39/00; A61K 39/395; A61K 2039/505; C07K 16/468; C07K 2317/76; C07K 16/18; C07K 16/2863; C07K 16/28; C07K 16/00; C07K 14/78
See application file for complete search history.

(56) References Cited

U.S. PATENT DOCUMENTS

| | | |
|---|---|---|
| 3,773,919 A | 11/1973 | Boswell et al. |
| 4,863,457 A | 9/1989 | Lee |
| 4,997,652 A | 3/1991 | Wong |
| 5,164,188 A | 11/1992 | Wong |
| 5,235,041 A | 8/1993 | Cappello et al. |
| 5,443,505 A | 8/1995 | Wong et al. |
| 5,501,856 A | 3/1996 | Ohtori et al. |
| 5,514,581 A | 5/1996 | Ferrari et al. |
| 5,516,522 A | 5/1996 | Peyman et al. |
| 5,545,620 A | 8/1996 | Wahl et al. |
| 5,641,648 A | 6/1997 | Ferrari et al. |
| 5,766,242 A | 6/1998 | Wong et al. |
| 5,770,697 A | 6/1998 | Ferrari et al. |
| 5,792,742 A | 8/1998 | Gold et al. |
| 5,824,072 A | 10/1998 | Wong |
| 5,869,079 A | 2/1999 | Wong et al. |
| 5,922,676 A | 7/1999 | Pasqualini et al. |
| 6,018,030 A | 1/2000 | Ferrari et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,316,412 B1 | 11/2001 | Ginsberg et al. |
| 6,342,219 B1 | 1/2002 | Thorpe et al. |
| 6,348,333 B1 | 2/2002 | Niwa et al. |
| 6,369,116 B1 | 4/2002 | Wong et al. |
| 6,383,775 B1 | 5/2002 | Duff et al. |
| 6,462,189 B1 | 10/2002 | Koide |
| 6,518,018 B1 | 2/2003 | Szostak et al. |

(Continued)

FOREIGN PATENT DOCUMENTS

| | | |
|---|---|---|
| CA | 2293632 A1 | 12/1998 |
| DE | 19646372 C1 | 6/1997 |

(Continued)

OTHER PUBLICATIONS

Lipovsek, Dasa et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J.Mol. Biol., vol. 368:1024-1041 (2007).

Lipovsek, Dasa et al., "In-vitro protein evolution by ribosome display and mRNA display," Journal of Immunological Methods, vol. 290:51-67 (2004).

Litvinovich, Sergei V. et al., "Interactions Between Type III Domains in the 110 kDa Cell-binding Fragments of Fibronectin," J. Mol. Biol., vol. 248:611-626 (1995).

(Continued)

*Primary Examiner* — Bridget E Bunner

(74) *Attorney, Agent, or Firm* — Nelson Mullins Riley & Scarborough LLP; Jane E. Remillard, Esq.; Christopher L. Frank

(57) ABSTRACT

The present invention relates to single domain proteins that bind to epidermal growth factor receptor (EGFR). The invention also relates to single domain proteins for use in diagnostic, research and therapeutic applications. The invention further relates to cells comprising such proteins, polynucleotide encoding such proteins or fragments thereof, and to vectors comprising the polynucleotides encoding the innovative proteins.

14 Claims, 14 Drawing Sheets

(56) References Cited

U.S. PATENT DOCUMENTS

| | | |
|---|---|---|
| 6,524,583 B1 | 2/2003 | Thorpe et al. |
| 6,559,126 B2 | 5/2003 | Tournaire et al. |
| 6,660,492 B1 | 12/2003 | Bode et al. |
| 6,699,493 B2 | 3/2004 | Wong |
| 6,818,418 B1 | 11/2004 | Lipovsek et al. |
| 7,053,701 B2 | 5/2006 | Vice |
| 7,115,396 B2 | 10/2006 | Lipovsek et al. |
| 7,556,925 B2 | 7/2009 | Koide et al. |
| 7,598,352 B2 | 10/2009 | Koide |
| 7,847,062 B2 | 12/2010 | Chen et al. |
| 7,858,739 B2 | 12/2010 | Chen et al. |
| 7,858,759 B2 | 12/2010 | Brandt et al. |
| 8,067,201 B2 | 11/2011 | Morin et al. |
| 8,221,765 B2 | 7/2012 | Camphausen et al. |
| 8,258,265 B2 | 9/2012 | Koide |
| 8,263,741 B2 | 9/2012 | Koide |
| 8,278,419 B2 | 10/2012 | Jacobs et al. |
| 8,293,482 B2 | 10/2012 | Jacobs et al. |
| 8,324,362 B2 | 12/2012 | Chen et al. |
| 8,343,501 B2 | 1/2013 | Emanuel et al. |
| 8,470,332 B2 | 6/2013 | Camphausen et al. |
| 8,524,244 B2 | 9/2013 | Camphausen et al. |
| 8,609,613 B2 | 12/2013 | Chen et al. |
| 8,728,483 B2 | 5/2014 | Camphausen et al. |
| 9,017,655 B2 | 4/2015 | Emanuel et al. |
| 9,234,028 B2 | 1/2016 | Camphausen et al. |
| 9,328,157 B2 | 5/2016 | Chen et al. |
| 9,771,411 B2 | 9/2017 | Emanuel et al. |
| 2002/0019517 A1 | 2/2002 | Koide |
| 2002/0061307 A1 | 5/2002 | Whitlow et al. |
| 2002/0142048 A1 | 10/2002 | Sands et al. |
| 2003/0045681 A1 | 3/2003 | Neri et al. |
| 2003/0104520 A1 | 6/2003 | Ellington et al. |
| 2003/0170753 A1 | 9/2003 | Koide |
| 2003/0186385 A1 | 10/2003 | Koide |
| 2005/0244469 A1 | 11/2005 | Whitcup et al. |
| 2005/0255548 A1 | 11/2005 | Lipovsek et al. |
| 2005/0281861 A1 | 12/2005 | Hughes et al. |
| 2006/0122162 A1 | 6/2006 | Cutler |
| 2006/0182783 A1 | 8/2006 | Hughes et al. |
| 2006/0210604 A1 | 9/2006 | Dadey et al. |
| 2006/0246059 A1 | 11/2006 | Lipovsek et al. |
| 2006/0246549 A1 | 11/2006 | Kurz et al. |
| 2007/0059336 A1 | 3/2007 | Hughes et al. |
| 2007/0071575 A1 | 3/2007 | Rudduck et al. |
| 2007/0071675 A1 | 3/2007 | Wu et al. |
| 2007/0072933 A1 | 3/2007 | Peyman |
| 2007/0082365 A1 | 4/2007 | Lipovsek et al. |
| 2007/0088014 A1 | 4/2007 | Edelman et al. |
| 2007/0099879 A1 | 5/2007 | Sheibani et al. |
| 2007/0160533 A1 | 7/2007 | Chen et al. |
| 2007/0203089 A1 | 8/2007 | Rodrigues et al. |
| 2008/0015339 A1 | 1/2008 | Lipovsek et al. |
| 2008/0063651 A1 | 3/2008 | Lipovsek et al. |
| 2008/0108798 A1 | 5/2008 | Lipovsek et al. |
| 2008/0139791 A1 | 6/2008 | Lipovsek et al. |
| 2008/0193445 A1 | 8/2008 | Goetsch et al. |
| 2008/0220049 A1 | 9/2008 | Chen et al. |
| 2008/0268051 A1 | 10/2008 | Hughes et al. |
| 2009/0176654 A1 | 7/2009 | Cappuccilli et al. |
| 2009/0299040 A1 | 12/2009 | Camphausen et al. |
| 2010/0121033 A1 | 5/2010 | Camphausen et al. |
| 2010/0144599 A1 | 6/2010 | Mendlein et al. |
| 2010/0144601 A1 | 6/2010 | Jacobs et al. |
| 2010/0152063 A1 | 6/2010 | Cappuccilli et al. |
| 2010/0210511 A1 | 8/2010 | Carvajal |
| 2010/0273216 A1 | 10/2010 | Morin et al. |
| 2010/0285000 A1 | 11/2010 | Mamluk |
| 2010/0298541 A1 | 11/2010 | Wu et al. |
| 2010/0310549 A1 | 12/2010 | Chen et al. |
| 2010/0322930 A1 | 12/2010 | Kolbinger et al. |
| 2011/0021746 A1 | 1/2011 | Cappuccilli et al. |
| 2011/0034384 A1 | 2/2011 | Carvajal |
| 2011/0038866 A1 | 2/2011 | Hastewell et al. |
| 2011/0123545 A1 | 5/2011 | Marsh et al. |
| 2011/0124527 A1 | 5/2011 | Cappuccilli et al. |
| 2011/0274623 A1 | 11/2011 | Jacobs |
| 2011/0275535 A1 | 11/2011 | Loew |
| 2012/0208704 A1 | 8/2012 | Loew et al. |
| 2012/0270797 A1 | 10/2012 | Wittrup et al. |
| 2013/0012435 A1 | 1/2013 | Camphausen et al. |
| 2013/0079243 A1 | 3/2013 | Diem et al. |
| 2013/0079280 A1 | 3/2013 | Baca et al. |
| 2013/0096019 A1 | 4/2013 | Jacobs et al. |
| 2013/0096058 A1 | 4/2013 | Baca et al. |
| 2013/0310317 A1 | 11/2013 | Camphausen et al. |
| 2014/0094595 A1 | 4/2014 | Lipovsek et al. |
| 2014/0179896 A1 | 6/2014 | Chen et al. |
| 2014/0349929 A1 | 11/2014 | Camphausen et al. |
| 2015/0252097 A1 | 9/2015 | Camphausen et al. |
| 2015/0259398 A1 | 9/2015 | Emanuel et al. |
| 2016/0297869 A1 | 10/2016 | Chen et al. |
| 2017/0190761 A1 | 7/2017 | Camphausen et al. |

FOREIGN PATENT DOCUMENTS

| | | |
|---|---|---|
| EP | 0430539 A2 | 6/1991 |
| EP | 0488401 A1 | 6/1992 |
| EP | 0654256 A1 | 5/1995 |
| EP | 0962527 A1 | 12/1999 |
| EP | 0985039 B1 | 3/2000 |
| EP | 1477561 B1 | 11/2004 |
| EP | 1266025 B1 | 11/2006 |
| EP | 1137941 B1 | 8/2009 |
| EP | 2141243 A2 | 1/2010 |
| EP | 2385067 A1 | 11/2011 |
| EP | 2439212 A1 | 4/2012 |
| EP | 2379718 B1 | 3/2013 |
| JP | 4-108827 B2 | 4/1992 |
| JP | 2001-500531 A | 1/2001 |
| JP | 2007-516707 A | 6/2007 |
| WO | 92/02536 A1 | 2/1992 |
| WO | 93/03172 A1 | 2/1993 |
| WO | 95/11922 A1 | 5/1995 |
| WO | 95/13765 A1 | 5/1995 |
| WO | 96/22391 A1 | 7/1996 |
| WO | 98/12226 | 3/1998 |
| WO | 98/31700 A1 | 7/1998 |
| WO | 98/56915 A2 | 12/1998 |
| WO | 99/51773 A1 | 10/1999 |
| WO | 00/34784 | 6/2000 |
| WO | 00/034787 A1 | 6/2000 |
| WO | 0107657 A1 | 2/2001 |
| WO | 01/64942 | 9/2001 |
| WO | 02/04523 A2 | 1/2002 |
| WO | 02/32925 | 4/2002 |
| WO | 02081497 A2 | 10/2002 |
| WO | 02088171 A2 | 11/2002 |
| WO | 03022858 A2 | 3/2003 |
| WO | 03072082 A1 | 9/2003 |
| WO | 03075840 A2 | 9/2003 |
| WO | 03/104418 A2 | 12/2003 |
| WO | 2005/016970 A2 | 2/2005 |
| WO | 2005/056764 A2 | 6/2005 |
| WO | 2006/020258 A2 | 2/2006 |
| WO | 2006/091209 A2 | 8/2006 |
| WO | 2007/012614 A2 | 2/2007 |
| WO | 2007/044688 A1 | 4/2007 |
| WO | 2007/062188 A2 | 5/2007 |
| WO | 2007054120 A1 | 5/2007 |
| WO | 2007/092537 A2 | 8/2007 |
| WO | 2007/096076 A2 | 8/2007 |
| WO | 2007/121894 A2 | 11/2007 |
| WO | 2008/019290 A2 | 2/2008 |
| WO | 2008/031098 A1 | 3/2008 |
| WO | 2008/048970 A2 | 4/2008 |
| WO | 2008/066752 A2 | 6/2008 |
| WO | 2008/097497 A2 | 8/2008 |
| WO | 2008/108986 A2 | 9/2008 |
| WO | 2008/153745 A2 | 12/2008 |
| WO | 2009/023184 A2 | 2/2009 |
| WO | 2009/025806 A2 | 2/2009 |
| WO | 2009/058379 A2 | 5/2009 |
| WO | 2009/073115 A1 | 6/2009 |

(56) References Cited

FOREIGN PATENT DOCUMENTS

| | | |
|---|---|---|
| WO | 2009/083804 A2 | 7/2009 |
| WO | 2009/086116 A2 | 7/2009 |
| WO | 2009/102421 A2 | 8/2009 |
| WO | 2009/133208 A1 | 11/2009 |
| WO | 2009/142773 A2 | 11/2009 |
| WO | 2010/051274 A2 | 5/2010 |
| WO | 2010/051310 A2 | 5/2010 |
| WO | 2010/060095 A1 | 5/2010 |
| WO | 2010/069913 A1 | 6/2010 |
| WO | 2010/093627 A2 | 8/2010 |
| WO | 2010/093771 A1 | 8/2010 |
| WO | 2011/020033 A2 | 2/2011 |
| WO | 2011/035202 A2 | 3/2011 |
| WO | 2011/051333 A1 | 5/2011 |
| WO | 2011/051466 A1 | 5/2011 |
| WO | 2011/092233 A1 | 8/2011 |
| WO | 2011/100700 A2 | 8/2011 |
| WO | 2011/103105 A1 | 8/2011 |
| WO | 2011/130324 A1 | 10/2011 |
| WO | 2011/130328 A1 | 10/2011 |
| WO | 2011/130354 A1 | 10/2011 |
| WO | 2011/137319 A2 | 11/2011 |
| WO | 2011/140086 A2 | 11/2011 |
| WO | 2011/150133 A2 | 12/2011 |
| WO | 2012/016245 A2 | 2/2012 |
| WO | 2012/088006 A1 | 6/2012 |
| WO | 2012/142515 A2 | 10/2012 |
| WO | 2012/158678 A1 | 11/2012 |
| WO | 2012/158739 A1 | 11/2012 |
| WO | 2013/049275 A1 | 4/2013 |

OTHER PUBLICATIONS

Liu, Zhihong et al., "Fine mapping of the antigen-antibody interaction of scFv215, a recombinant antibody inhibiting RNA polymerase II from *Drosophila melanogaster*," Journal of Molecular Recognition, vol. 12:103-111 (1999).

Lombardo, A. et al., "Conformational flexibility and crystallization of tandemly linked type III modules of human fibronectin," Protein Science, vol. 5:1934-1938 (1996).

Lu, Dan et al., "Simultaneous Blockade of Both the Epidermal Growth Factor Receptor and the Insulin-like Growth Factor Receptor Signaling Pathways in Cancer Cells with a Fully Human Recombinant Bispecific Antibody," The Journal of Biological Chemistry, vol. 279(4):2856-2865 (2004).

Lu, Dan et al., "Tailoring in Vitro Selection for a Picomolar Affinity Human Antibody Directed against Vascular Endothelial Growth Factor Receptor 2 for Enhanced Neutralizing Activity," The Journal of Biological Chemistry, vol. 278(44):43496-43507(2003).

Lyden, David et al., "Impaired recruitment of bone-marrow-derived endothelial and hematopoietic precursor cells blocks tumor angiogenesis and growth," Nature Medicine, vol. 7(11):1194-1201 (2001).

Maeda, Hiroshi et al., "SMANCS and polymer-conjugated macromolecular drugs: advantages in cancer chemotherapy," Advanced Drug Delivery Reviews, vol. 46:169-185 (2001).

Main, Alison L. et al., "The Three-Dimensional Structure of the Tenth Type III Module of Fibronectin: An Insight into RGD-Mediated Interactions," Cell, vol. 71:671-678 (1992).

Mamluk, Rani et al., "Anti-tumor effect of CT-322 as an adnectin inhibitor of vascular endothelial growth factor receptor-2," mAbs, vol. 2(2):199-208 (2010).

Mao, Yong et al., "Fibronectin fibrillogenesis, a cell-mediated matrix assembly process," Matrix Biology, vol. 24:389-399 (2005).

Markland, William et al., "Iterative Optimization of High-Affinity Protease Inhibitors Using Phage Display. 1. Plasmin," Biochemistry, vol. 35:8045-8057 (1996).

Markland, William et al., "Iterative Optimization of High-Affinity Protease Inhibitors Using Phage Display. 2. Plasma Kallikrein and Thrombin," Biochemistry, vol. 35:8058-8067 (1996).

Maruyama, Kazuo et al., "Oligo-capping: a simple method to replace the cap structure of eukaryotic mRNAs with oligoribonucleotides," Gene, vol. 138:171-174 (1994).

Matsushima, Ayako et al., "Modification of *E. coli* Asparaginase with 2.4-Bis(O-Methoxypolyethylene Glycol)-6-Chloro-S-Triazine(Activated PEG2); Disapperance of Binding Ability Towards Anti-serum and Retention of Enzymic Activity," Chemistry Letters, pp. 773-776 (1980).

Mattheakis, Larry C. et al., "An in vitro polysome display system for identifying ligands from very large peptide libranes," Proc. Natl. Acad. Sci. USA, vol. 91:9022-9026 (1994).

McCleod, D. Scott et al., "Localization of VEGF Receptor-2 (KDR/Flk-1) and Effects of Blocking It in Oxygen-Induced Retinopathy," Investigative Ophthalmology & Visual Science, vol. 43(2):474-482 (2002).

McConnell, Stephen J. et al., "Tendamistat as a Scaffold for Conformationally Constrained Phage Peptide Libraries," J. Mol. Biol., vol. 250:460-470 (1995).

McPherson, Michael et al., "Drug Receptor Identification from Multiple Tissues Using Cellular-Derived mRNA Display Libraries," Chemistry & Biology, vol. 9:691-698 (2002).

Meinke, A. et al., "Cellulose-Binding Polypeptides from Cellulomonas fimi: Endoglucanase D (CenD), a Family A beta-1,4-Glucanase," Journal of Bacteriology, vol. 175(7):1910-1918 (1993).

Meissner, Markus et al., "Suppression of VEGFR2 Expression in Human Endothelial Cells by Dimethylfumarate Treatment: Evidence for Anti-Angiogenic Action," Journal of Investigative Dermatology, vol. 131:1356-1364 (2011).

Meyer, Rosana D. et al., "Comparative Structure-Function Analysis of VEGFR-1 and VEGFR-2, What Have We Learned from Chimeric Systems,?" Ann. N.Y. Acad. Sci., vol. 995:200-207 (2003).

Muller, Christoph W. et al., "Structure of the NF-kappaB p50 homodimer bound to DNA," Nature, vol. 373:311-317 (1995).

Muyldermans, Serge, "Single domain camel antibodies: current status," Reviews in Molecular Biotechnology, vol. 74:277-302 (2001).

Nemoto, Naoto et al., "In vitro virus: Bonding of mRNA bearing puromycin at the 3'-terminal end to the C-terminal end of its encoded protein on the ribosome in vitro," FEBS Letters, vol. 414:405-408 (1997).

Ng, Eugene W.M. et al., "Targeting angiogenesis, the underlying disorder in neovascular age-related macular degeneration," Can. J. Ophthalmol., vol. 40:352-368 (2005).

Ngo, J. Thomas et al., "Computational Complexity Protein Structure Prediction, and the Levinthal Paradox," The Protein Folding Problem and Tertiary Structure Prediction, Birkhauser, Boston, MA, K. Merz (Ed.), pp. 433-440 and 491-495 (1994).

Ngo, J. Thomas et al., "Computational Complexity, Protein Structure Prediction, and the Levinthal Paradox," The Protein Folding Problem and TErtiary Structure Prediction, Merz, K. (Ed.), Birkhauser, Boston, Chapter 14, pp. 491-495 (1994).

Niemeyer, Christof M. et al., "Oligonucleotide-directed self-assembly of proteins: semisynthetic DNA-streptavidin cybrid molecules as connectors for the generation of macroscopic arrays and the construction of supramolecular bioconjugates," NucleicAcids Research, vol. 22(25):5530-5539 (1994).

Nilsen, Timothy W., "Trans-Splicing in Protozoa and Helminths," Infections Agents and Disease, vol. 1:212-218 (1992).

Nord, Karin et al., "A combinatorial library of an alpha-helical bacterial receptor domain," Prot. Eng., vol. 8:601-608 (1995).

Nord, Karin et al., "Binding proteins selected from combinatorial libraries of an alpha-helical bacterial receptor domain," Nature Biotechnology, vol. 15:772-777 (1997).

Notice of Opposition to European Patent No. 1137941 (Application No. 99 967 261.1), 29 pages, dated May 11, 2010.

Nygren, Per-Ake et al., "Scaffolds for engineering novel binding sites in proteins," Current Opinion in Structural Biology, vol. 7:463-469 (1997).

Parker, M.H. et al., "Antibody mimics based on human fibronectin type three domain engineered for thermostability and high-affinity binding to vascular endothelial growth factor receptor two," Protein Engineering, Design & Selection, vol. 18(9):435-444 (2005).

(56) References Cited

OTHER PUBLICATIONS

Partial European Search Report for Application No. 01981621.4, 5 pages, dated Feb. 25, 2005.
Patel, Neela et al., "A Selective and Oral Small Molecule Inhibitor of Vascular Epithelial Growth Factor (VEGFR)-2 and VEGFR-1 Inhibits Neovascularization and Vascular Permeability," The Journal of Pharmacology and Experimental Therapeutics, vol. 306(3):838-845 (2003).
Phillips, Anthony J., "The challenge of gene therapy and DNA delivery," Journal of Pharmacy and Pharmacology, vol. 53:1169-1174 (2001).
Plaxco, Kevin W. et al., "A Comparison of the Folding Kinetics and Thermodynamics of Two Homologous Fibronectin Type III Modules," J. Mol. Biol., vol. 270:763-770 (1997).
Plaxco, Kevin W. et al., "Rapid refolding of a proline-rich all-beta-sheet fibronectin type III module," Proc. Natl. Acad. Sci. USA, vol. 93:10703-10706 (1996).
Posey, J. et al., "A Phase I Trial of an Anti-KDR (VEGFR2) Chimeric Antibody in Patients with Liver Metastases in Colorectal Cancer (CRC)," Slides from presentation at 2002 American Society of Clinical Oncology (ASCO) Annual Meeting, 20 pages,(2002).
Potts, Jennifer R. et al., "Fibronectin structure and assembly," Current Biology, vol. 6:648-655 (1994).
Potts, Jennifer R. et al., "Structure and Function of Fibronectin Modules," Matrix Biology, vol. 15:313-320 (1996).
Proescholdt, Martin A. et al., "Vascular Endothelial Growth Factor is Expressed in Multiple Sclerosis Plaques and Can Induce Inflammatory Lesions in Experimental Allergic Encephalomyelitis Rats," Journal of Neuropathology and Experimental Neurology,vol. 61(10):914-925 (2002).
Ramamurthy, Vidhyashankar et al., "Structures of Adnectin/Protein Complexes Reveal an Expanded Binding Footprint," Structure, vol. 20:259-269 (2012).
Richards, Julie et al., "Engineered Fibronectin Type III Domain with a RGDWXE Sequence Binds with Enhanced Affinity and Specificity to Human alphavbeta3 Integrin," J. Mol. Biol., vol. 326:1475-1488 (2003).
Roberts, Richard W. et al., "RNA-peptide fusions for the in vitro selection of peptides and proteins," Proc. Natl. Acad. Sci. USA, vol. 94:12297-12302 (1997).
Roberts, Richard W., "Totally in vitro protein selection using mRNA-protein fusions and ribosome display," Current Opinion in Chemical Biology, vol. 3:268-273 (1999).
Rottgen, Peter et al., "A human pancreatic secretory trypsin inhibitor presenting a hyperveriable highly constrained epitope via monovalent phagemid display," Gene, vol. 164:243-250 (1995).
Ackermann, Maximilian et al., "Anti-VEGFR2 and anti-IGF-1R-Adnectins inhibit Ewing's sarcoma A673-xenograft growth and normalize tumor vasculararchitecture," Angiogenesis, vol. 15:685-695 (2012).
Apte, Aaron N. et al., "Anchor-Ligated cDNA Libraries: A Technique for Generating a cDNA Library for the Immediate cloning of the 5' Ends of mRNAs," BioTechniques, vol. 15(5):890-893 (1993).
Bae, Dong-Goo et al., "Arginine-rich Anti-vascular Endothelial Growth Factor Peptides Inhibit Tumor Growth and Metastasis by Blocking Angiogenesis," The Journal of Biological Chemistry, vol. 275(18):13588-13596 (2000).
Baggio, Rick et al., "Identification of epitope-like consensus motifs using mRNA display," Journal of Molecular Recognition, vol. 15:126-134 (2002).
Baron, Martin et al.,"H NMR Assignment and Secondary Structure of the Cell Adhesion Type III Module of Fibronectin," Biochemistry, vol. 31:2068-2073 (1992).
Baron, Martin et al., "Protein modules," TIBS, vol. 16:13-17 (1991).
Batori, Vincent et al., "Exploring the potential of the monobody scaffold: effects of loop elongation on the stability of a fibronectin type III domain," Protein Engineering, vol. 15(12):1015-1020 (2002).
Bianchi, Elisabetta et al., "High Level Expression and Rational Mutagenesis of a Designed Protein, the Minibody," J. Mol. Biol., vol. 236:649-659 (1994).
Boder, Eric T. et al., "Directed evolution of antibody fragments with monovalent femtomolar antigen-binding affinity," PNAS, vol. 97(20):10701-10705 (2000).
Boder, Eric T. et al., "Yeast surface display for screening combinatorial polypeptide libraries," Nature Biotechnology, vol. 15:553-557 (1997).
Boldicke, Thomas et al., "Anti-VEGFR-2 scFvs for Cell Isolation. Single-Chain Antibodies Recognizing the Human Vascular Endothelial Growth Factor Receptor-2 (VEGFR-2/flk-1) on the Surface of Primary Endothelial Cells and Preselected CD34+ Cells fromCord Blood," Stem Cells, vol. 19:24-36 (2001).
Bork, P. et al., "The Immunoglobulin Fold, Structural Classification, Sequence Patterns and Common Core," J. Mol. Biol., vol. 242:309-320 (1994).
Bork, Peer et al., "Go hunting in sequence databases but watch out for the traps," TIG, vol. 12(10):425-427 (1996).
Bork, Peer et al., "Proposed acquisition of an animal protein domain by bacteria," Proc. Natl. Acad. Sci. USA, vol. 39:8990-8994 (1992).
Bork, Peer, "Powers and Pitfalls in Sequence Analysis: The 70% Hurdle," Genome Research, vol. 10:398-400 (2000).
Brenchley, P.E.C. et al., "Angiogenesis in inflammatory joint disease: a target for therapeutic intervention," Clin. Exp. Immunol., vol. 121:426-429 (2000).
Brenner, Steven E., "Errors in genome annotation," TIG, vol. 15(4):132-133 (1999).
Brock, Kenny V. et al., "Nucleotide sequencing of 5' and 3' termini of bovine viral diarrhea virus by RNA ligation and PCR," Journal of Virological Methods, vol. 38:39-46 (1992).
Brown, McKay et al., "Tolerance to Single, but Not Multiple, Amino Acid Replacements in Antibody VH CDR2," The Journal of Immunology, vol. 156:3285-3291 (1996).
Bruzik, James P. et al., "Spliced leader RNAs from lower eukaryotes are trans-spliced in mammalian cells," Nature, vol. 360(6405):692-695 (1992).
Caliceti, Paolo et al., "Pharmacokinetic and biodistribution properties of poly(ethylene glycol)-protein conjugates," Advanced Drug Delivery Reviews, vol. 55:1261-1277 (2003).
Campbell, Iain D. et al., "Building proteins with fibronectin type III modules, Fibronectin type III modules are versatile components of many proteins. Recent structures of module pairs show how these modules are joined together," Structure, vol. 2:333-337 (1994).
Carvalho, Jozelio Freire et al., "Vascular Endothelial Growth Factor (VEGF) in Autoimmune Diseases," Journal of Clinical Immunology, vol. 27(3):246-256 (2007).
Choy, E.H.S. et al., "Efficacy of a novel PEGylated humanized anti-TNF fragment (CDP870) in patients with rheumatoid arthritis: a phase II double-blinded, randomized, dose-escalating trial," Rheumatology, vol. 41:1133-1137 (2002).
Clackson, Tim et al., "In vitro selection from protein and peptide libraries," TibTech, vol. 12(5):173-184 (1994).
Clackson, Tim et al., "Making antibody fragments using phage display libraries," Nature, vol. 352:624-628 (1991).
Claffey, Kevin P. et al., "Vascular Endothelial Growth Factor, Regulation by Cell Differentiation and Activated Second Messenger Pathways," The Journal of Biological Chemistry, vol. 267(23):16317-16323 (1992).
Clarke, Jane et al., "Folding and Stability of a Fibronectin Type III Domain of Human Tenascin," J. Mol. Biol., vol. 270:771-778 (1997).
Connelly, Roberta J. et al., "Mitogenic properties of a bispecific single-chain Fv-Ig fusion generated from CD2-specific mAb to distinct epitopes," International Immunology, vol. 10(12):1863-1872 (1998).
Copie, Valerie et al., "Solution Structure and Dynamics of Linked Cell Attachment Modules of Mouse Fibronectin Containing the RGD and Synergy Regions: Comparison wtih the Human Fibronectin Crystal Structure," J. Mol. Biol., vol. 277:663-682 (1998).

(56) References Cited

OTHER PUBLICATIONS

Cota, Ernesto et al., "Two Proteins with the Same Structure Respond very Differently to Mutation: The Role of Plasticity in Protein Stability," J. Mol. Biol., vol. 302:713-725 (2000).
Cujec, Thomas P. et al., "Selection of v-Abl Tyrosine Kinase Substrate Sequences from Randomized Peptide and Cellular Proteomic Libraries Using mRNA Display," Chemistry & Biology, vol. 9:253-264 (2002).
Devlin, James J. et al., "Random Peptide Libraries: A Source of Specific Protein Binding Molecules," Science, vol. 249:404-406 (1990).
Dgene Search Results, 33 pages (2005).
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module of Fibronectin Obtained from a Series of Recombinant Fragments Differing in Length," J. Mol. Biol., vol. 238:123-127 (1994).
Doerks, Tobias et al., "Protein annotation: detective work for function prediction," TIG, vol. 14(6):248-250 (1998).
Duan, Jinzhu et al., "Fibronectin Type III Domain Based Monobody with High Affinity," Biochemistry, vol. 16:12656-12664(2007).
Ely, Kathryn R. et al., "Common molecular scaffold for two unrelated RGD molecules," Protein Engineering, vol. 8 (8):823-827 (1995).
Emanuel, Stuart L. et al., "A fibronectin scaffold approach to bispecific inhibitors of epidermal growth factor receptor and insulin-like growth factor-I receptor," mAbs, vol. 3(1):38-48 (2011).
Emanuel, Stuart L. et al., "Adnectins as a platform for multi-specific targeted biologics: A novel bispecific inhibitor of EGFR and IGF-IR growth factor receptors," Cancer Research, vol. 70(8 Suppl. 1), Abstract 2586, 1 page, AACR 101st AnnualMeeting (2010).
Emanuel, Stuart L. et al., "Functional activity of a bispecific Adnectin inhibitor to EGFR and IGFR," 2009 AACR Annual Meeting, Session Title: IGF-IR and PI3K Pathways, Abstract No. 2813, 2 pages (2009).
European Office Action for Application No. 06013825.2, 9 pages, dated Sep. 17, 2008.
European Office Action for Application No. 09167669.2, 7 pages, dated Dec. 28, 2009.
Fenton, Bruce et al., "Pathophysiological effects of antibodies to IGF-1R and VEGFR-2 plus fractionated radiation in DU145 prostate carcinoma xenografts," Radiation Research Society 2005 Annual Meeting, Abstract No. PP109, 1 page (2005).
Ferguson, Kimberly C. et al., "The SL1 trans-spliced leader RNA performs an essential embryonic function in Caenorhabditis elegans that can also be supplied by SL2 RNA," Genes & Development, vol. 10:1543-1556 (1996).
GenBank Accession No. AAC48614, MacLeod, J.N. et al., "Fibronectin mRNA splice variant in articular cartilage lacks bases encoding the V, III-15, and I-10 protein segments," J. Biol. Chem., vol. 271(31):18954-18960 (1996), 2 pages, (1996).
GenBank Accession No. ABB78921, Lipovek, D. et al., "New non-antibody proteins having an immunoglobulin fold, useful in research, therapeutic or diagnostic fields, particularly as scaffolds for designing proteins with specific properties, e.g. forbinding any antigen of interest," 33 pages (2005).
GenBank Accession No. CAA26536, Kornblihtt, A.R. et al., "Primary structure of human fibronectin: differential splicing may generate at least 10 polypeptides froma single gene," EMBO J., vol. 4(7):1755-1759 (1985), 7 pages, (1996).
GenBank Accession No. P07589, Skorstengaard, K. et al., "Complete primary structure of bovine plasma fibronectin," Eur. J. Biochem., vol. 161(2):441-453 (1986), 9 pages, (1997).
Rudikoff, Stuart et al., "Single amino acid substitution altering antigen-binding specificity," Proc. Natl. Acad. Sci. USA, vol. 79:1979-1983 (1982).
Schildbach, Joel F. et al., "Contribution of a single heavy chain residue to specificity of an anti-digoxin monoclonal antibody," Protein Science, vol. 3:737-749 (1994).
Schildbach, Joel F. et al., "Heavy Chain Position 50 is a Determination of Affinity and Specificity for the Anti-digoxin Antibody 26-10," The Journal of Biological Chemistry, vol. 268(29):21739-21747 (1993).
Scott, Jamie K. et al., "Searching for Peptide Ligands with an Epitope Library," Science, vol. 249:386-390 (1990).
Shibata, K. et al., "An attempt to substitute the cell binding domain of human fibronectin in lambda phage J protein: Computer design and expression," Biochimie, vol. 75:459-465 (1993).
Shibuya, Masabumi, "Vascular endothelial growth factor receptor-2: Its unique signaling and specific ligand, VEGF-E," Cancer Sci., vol. 94(9):751-756 (2003).
Shima, David T. et al., "The Mouse Gene for Vascular Endothelial Growth Factor," The Journal of Biological Chemistry, vol. 271(7):3877-3883 (1996).
Skolnick, Jeffrey et al., "From genes to protein structure and function: novel applications of computational approaches in the genomic era," TIBTECH, vol. 18:34-39 (2000).
Smith, George P. et al., "Phage Display," Chem. Rev., vol. 97:391-410 (1997).
Smith, Temple F. et al., "The challenges of genome sequence annotation or 'The devil is in the details,'" Nature Biotechnology, vol. 15:1222-1223 (1997).
Supplementary European Search Report for Application No. 01913159.8, 3 pages, dated Dec. 21, 2004.
Supplementary European Search Report for Application No. 99967261.1, 3 pages, dated Mar. 6, 2002.
Takahashi, Satoru, "Vascular Endothelial Growth Factor (VEGF), VEGF Receptors and Their Inhibitors for Antiangiogenic Tumor Therapy," Biol. Pharm. Bull. vol. 34(12):1785-1788 (2011).
Tang, Lisa et al., "Pharmacokinetic Aspects of Biotechnology Products," Journal of Pharmaceutical Sciences, vol. 93(9):2184-2204 (2004).
Tischer, Edmund et al., "The Human Gene for Vascular Endothelial Growth Factor," The Journal of Biological Chemistry, vol. 266(18):11947-11954 (1991).
Tokuriki, Nobuhiko et al., "Stability effects of mutations and protein evolvability," Current Opinion in Structural Biology, vol. 19:596-604 (2009).
Tramontano, Anna et al., "The Making of the Minibody: an Engineered beta-Protein for the Display of Conformationally Constrained Peptides," Journal of Molecular Recognition, vol. 7:9-24 (1994).
Trinh, Ryan et al., "Optimization of codon pair use within the (GGGGS)3 linker sequence results in enhanced protein expression," Molecular Immunology, vol. 40:717-722 (2004).
Verheul, H.M.W. et al., "Targeting Vascular Endothelial Growth Factor Blockade: Ascites and Pleural Effusion Formation," The Oncologist, vol. 5(Suppl. 1):45-50 (2000).
Vuento, Matti et al., "Purification of Fibronectin from Human Plasma by Affinity Chromatography under Non-Denaturing Conditions," Biochem. J., vol. 183:331-337 (1979).
Wang, Cheng-I et al., "Isolation of a High Affinity Inhibitor of Urokinase-type Plasminogen Activator by Phage Display of Ecotin," The Journal of Biological Chemistry, vol. 270(20):12250-12256 (1995).
Watanabe, H. et al., "Anti-vascular endothelial growth factor receptor-2 (Flk-1/KDR) antibody suppresses contact hypersensitivity," Experimental Dermatology, vol. 13:671-681 (2004).
Watanabe, Takeshi et al., "Gene Cloning of Chitinase A1 from Bacillus circulans WL-12 Revealed Its Evolutionary Relationship to Serratia Chitinase and to the Type III Homology Units of Fibronectin," The Journal of Biological Chemistry, vol. 265:15659-15665 (1990).
Wells, James A., "Additivity of Mutational Effects in Proteins," Biochemistry, vol. 29(37):8509-8517 (1990).
Williams, Alan F. et al., "The Immunoglobulin Superfamily—Domains for Cell Surface Recognition," Ann. Rev. Immunol., vol. 6:381-405 (1988).
Williams, Michael J. et al., "Solution Structures of Modular Proteins by Nuclear Magnetic Resonance," Methods in Enzymology, vol. 245:451-469 (1994).

(56) References Cited

OTHER PUBLICATIONS

Wilson, David S. et al., "The use of mRNA display to select high-affinity protein-binding peptides," PNAS, vol. 98(7):3750-3755 (2001).
Written Opinion for Application No. PCT/US01/06414, 5 pages, dated Feb. 7, 2002.
Xiang, Jim et al., "Study of B72.3 combining sites by molecular modeling and site-directed mutagenesis," Protein Engineering, vol. 13(5):339-344 (2000).
Xu, Lihui et al., "Directed Evolution of High-Affinity Antibody Mimics Using mRNA Display," Chemistry & Biology, vol. 9:933-942 (2002).
Yang, Karen et al., "Tailoring structure-function and pharmacokinetic properties of single-chain Fv proteins by site-specific PEGylation," Protein Engineering, vol. 16(10):761-770 (2003).
Yoshiji, H. et al., "Vascular endothelial growth factor and receptor interaction is a prerequisite for murine hepatic Fibrogenesis," Gut, vol. 52:1347-1354 (2003).
Zdanov, Alexander et al., Structure of a single-chain antibody variable domain (Fv) fragment complexed with a carbohydrate antigen at 1.7-A resolution, Proc. Natl. Acad. Sci. USA, vol. 91:6423-6427 (1994).
Zhou, Tianhong et al., "Development of a multi-drug delivery implant for intraocular management of proliferative vitreoretinopathy," Journal of Controlled Release, vol. 55:281-295 (1998).
Zhu, Z. et al., "Inhibition of human leukemia in an animal model with human antibodies directed against vascular endothelial growth factor receptor 2. Correlation between antibody affinity and biological activity," Leukemia, vol. 17:604-611 (2003).
GenBank Accession No. X02761, Kornblihtt, A.R. et al., "Primary structure of human fibronectin: differential splicing may generate at least 10 polypeptides from a single gene," EMBO J., vol. 4(7):1755-1759 (1985), 4 pages, (1996).
Ghosh, Gourisankar et al., "Structure of NF-kappaB p50 homodimer bound to a kappaB site," Nature, vol. 373:303-310 (1995).
Gill, Davinder S. et al., "Biopharmaceutical drug discovery using novel protein scaffolds," Current Opinion in Biotechnology, vol. 17:653-658 (2006).
Giusti, Angela M. et al., "Somatic diversification of S107 from an antiphosphocholine to an anti-DNA autoantibody is due to a single base change in its heavy chain variable region," Proc. Natl. Acad. Sci. USA, vol. 84:2926-2930 (1987).
Goedert, M. et al., "Cloning and sequencing of the cDNA encoding an isoform of microtubule-associated protein tau containing four tandem repeats: differential expression of tau protein mRNAs in human brain," The EMBO Journal, vol. 8(2):393-399(1989).
Grant, Richard P. et al., "Structural Requirements for Biological Activity of the Ninth and Tenth FIII Domains of Human Fibronectin," The Journal of Biological Chemistry, vol. 272(10):6159-6166 (1997).
Hamers-Casterman, C. et al., "Naturally occurring antibodies devoid of light chains," Nature, vol. 363:446-448 (1993).
Hammond, Philip W. et al., "In Vitro Selection and Characterization of Bcl-XL-binding Proteins from a Mix of Tissue-specific mRNA Display Libraries," The Journal of Biological Chemistry, vol. 276(24):20898-20906 (2001).
Harpaz, Yahouda et al., "Many of the IMmunoglobulin Superfamily Domains in Cell Adhesion Molecules and Surface Receptors Belong to a New Structural Set Which is Close to That Containing Variable Domains," J. Mol. Biol., vol. 238:528-539 (1994).
Hey, Thomas et al., "Artificial, non-antibody binding proteins for pharmaceutical and industrial applications," Trends in Biotechnology, vol. 23(10):514-522 (2005).
Hocking, Denise C. et al., "A Novel Role for the Integrin-binding III-10 Module in Fibronectin Matrix Assembly," The Journal of Cell Biology, vol. 133(2):431-444 (1996).
Hocking, Denise C. et al., "Activation of Distinct alpha5beta1-mediated Signaling Pathways by Fibronectin's Cell Adhesion and Matrix Assembly Domains," The Journal of Cell Biology, vol. 141(1):241-253 (1998).
Huang, Fei et al., "The Mechanisms of Differential Sensitivity to an Insulin-like Growth FActor-1 Receptor Inhibitor (BMS-536924) and Rationale for Combining with EGFR/HER2 Inhibitors," Cancer Res., vol. 69(1):161-170 (2009).
Huang, Hu et al., "Blockade of VEGFR1 and 2 Suppresses Pathological Angiogenesis and Vascular Leakage in the Eye," PLoS One, vol. 6(6):e21411, 14 pages, doi:10.1371/journal.pone.0021411 (2011).
Husimi, Y. et al., "Role of the Virus-type Strategy in Encoded Molecular Evolution," Progress in Biophysics and Molecular Biology, vol. 65(Suppl. 1):64 (1996).
Hynes, Richard O. et al., "Integrins: Versability, Modulation, and Signaling in Cell Adhesion," Cell, vol. 69:11-25 (1992).
International Preliminary Examination Report for Application No. PCT/US01/06414, 6 pages, dated Aug. 27, 2002.
International Preliminary Examination Report for Application No. PCT/US01/32233, 5 pages, dated Dec. 10, 2003.
International Preliminary Examination Report for Application No. PCT/US99/29317, 4 pages, dated Aug. 14, 2000.
International Preliminary Report on Patentability and Written Opinion for Application No. PCT/US2009/003192, 12 pages, dated Nov. 23, 2010.
International Preliminary Report on Patentability and Written Opinion for Application No. PCT/US2009/065765, 12 pages, dated May 24, 2011.
International Preliminary Report on Patentability and Written Opinion for Application No. PCT/US2011/034998, 10 pages, dated Nov. 6, 2012.
International Preliminary Report on Patentability for Applicaiton No. PCT/US2004/040885, 6 pages, dated Jun. 7, 2006.
International Preliminary Report on Patentability for Application No. PCT/US2011/038013, 9 pages, dated Nov. 27, 2012.
International Search Report for Application No. PCT/US01/06414, 5 pages, dated Aug. 7, 2001.
International Search Report for Application No. PCT/US01/32233, 3 pages, dated Jun. 12, 2003.
International Search Report for Application No. PCT/US04/40885, 3 pages, dated Feb. 21, 2006.
International Search Report for Application No. PCT/US2009/003192, 8 pages, dated Jun. 1, 2010.
International Search Report for Application No. PCT/US2009/065765, 7 pages, dated Apr. 23, 2010.
International Search Report for Application No. PCT/US2011/034998, 5 pages, dated Jul. 17, 2012.
International Search Report for Application No. PCT/US2011/038013, 7 pages, dated Jan. 25, 2012.
International Search Report for Application No. PCT/US99/29317, 2 pages, dated Apr. 6, 2000.
Jain, Rakesh K. et al., "Dissecting Tumour Pathophysiology Using Intravital Microscopy," Nature, vol. 2:266-276 (2002).
Jakob, W. et al., "The chick embryo chorioallantoic membrane as a bioassay for angiogenesis factors: Reactions induced by carrier materials," Exp. Path. Bd., vol. 15:241-249 (1978).
Jung, Gyoo Yeol et al., "A Functional Protein Chip for Pathway Optimization and in Vitro Metabolic Engineering," Science, vol. 304:428-431 (2004).
Keefe, Anthony D. et al., "Functional proteins from a random-sequence library," Nature, vol. 410:715-718 (2001).
King, Catherine A. et al., "DNA vaccines with single-chain Fv fused to fragment C of tetanus toxin induce protective immunity against lymphoma and myeloma," Nature Medicine, vol. 4(11):1281-1286 (1998).
Kohler, G. et al., "Continuous cultures of fused cells secreting antibody of predefined specificity," Nature, vol. 256:495-497 (1975).
Koide, Akiko et al., "Monobodies. Antibody Mimics Based on the Scaffold of the Fibronectin Type III Domain," Methods in Molecular Biology, vol. 352: Protein Engineering Protocols, K.M. Arndt (Ed.), Humana Press, Totowa, NJ, Chapter 6, pp. 95-109(2007).

(56) References Cited

OTHER PUBLICATIONS

Koide, Akiko et al., "Stabilization of a Fibronectin Type III Domain by the Removal of Unfavorable Electrostatic Interactions on the Protein Surface," Biochemistry, vol. 40:10326-10333 (2001).

Koide, Akiko et al., "The Fibronectin Type III Domain as a Scaffold for Novel Binding Proteins," J. Mol. Biol., vol. 284:1141-1151 (1998).

Koide, Shohei et al., "Directed Evolution of Fibronectin Type III Domain to Novel Ligand Binding Proteins," FASEB J., vol. 11(9 Suppl.), Poster No. M40, p. A837, (1997).

Koide, Shohei et al., "Directed Evolution of Fibronectin Type III Domain to Novel Ligand Binding Proteins," The Faseb Journal, vol. 11(9):A1155, Poster No. 1739 (1997).

Ku, Jung et al., "Alternate protein frameworks for molecular recognition," Proc. Natl. Acad. Sci. USA, vol. 92:6552-6556 (1995).

Kurz, Markus et al., "Psoralen photo-crosslinked mRNA-puromycin conjugates: a novel template for the rapid and facile preparation of mRNA-protein fusions," Nucleic Acids Research, vol. 28(18):e83, 5 pages (2000).

Kussie, Paul H. et al., "A Single Engineered Amino Acid Substitution Changes Antibody Fine Specificity," Journal of Immunology, vol. 152:146-152 (1994).

Leahy, Daniel J. et al., "2.0 A Crystal Structure of a Four-Domain Segment of Human Fibronectin Encompassing the RGD Loop and Synergy Region," Cell, vol. 84:155-164 (1996).

Leahy, Daniel J. et al "Structure of a Fibronectin Type III Domain from Tenascin Phased by MAD Analysis of the Selenomethionyl Protein," Science, vol. 258:987-991 (1992).

Lee, Grace et al., "Strong Inhibition of Fibrogen Binding to Platelet Receptor Alpha2b beta 3 by RGD Sequences installed into the Presentation Scaffold," Prot. Eng., vol. 6:745-754 (1993).

Lipovsek, D., "Adnectins: engineered target-binding protein therapeutics," Protein Engineering, Design & Selection, vol. 24(1-2):3-9 (2011).

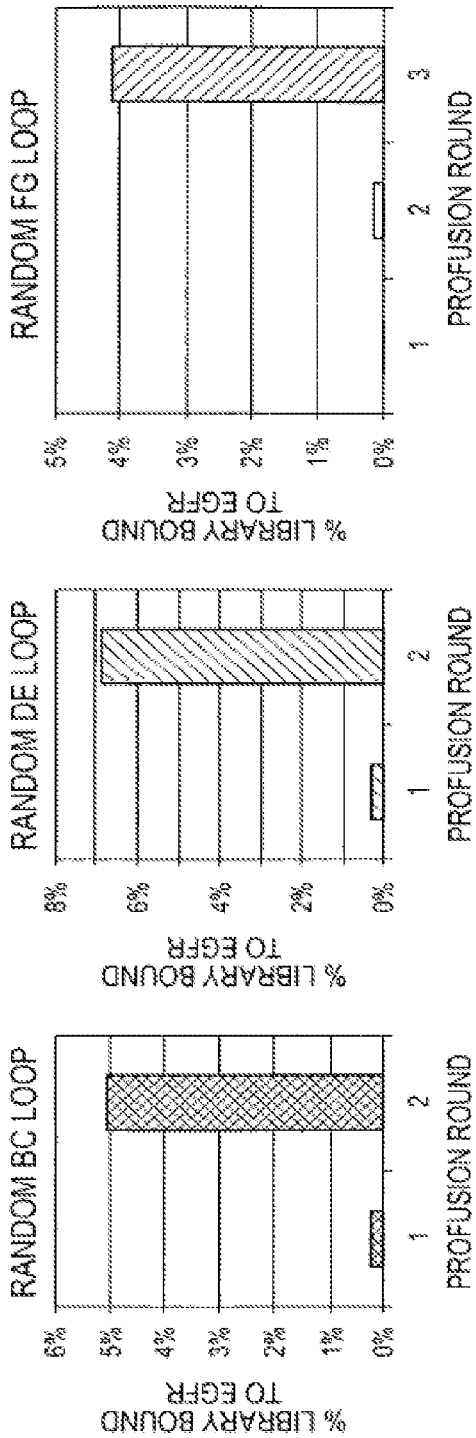
Figure 5A
Figure 5B
Figure 5C
Figure 5D

TARGETED THERAPEUTICS BASED ON ENGINEERED PROTEINS THAT BIND EGFR

RELATED APPLICATIONS

This application claims the benefit of U.S. Provisional Application Ser. No. 61/065,955, filed Feb. 14, 2008. All the teachings of the above-referenced application are incorporated herein by reference.

SEQUENCE LISTING

The instant application contains a Sequence Listing which has been submitted electronically in ASCII format and is hereby incorporated by reference in its entirety. Said ASCII copy, created on Nov. 30, 2015, is named MXI_520USCN2_Sequence_Listing.txt and is 238,042 bytes in size.

FIELD OF THE INVENTION

The present invention relates to single domain proteins that bind to epidermal growth factor receptor (EGFR). The invention also relates to single domain proteins for use in diagnostic, research and therapeutic applications. The invention further relates to cells comprising such proteins, polynucleotide encoding such proteins or fragments thereof, and to vectors comprising the polynucleotides encoding the innovative proteins.

INTRODUCTION

The HER family of receptor tyrosine kinases are important mediators of cell growth, differentiation and survival. The receptor family includes four distinct members including epidermal growth factor receptor (EGFR, ErbB1, or HER1), HER2 (ErbB2), HER3 (ErbB3) and HER4 (ErbB4 or tyro2).

The HER family has been causally implicated in human malignancy. Abnormal activity of the Her family of receptors is involved with breast cancer. EGFR, Her-3, and Her-4 are frequently expressed in ovarian granulosa cell tumors (Leibl, S. et al., Gynecol Oncol 101:18-23 (2005). In particular, increased expression of EGFR has been observed in breast, bladder, lung, head, neck and stomach cancer as well as glioblastomas.

Increased EGFR receptor expression may be associated with increased production of a EGFR ligand, transforming growth factor alpha (TGF-α), by the same tumor cells resulting in receptor activation by an autocrine stimulatory pathway. Baselga and Mendelsohn Pharmac. Ther. 64:127-154 (1994). Monoclonal antibodies directed against the EGFR or its ligands have been evaluated as therapeutic agents in the treatment of such malignancies. See, e.g., Baselga and Mendelsohn., supra; Masui et al. Cancer Research 44:1002-1007 (1984); and Wu et al. J. Clin. Invest. 95:1897-1905 (1995).

HER receptors generally reside in various combinations in cells. Their heterodimerization is thought to increase the diversity of cellular responses to a variety of HER ligands (Earp et al. Breast Cancer Research and Treatment 35: 115-132 (1995)). EGFR is bound by at least six different ligands; epidermal growth factor (EGF), transforming growth factor alpha (TGF-α), amphiregulin, heparin binding epidermal growth factor (HB-EGF), betacellulin and epiregulin (Groenen et al. Growth Factors 11:235-257 (1994)).

EGF binds to EGFR, which forms a heterodimer with HER2, activating EGFR and resulting in transphosphorylation of HER. Dimerization and/or transphosphorylation activates the HER2 tyrosine kinase.

The potential side effects of therapeutics is an important issue to consider when devising a treatment regiment. As an example, cetuximab (Erbitux™), an anti-EGFR antibody, has been associated with potentially life threatening infusion reactions (Thomas, M., Clin J Oncol Nurs. 9(3):332-8 (2005)). Gefitinib (Iressa™) and erlotinib (Tarceva™), both EGFR specific small molecule inhibitors, are associated with a risk of interstitial lung disease (Sandler A., Oncology 20(5 Suppl 2):35-40 (2006)). Individual patients may be predisposed to particular types of complications that affect the choice of drug treatment. Offering a greater choice of treatment options allows physicians to select the therapeutic with the best side effect profile for an individual patient. The present invention provides novel polypeptides and protein therapeutics useful in methods of treatment.

In view of the role that EGFR signaling plays in disorders, including cancer and proliferative disorders, it would be desirable to generate therapeutics, such as EGFR binding polypeptides, that selectively modulate, inhibit or block EGFR.

In addition, it would be desirable for such a therapeutic to be expressed in a cost effective manner, possess desirable biophysical properties (e.g. Tm, substantially monomeric, or well folded), have a small size to penetrate tissues, and have a suitable half life in vivo.

SUMMARY OF THE INVENTION

One aspect of the application provides a polypeptide comprising a fibronectin type III (Fn3) domain, wherein the Fn3 domain (i) comprises a loop, AB; a loop, BC; a loop, CD; a loop, DE; a loop EF; and a loop FG; (ii) has at least one loop selected from loop BC, DE, and FG with an altered amino acid sequence relative to the sequence of the corresponding loop of the human Fn3 domain, and (iii) binds human epidermal growth factor receptor (EGFR). In some embodiments, the polypeptide binds EGFR with a $K_D$ of less than $10^{-4}$M, $10^{-5}$M, $10^{-6}$M, $10^{-7}$M, $10^{-8}$M, $10^{-9}$M, or $10^{-9}$M. In some embodiments, at least two loops of the Fn3 domain are altered. In some embodiments, loop BC and loop FG have an altered amino acid sequence relative to the sequence of the corresponding loop of the human Fn3 domain. In some embodiments, at least three loops of the Fn3 domain are altered. In some embodiments, at least two loops of the Fn3 domain bind EGFR. In some embodiments, at least three loops of the Fn3 domain bind EGFR. In some embodiments, at least 1, 2, 3, 4, 5, 6, 7, 8, 9, or 10 amino acids in at least one loop selected from loop BC, DE, and FG are substituted with an amino acid that differs from the wild-type sequence. In some embodiments, at least 1, 2, 3, 4, 5, 6, 7, 8, 9, or 10 amino acids are deleted or added to at least one loop selected from loop BC, DE, and FG. In some embodiments, the EGFR binding polypeptide binds to a related receptor, such as HER2 or HER3, with a $K_D$ of more than $10^{-6}$M, $10^{-5}$M, $10^{-4}$M, $10^{-3}$M, or $10^{-2}$M. In some embodiments, the EGFR binding polypeptide inhibits EGFR binding to one or more EGFR ligands. In some embodiments, the EGFR binding polypeptide inhibits EGFR signaling.

In some embodiments, the EGFR binding polypeptide is a tenth fibronectin type III domain ($^{10}$Fn3). In some embodiments, the $^{10}$Fn3 comprises the amino acid sequence of any one of SEQ ID NOS: 207-231. In some embodiments, the $^{10}$Fn3 comprises the amino acid sequence of SEQ ID NO: 215. In some embodiments, the $^{10}$Fn3 comprises the amino acid sequence at least 75, 80, 85, 90, 95, or 98% identical to any one of SEQ ID NOS: 207-231.

In some embodiments, the EGFR binding polypeptide further comprises one or more pharmacokinetic (PK) moieties selected from: a polyoxyalkylene moiety, a human serum albumin binding protein, sialic acid, human serum albumin, transferrin, IgG, an IgG binding protein, and an Fc fragment. In some embodiments, the PK moiety is the polyoxyalkylene moiety and said polyoxyalkylene moiety is polyethylene glycol (PEG). In some embodiments, the PEG moiety is covalently linked to the EGFR binding polypeptide via a Cys or Lys amino acid. In some embodiments, the EGFR binding polypeptide is a Fn3 domain. In some embodiments, the PEG is between about 0.5 kDa and about 100 kDa.

In some embodiments, the PK moiety improves one or more pharmacokinetic properties of the polypeptides, e.g., bioavailability, serum half-life, in vivo stability, and drug distribution. In some embodiments, the PK moiety increases the serum half-life of the EGFR binding polypeptide by at least 20, 30, 40, 50, 70, 90, 100, 120, 150, 200, 400, 600, 800% or more relative to the EGFR binding polypeptide alone. In some embodiments, the EGFR binding polypeptide further comprising a PK moiety has a serum in vivo half-life of at least 1, 2, 3, 4, 5, 6, 7, 8, 9, 10, 11, 12, 13, or 14 days.

In some embodiments, the PK moiety and the Fn3 domain are operably linked via at least one disulfide bond, a peptide bond, a polypeptide, a polymeric sugar, or a polyethylene glycol moiety. In some embodiments, the PK moiety and the Fn3 domain are operably linked via a polypeptide comprising the amino acid sequence of SEQ ID NOS: 232-235.

In some embodiments, the EGFR binding polypeptide further comprises a second domain. In some embodiments, the EGFR binding polypeptide further comprises an antibody moiety. In some embodiments, the antibody moiety is less than 50 KDa. In some embodiments, the antibody moiety is less than 40 KDa. In some embodiments, the antibody moiety is a single chain Fvs (scFvs), Fab fragment, Fab' fragment, F(ab')$_2$, disulfide linked Fv (sdFv), Fv, diabody, or whole antibody. In some embodiments, the antibody moiety is a single domain antibody. In some embodiments, the antibody moiety binds a human protein. In some embodiments the antibody moiety binds IGF-IR, FGFR1, FGFR2, FGFR3, FGFR4, c-Kit, human p185 receptor-like tyrosine kinase, HER2, HER3, c-Met, folate receptor, PDGFR, VEGFR1, VEGFR2, VEGFR3, human vascular endothelial growth factor (VEGF) A, VEGF C, VEGF D, human CD20, human CD18, human CD11a, human apoptosis receptor-2 (Apo-2), human alpha4beta7 integrin, human GPIIb-IIIa integrin, stem cell factor (SCF), EGFR, or human CD3.

In some embodiments, the EGFR binding polypeptide further comprises a derivative of lipocalin; a derivative of tetranectin; an avimer; or a derivative of ankyrin. In some embodiments, the EGFR binding polypeptide binds a human protein. In some embodiments the EGFR binding polypeptide binds IGF-IR, FGFR1, FGFR2, FGFR3, FGFR4, c-Kit, human p185 receptor-like tyrosine kinase, HER2, HER3, c-Met, folate receptor, PDGFR, VEGFR1, VEGFR2, VEGFR3, human vascular endothelial growth factor (VEGF) A, VEGF C, VEGF D, human CD20, human CD18, human CD11a, human apoptosis receptor-2 (Apo-2), human alpha4beta7 integrin, human GPIIb-IIIa integrin, stem cell factor (SCF), EGFR, or human CD3.

In some embodiments, the EGFR binding polypeptide is a Fn3 domain and further comprises a second Fn3 domain. The second Fn3 domain (i) comprises a loop, AB; a loop, BC; a loop, CD; a loop, DE; and a loop FG; (ii) has at least one loop selected from loop BC, DE, and FG with an altered amino acid sequence relative to the sequence of the corresponding loop of the human Fn3 domain, and (iii) binds a human protein that is not bound by the human Fn3 domain. In some embodiments, the second Fn3 domain binds IGF-IR, FGFR1, FGFR2, FGFR3, FGFR4, c-Kit, human p185 receptor-like tyrosine kinase, HER2, HER3, c-Met, folate receptor, PDGFR, VEGFR1, VEGFR2, VEGFR3, human vascular endothelial growth factor (VEGF) A, VEGF C, VEGF D, human CD20, human CD18, human CD11a, human apoptosis receptor-2 (Apo-2), human alpha4beta7 integrin, human GPIIb-IIIa integrin, stem cell factor (SCF), EGFR, or human CD3. In some embodiments, the second Fn3 domain binds a human protein with a $K_D$ of less than $10^{-4}$M, $10^{-5}$M, $10^{-6}$M, $10^{-7}$M, $10^{-8}$M, $10^{-9}$M, or $10^{-9}$M. In some embodiments, at least 1, 2, 3, 4, 5, 6, 7, 8, 9, or 10 amino acids in at least one loop selected from loop BC, DE, and FG of the second Fn3 domaina are substituted with an amino acid that differs from the wild-type sequence. In some embodiments, at least 1, 2, 3, 4, 5, 6, 7, 8, 9, or 10 amino acids are deleted or added to at least one loop selected from loop BC, DE, and FG.

In some embodiments, the EGFR binding polypeptide is a $^{10}$Fn3 domain that binds EGFR further comprising a second $^{10}$Fn3 domain. In some embodiments, the second $^{10}$Fn3 domain binds IGF-IR. In some embodiments, the second $^{10}$Fn3 domain binds VEGFR2. In some embodiments, the second $^{10}$Fn3 domain binds EGFR. In some embodiments, the second $^{10}$Fn3 domain comprises the amino acid sequence of any of one of SEQ ID NOS: 2-125, 184-204, or 236. In some embodiments, the second $^{10}$Fn3 domain comprises the amino acid sequence at least 75, 80, 85, 90, 55, or 98% identical to any of one of SEQ ID NOS: 2-125, 184-204, or 236. In some embodiments, the second $^{10}$Fn3 domain comprises the amino acid sequence of any of one of SEQ ID NOS: 126-183, 205, or 206. In some embodiments, the second $^{10}$Fn3 domain comprises the amino acid sequence at least 75, 80, 85, 90, 55, or 98% identical to any of one of SEQ ID NOS: 126-183, 205, or 206. In some embodiments, the second $^{10}$Fn3 domain comprises the amino acid sequence of any of one of SEQ ID NOS: 207-231. In some embodiments, the second $^{10}$Fn3 domain comprises the amino acid sequence at least 75, 80, 85, 90, 55, or 98% identical to any of one of SEQ ID NOS: 207-231.

In some embodiments, the EGFR binding polypeptide further comprises a second domain operably linked via at least one disulfide bond, a peptide bond, a polypeptide, a polymeric sugar, or a polyethylene glycol moiety (PEG). In some embodiments, the PEG is between about 0.5 kDa and about 100 kDa. In some embodiments, the PEG is conjugated to the polypeptide and the second domain via a Cys or Lys residue. In some embodiments, at least the EGFR binding polypeptide or the second domain has no more than a single Cys or Lys. In some embodiments, the single Cys or Lys is located in a non-wildtype location in the amino acid sequence. In some embodiments, the EGFR binding polypeptide comprises SEQ ID NO: 235.

In one aspect, the application provides an EGFR binding polypeptide that inhibits the binding of transforming growth factor alpha (TGF-alpha) or epidermal growth factor (EGF) to EGFR and does not activate human EGFR at sub IC$_{50}$ concentrations in a cell-based assay. In some embodiments, the EGFR binding polypeptide inhibits EGFR binding to one or more EGFR ligands.

In one aspect, the application provides an EGFR binding polypeptide that polypeptide competes with an anti-EGFR antibody for binding to EGFR. In some embodiments, the anti-EGFR antibody is selected from panitumumab, nimotuzumab, zalutumumab, EMD72000, and cetuximab.

In one aspect, the application provides an EGFR binding polypeptide that inhibits total EGF-stimulated phosphotyrosine activation of EGFR with an $IC_{50}$ of less than $10^{-5}$, $10^{-6}$, $10^{-7}$, $10^{-8}$, or $10^{-9}$ M.

In one aspect, the application provides an EGFR binding polypeptide that inhibits ERK phosphorylation with an $IC_{50}$ of less than $10^{-5}$, $10^{-6}$, $10^{-7}$, $10^{-8}$, or $10^{-9}$ M.

In one aspect, the application provides an EGFR binding polypeptide that inhibits AKT phosphorylation with an $IC_{50}$ of less than $10^{-5}$, $10^{-6}$, $10^{-7}$, $10^{-8}$, or $10^{-9}$ M.

In one aspect, the application provides an EGFR binding polypeptide that induces apoptosis in a cell based assay in a cell line dependent on EGFR activation. In some embodiments, EGFR binders block EGFR activities such as control of apoptosis, phosphorylation or dimerization.

In one aspect, the application provides an EGFR binding polypeptide that has been deimmunized to remove one or more T-cell epitopes. In one aspect, the application provides an EGFR binding polypeptide that has been deimmunized to remove one or more B-cell epitopes.

In one aspect, the application provides an EGFR binding Fn3 domain selected by the method comprising a) producing a population of candidate nucleic acid molecules, each comprising a candidate fibronectin type III (Fn3) domain sequence which differs from human Fn3 domain coding sequence, said nucleic acid molecules each comprising a translation initiation sequence and a start codon operably linked to said candidate Fn3 domain coding sequence and each being operably linked to a nucleic acid-puromycin linker at the 3' end; b) in vitro translating said candidate Fn3 domain coding sequences to produce a population of candidate nucleic acid-Fn3 fusions; c) contacting said population of candidate nucleic acid-Fn3 fusions with EGFR; and d) selecting a nucleic acid-Fn3 fusion, the protein portion of which has a binding affinity or specificity for EGFR that is altered relative to the binding affinity or specificity of said human Fn3 for EGFR. In some embodiments, the selected nucleic acid-Fn3 fusion is further optimized by altering one or more nucleic acid residues and rescreening the fusion with EGFR to select for improved binders. In some embodiments the candidate nucleic acid molecule is RNA. In some embodiments the candidate nucleic acid molecule is DNA. In some embodiments, the nucleic acid-puromycin is DNA-puromycin. In some embodiments, the Fn3 domain is $^{10}$Fn3.

In one aspect, the application provides pharmaceutically acceptable compositions comprising an EGFR binding polypeptide. In some embodiments, the composition is essentially endotoxin free. In some embodiments, the compositions is substantially free of microbial contamination making it suitable for in vivo administration. The composition may be formulated, for example, for IV, IP or subcutaneous administration. In some embodiments, the EGFR binding polypeptide inhibits EGFR binding to one or more EGFR ligands. In some embodiments, the EGFR binding polypeptide inhibits EGFR signaling.

One aspect of the application provides methods for the treatment of a subject having a cancer by administering an EGFR binding polypeptide, either alone or in combination with other cytotoxic or therapeutic agents. The cancer can be one or more of, for example, breast cancer, colon cancer, ovarian carcinoma, osteosarcoma, cervical cancer, prostate cancer, lung cancer, synovial carcinoma, glioblastoma, pancreatic cancer, or other cancer yet to be determined in which EGFR levels are elevated, up-regulated, mutated or altered in physiology compared to non-oncogenic cells.

One aspect of the application provides methods for the treatment of a subject having a cancer by administering an EGFR binding polypeptide, either alone or in combination with other cytotoxic or therapeutic agents. In particular, preferred cytotoxic and therapeutic agents include docetaxel, paclitaxel, doxorubicin, epirubicin, cyclophosphamide, trastuzumab, capecitabine, tamoxifen, toremifene, letrozole, anastrozole, fulvestrant, exemestane, goserelin, oxaliplatin, carboplatin, cisplatin, dexamethasone, antide, bevacizumab, 5-fluorouracil, leucovorin, levamisole, irinotecan, etoposide, topotecan, gemcitabine, vinorelbine, estramustine, mitoxantrone, abarelix, zoledronate, streptozocin, rituximab, idarubicin, busulfan, chlorambucil, fludarabine, imatinib, cytarabine, ibritumomab, tositumomab, interferon alpha-2b, melphalam, bortezomib, altretamine, asparaginase, gefitinib, erlonitib, anti-EGF receptor antibody (e.g., cetuximab or panitumumab), ixabepilone, and an epothilone or derivative thereof. More preferably, the therapeutic agent is a platinum agent (such as carboplatin, oxaliplatin, cisplatin), a taxane (such as paclitaxel, docetaxel), gemcitabine, or camptothecin.

Another aspect of the application provides kits comprising one or more of the elements described herein, and instructions for the use of those elements. In some embodiments, a kit includes an EGFR binding polypeptide, alone or with a second therapeutic agent. The instructions for inhibiting the growth of a cancer cell using an EGFR binding polypeptide, alone or with a second therapeutic agent, and/or instructions for a method of treating a patient having a cancer using the same.

A further aspect of the application provides for a cell, comprising a polynucleotide encoding an EGFR binding polypeptide. Vectors containing polynucleotides for such proteins are included as well. Sequences are preferably optimized to maximize expression in the cell type used. Preferably, expression is in *E. coli*. EGFR binding polypeptides can also be expressed, for example, in eukaryotic microbes, including yeast (e.g., *pichia* or *cervaisea*) or blue green algae. Yeast cells can be engineered to produce desired glycosylations. The cells of the invention can be a mammalian cell. In one aspect, the mammalian cell can be engineered to produce desired glycosylations. In one aspect, the cell expresses a fibronectin based scaffold protein. In one aspect, the polynucleotides encoding fibronectin based scaffold proteins are codon optimized for expression in the selected cell type.

The percentage of libraries from Example 1 bound to EGFR-Fc is shown after each selection round. Each RNA-protein fusion library bound to the target after 5 cycles of selection.

Figure 1:
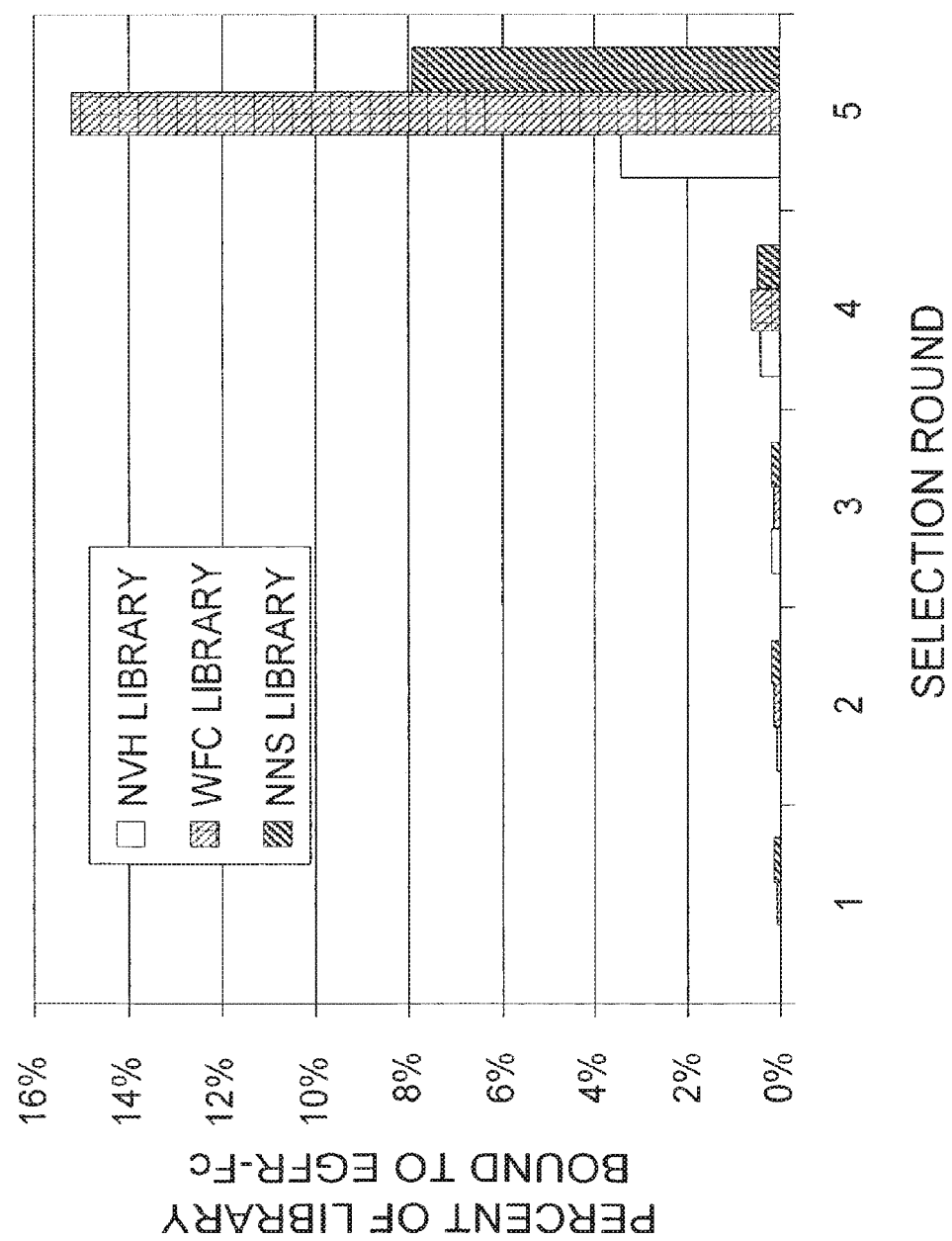
FIG. 1. Selection Profile for Isolation of EGFR-Binding Clones
Figure 2:
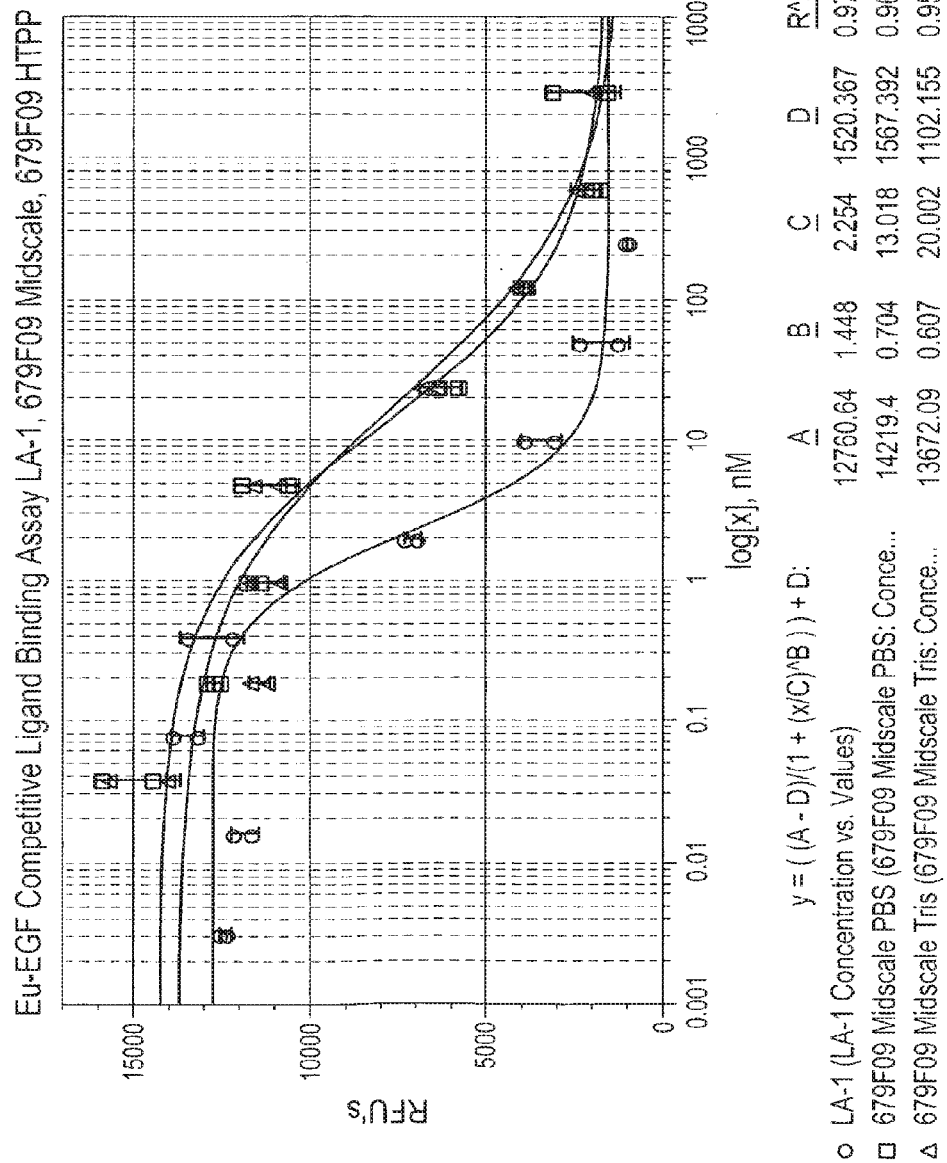

FIG. 2. Cell-Based Competitive Ligand Binding Assay

LA-1 (anti-EGFR monoclonal antibody) and 679F09 (EGFR binding clone) Midscale protein preparations diluted in either PBS buffer or Tris buffer were assayed in the Cell-Based Competitive Ligand Binding Assay (see Material and Methods section for details). LA-1 (circles), 679F09

Midscale PBS (squares) and 679F09 Midscale Tris (triangles) all competed with Eu-EGF for binding to EGFR on A431 cells. The $IC_{50}$'s were: LA-1 (2.254 nM), 679F09 Miscale PBS (13.018 nM) and 679F09 Midscale Tris (20.002 nM).

Figure 3:
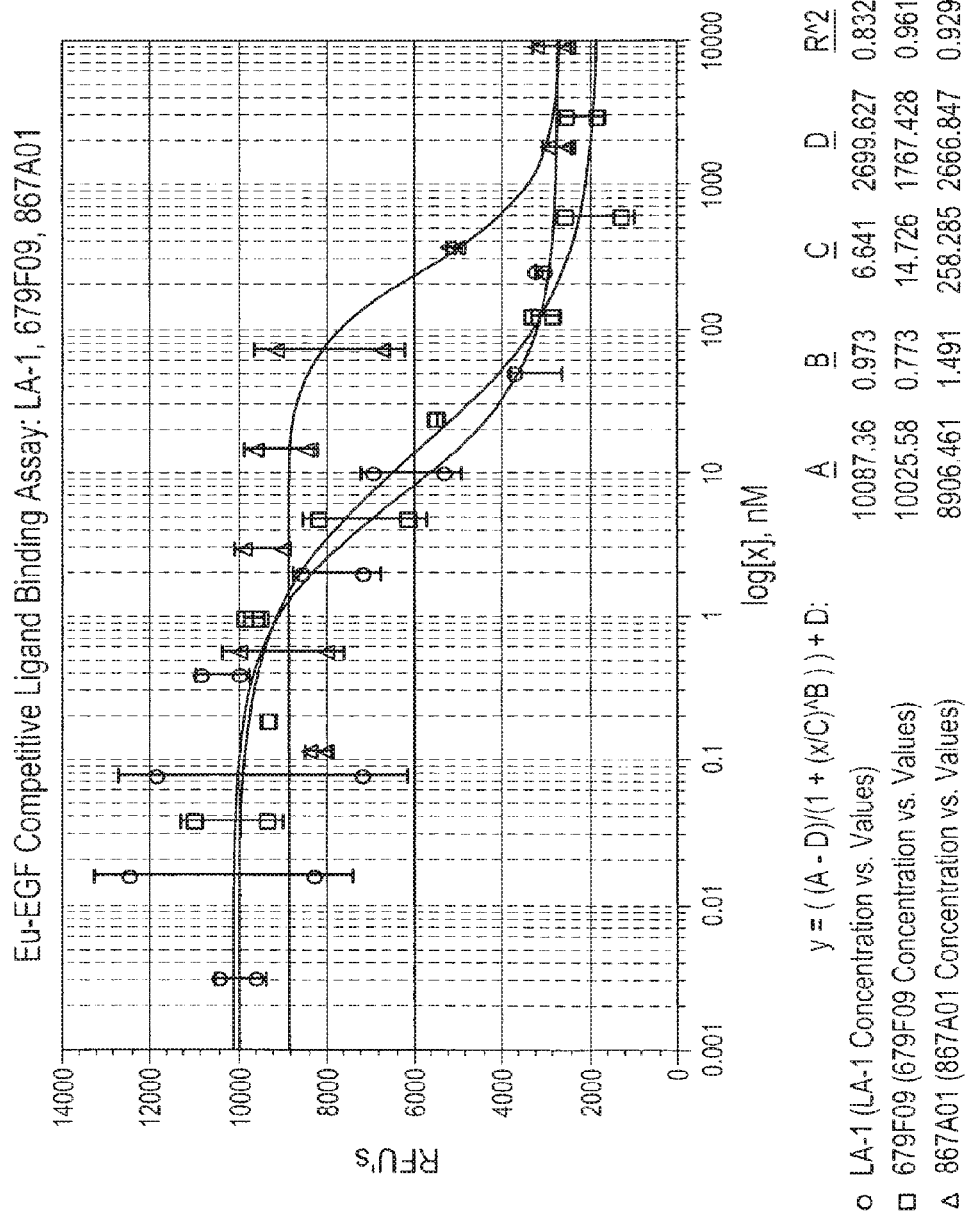

FIG. 3. Cell-Based Competitive Ligand Binding Assay

LA-1 (anti-EGFR monoclonal antibody), 679F09 (EGFR binding clone, Midscale preparation) and 867A01 (EGFR binding clone, HTPP preparation) were assayed in the Cell-Based Competitive Ligand Binding Assay. LA-1 (circles), 679F09 (squares) and 867A01 (triangles) all competed with Eu-EGF for binding to the EGFR on A431 cells. The $IC_{50}$'s were: LA-1 (6.641 nM), 679F09 (14.726 nM) and 867A01 (258.258 nM).

Figure 4:
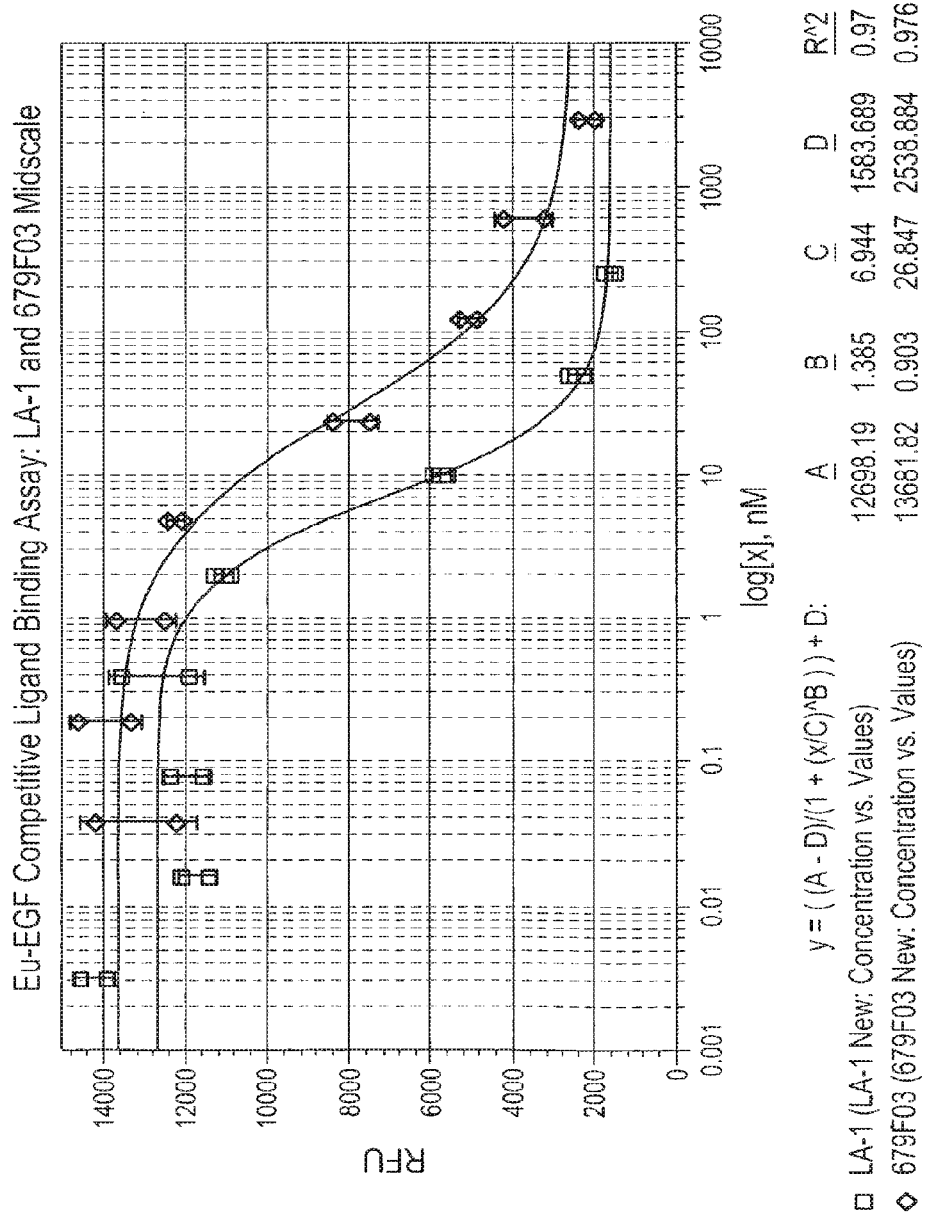

FIG. 4. Cell-Based Competitive Ligand Binding Assay

LA-1 (anti-EGFR monoclonal antibody) and 679F03 (EGFR binding clone, Midscale preparation) were assayed in the Cell-Based Competitive Ligand Binding Assay. LA-1 (squares) and 679F03 (triangles) competed with Eu-EGF for binding to the EGFR on A431 cells. The $IC_{50}$'s were: LA-1 (6.944 nM) and 679F03 (26.847 nM).

FIGS. 5A-5E. Optimization of an EGFR-specific Clones

Figure 5E:
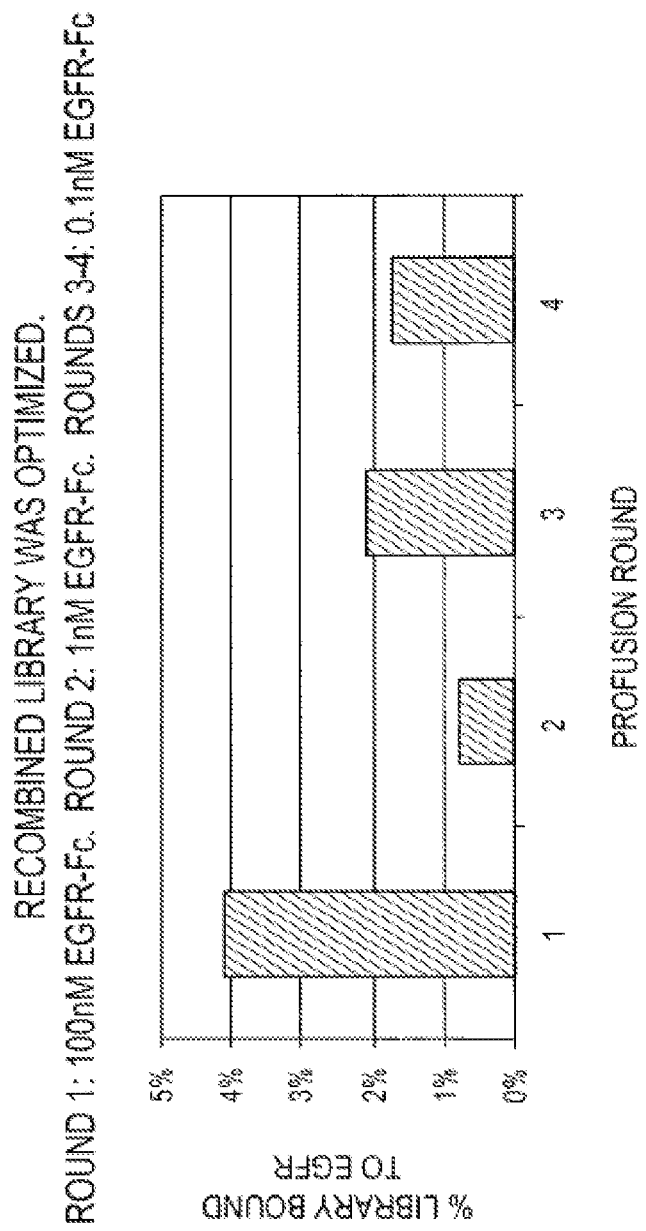

Schematic of process for further optimization of EGFR binding clone as described in Example 4. FIGS. 5A, 5B, and 5C show graphs of the percentage of library bound to EGFR when each of the BC, DE, and FG loops, respectively, were randomized. FIG. 5D is a schematic showing recombination of the individual loops into a master library. FIG. 5E shows a graph of the percentage of the optimized recombined library bound to EGFR.

Figure 6A:
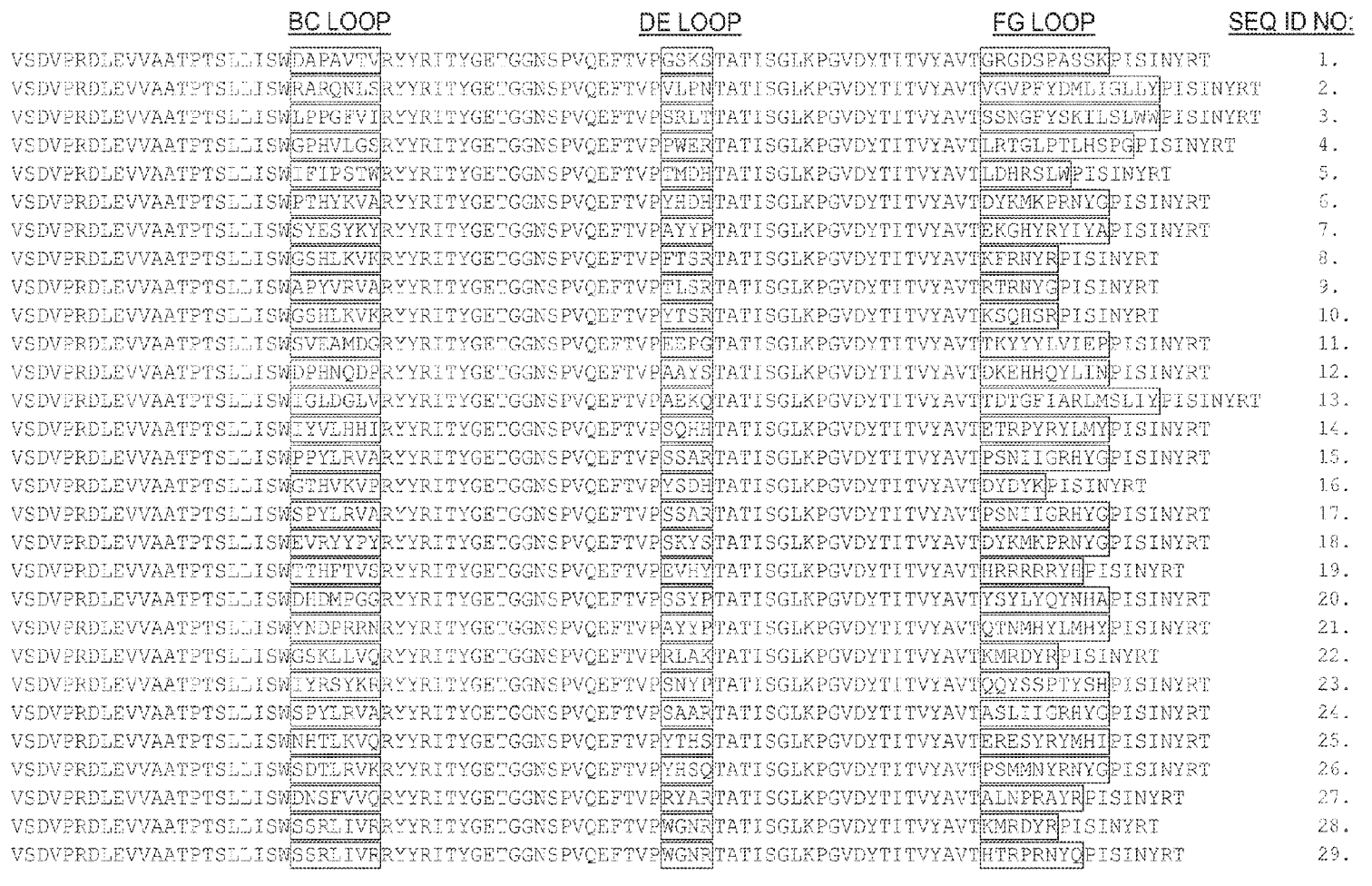
Figure 6B:
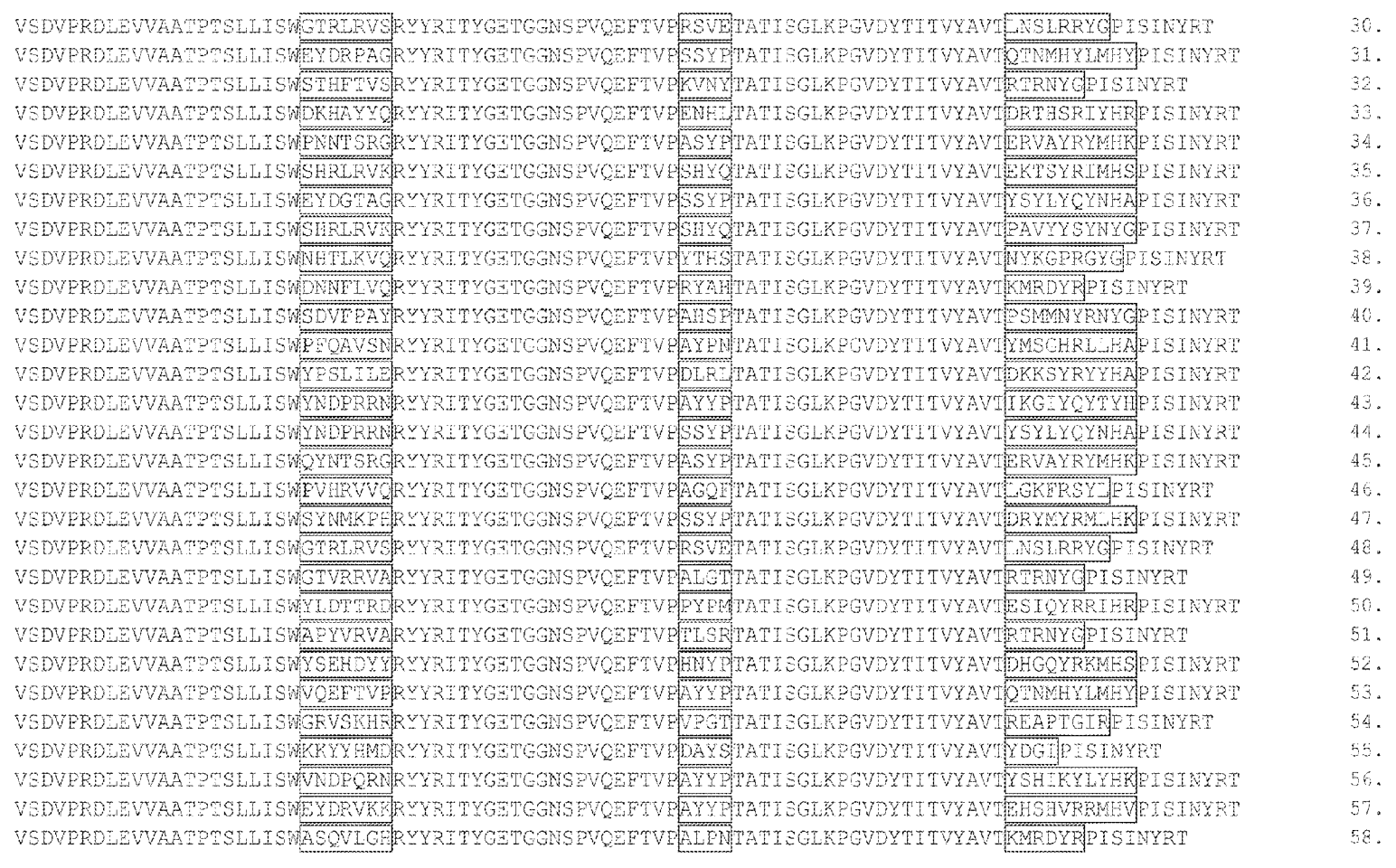
Figure 6C:
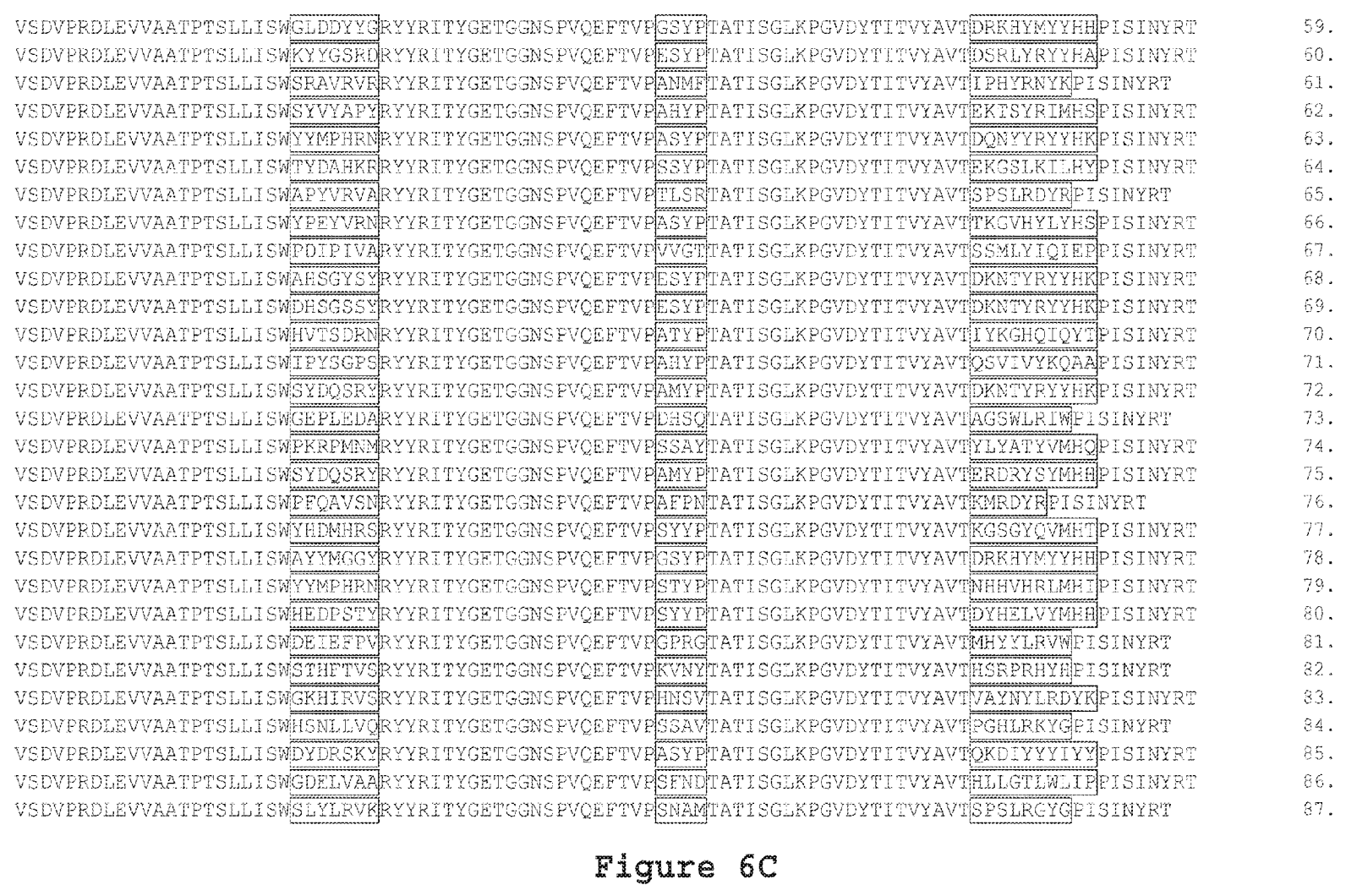
Figure 6D:
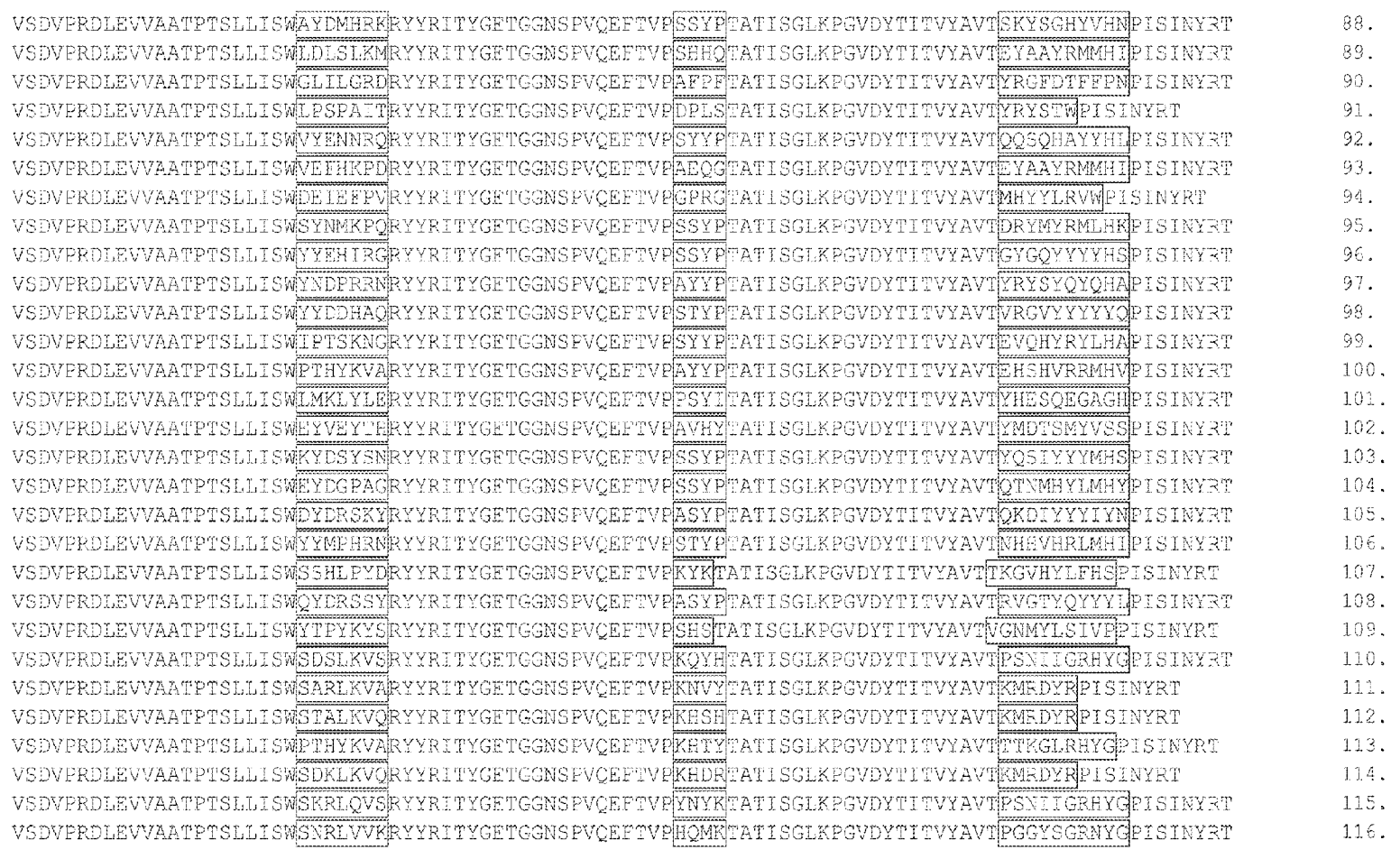
Figure 6E:
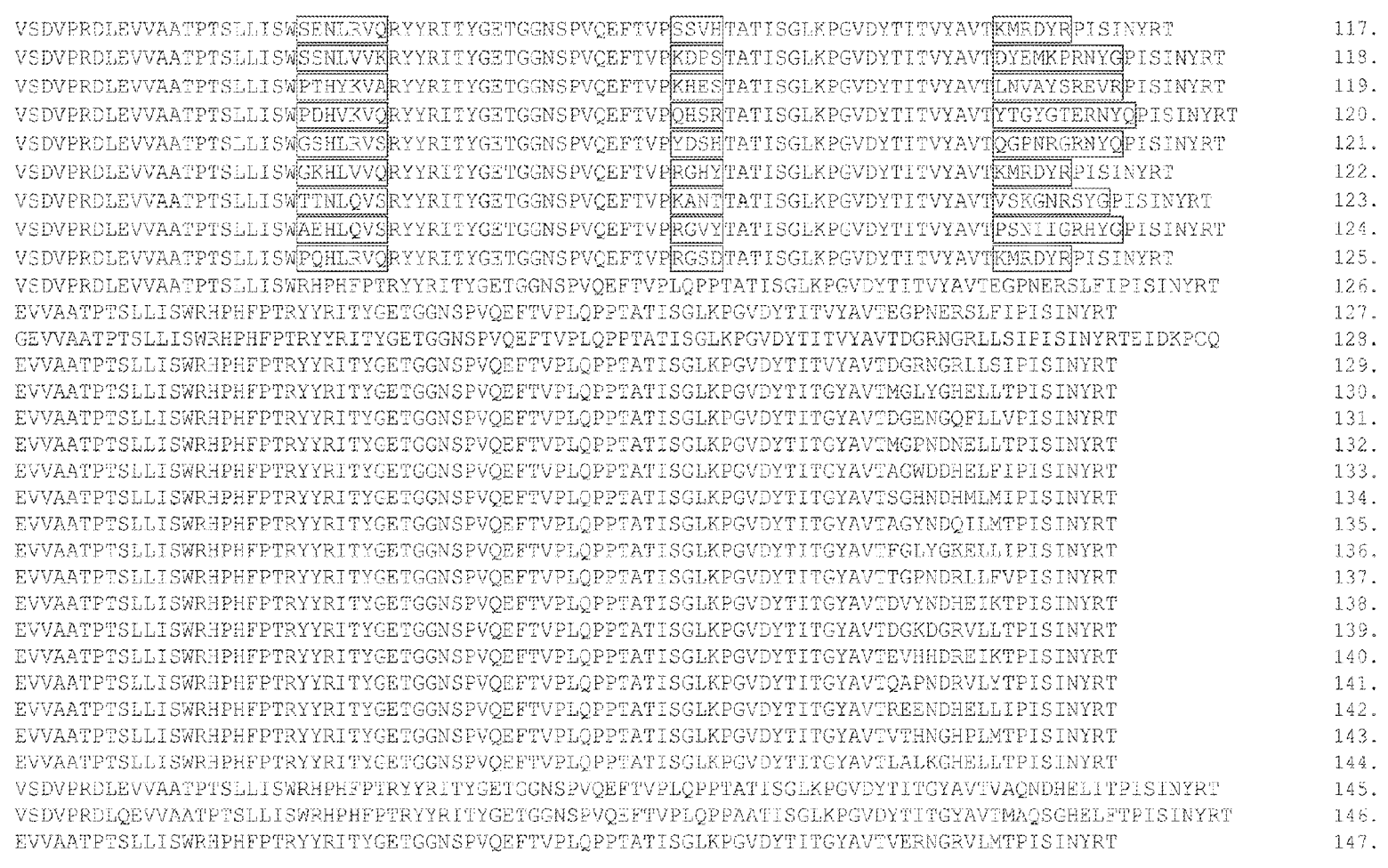
Figure 6F:
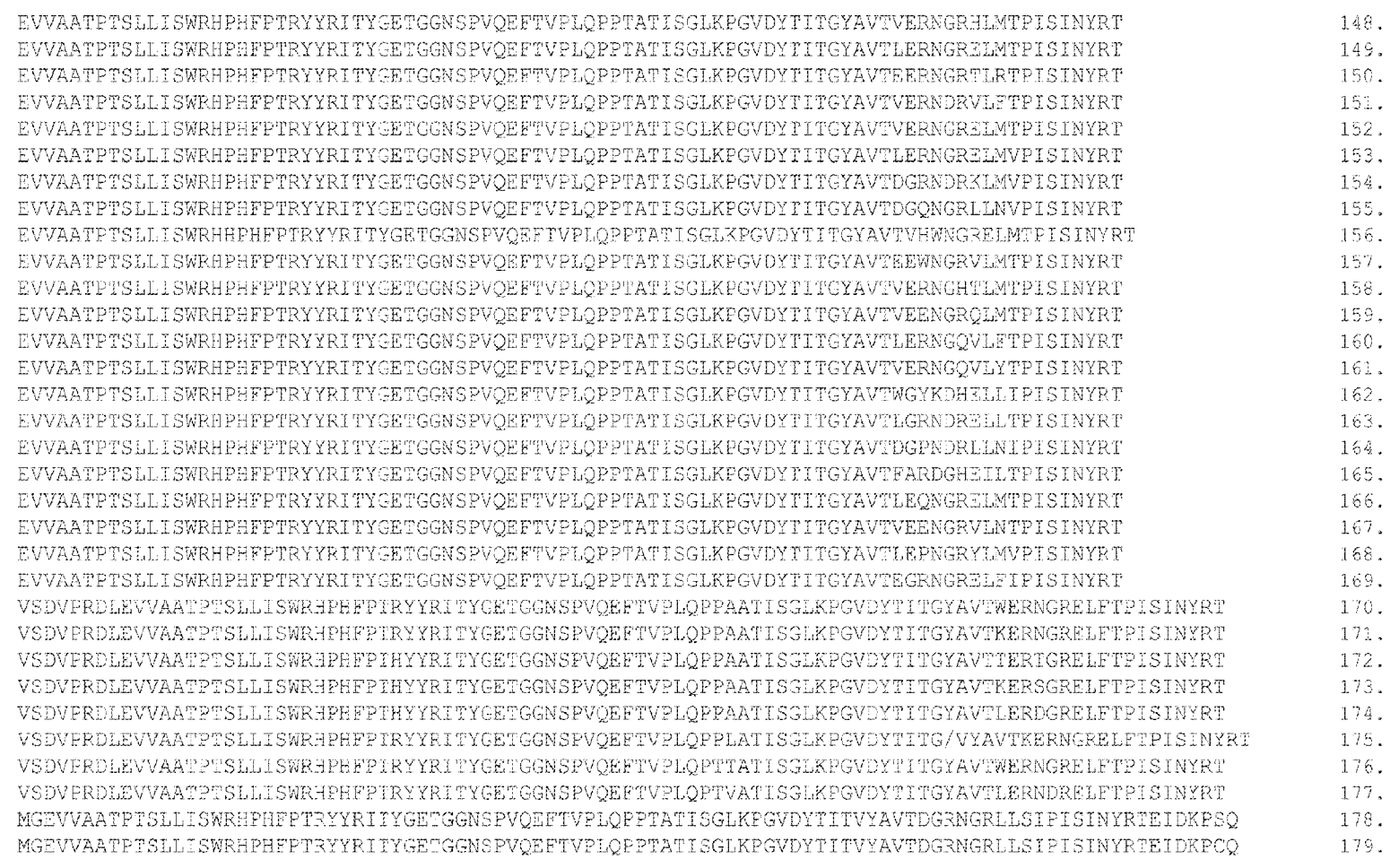

FIGS. 6A-6H depict the sequences described throughout the application. FIG. 6A shows SEQ ID NOs: 1-29, FIG. 6B shows SEQ ID NOs: 30-58, FIG. 6C shows SEQ ID NOs: 59-87, FIG. 6D shows SEQ ID NOs: 88-116, FIG. 6E shows SEQ ID NOs: 117-147, FIG. 6F shows SEQ ID NOs: 148-179, FIG. 6G shows SEQ ID NOs: 180-211, and FIG. 6H shows SEQ ID NOs: 212-236.

DETAILED DESCRIPTION OF THE INVENTION

Definitions

By a "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

The term "single domain polypeptide" is used to indicate that the target binding activity (e.g., EGFR binding activity) of the subject polypeptide is situated within a single structural domain, as differentiated from, for example, antibodies and single chain antibodies, where antigen binding activity is generally contributed by both a heavy chain variable domain and a light chain variable domain. A single domain polypeptide may be attached (e.g., as a fusion protein) to any number of other polypeptides, such as fluorescent polypeptides, targeting polypeptides and polypeptides having a distinct therapeutic effect.

The term "PK" is an acronym for "pharmokinetic" and encompasses properties of a compound including, by way of example, absorbtion, distribution, metabolism, and elimination by a subject. A "PK modulation protein" or "PK moiety" refers to any protein, peptide, or moiety that affects the pharmokinetic properties of a biologically active molecule when fused to or administered together with the biologically active molecule. Examples of a PK modulation protein or PK moiety include PEG, human serum albumin (HSA) binders (as disclosed in U.S. Publication Nos. 20050287153 and 20070003549), human serum albumin, Fc or Fc fragments, and sugars (e.g., sialic acid).

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays known in the art for evaluating such antibody effector functions.

A "native sequence Fc region" comprises an amino acid sequence identical to the amino acid sequence of an Fc region found in nature.

A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

Targets may also be fragments of said targets. Thus a target is also a fragment of said target, capable of eliciting an immune response. A target is also a fragment of said target, capable of binding to a single domain antibody raised against the full length target.

A fragment as used herein refers to less than 100% of the sequence (e.g., 99%, 90%, 80%, 70%, 60%, 50%, 40%, 30%, 20%, 10% etc.), but comprising 5, 6, 7, 8, 9, 10, 12, 13, 14, 15, 16, 17, 18, 19, 20, 21, 22, 23, 24, 25 or more amino acids. A fragment is of sufficient length such that the interaction of interest is maintained with affinity of $1 \times 10^{-6}$M or better.

A fragment as used herein also refers to optional insertions, deletions and substitutions of one or more amino acids which do not substantially alter the ability of the target to bind to a single domain antibody raised against the wild-type target. The number of amino acid insertions deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A protein of the invention that "induces cell death" is one which causes a viable cell to become nonviable. The cell is generally one which expresses the antigen to which the protein binds, especially where the cell overexpresses the antigen. Preferably, the cell is a cancer cell, e.g., a breast, ovarian, stomach, endometrial, salivary gland, lung, kidney, colon, thyroid, pancreatic or bladder cell. In vitro, the cell may be, for example, a SKBR3, BT474, Calu 3, MDA-MB453, MDA-MB-361 or SKOV3 cell. Cell death in vitro may be determined in the absence of complement and immune effector cells to distinguish cell death induced by antibody dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the protein of the invention is able to induce cell death, loss of membrane integrity as evaluated by uptake of propidium iodide (PI), trypan blue (see Moore et al. Cytotechnology 17:1-11 (1995)) or 7AAD can be assessed relative to untreated cells.

A protein of the invention that "induces apoptosis" is one that induces programmed cell death as determined by binding of apoptosis related molecules or events, such as annexin V, fragmentation of DNA, cell shrinkage, dilation of endoplasmic reticulum, cell fragmentation, and/or formation of membrane vesicles (called apoptotic bodies). The cell is one which expresses the antigen to which the protein binds and may be one which overexpresses the antigen. The cell may be a tumor cell, e.g. a breast, ovarian, stomach, endometrial, salivary gland, lung, kidney, colon, thyroid, pancreatic or bladder cell. In vitro, the cell may be, for example, SKBR3, BT474, Calu 3 cell, MDA-MB453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering as disclosed in the example herein; and nuclear/chromatin condensation along with DNA fragmentation can be evaluated by any increase in hypodiploid cells. Preferably, the protein that induces apoptosis is one which results in about 2 to 50 fold, preferably about 5 to 50 fold, and most preferably about 10 to 50 fold, induction of annexin binding relative to untreated cell in an annexin binding assay using cells expressing the antigen to which the protein of the invention binds.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth;

and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the time to disease progression (TTP) and/or determining the response rates (RR).

The half-life of an amino acid sequence or compound can generally be defined as the time taken for the serum concentration of the polypeptide to be reduced by 50%, in vivo, for example due to degradation of the sequence or compound and/or clearance or sequestration of the sequence or compound by natural mechanisms. The half-life can be determined in any manner known per se, such as by pharmacokinetic analysis. Suitable techniques will be clear to the person skilled in the art, and may for example generally involve the steps of suitably administering to the primate a suitable dose of the amino acid sequence or compound to be treated; collecting blood samples or other samples from said primate at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Reference is for example made to to the standard handbooks, such as Kenneth, A et al: Chemical Stability of Pharmaceuticals: A Handbook for Pharmacists and in Peters et al, Pharmacokinete analysis: A Practical Approach (1996). Reference is also made to "Pharmacokinetics", M Gibaldi & D Perron, published by Marcel Dekker, 2nd Rev. edition (1982).

Half-life can be expressed using parameters such as the t½-alpha, t½-beta and the area under the curve (AUC). In the present specification, an "increase in half-life" refers to an increase in any one of these parameters, such as any two of these parameters, or essentially all three these parameters. An "increase in half-life" in particular refers to an increase in the t½-beta, either with or without an increase in the t½-alpha and/or the AUC or both.

The term "EGFR" used herein is equivalent to the term HER-1. The terms "EGFR ligand or EGFR ligands" refers to one or more of the EGFR ligands, such as naturally occurring proteins that bind EGFR.

The term "HER" is used herein to refer to members of the Her family of receptors including EGFR, Her-2, Her-3, and Her-4. Preferably, the Her family member used in the invention is EGFR.

EGFR Binding Polypeptides

In one aspect, the application provides single domain polypeptides that bind EGFR. In certain aspects, a single domain polypeptide may comprise at least five to seven beta or beta-like strands distributed among at least two beta sheets, as exemplified by immunoglobulin and immunoglobulin-like domains. A beta-like strand is a string of amino acids that participates in the stabilization of a single domain polypeptide but does not necessarily adopt a beta strand conformation. A single domain polypeptide may comprise between about 80 and about 150 amino acids that have a structural organization comprising: at least seven beta strands or beta-like strands distributed between at least two beta sheets, and at least one loop portion connecting two beta strands or beta-like strands, which loop portion participates in binding to EGFR. In other words, a loop portion may link two beta strands, two beta-like strands or one beta strand and one beta-like strand. Typically, one or more of the loop portions will participate in EGFR binding, although it is possible that one or more of the beta or beta-like strand portions will also participate in EGFR binding, particularly those beta or beta-like strand portions that are situated closest to the loop portions. In some embodiments, the EGFR binding polypeptide inhibits EGFR binding to one or more EGFR ligands. In some embodiments, the EGFR binding polypeptide inhibits EGFR signaling.

In one aspect, the single domain polypeptide comprises an immunoglobulin (Ig) variable domain. The Ig variable domain may, for example, be selected from the group consisting of: a human $V_L$ domain, a human $V_H$ domain and a camelid $V_{HH}$ domain. One, two, three or more loops of the Ig variable domain may participate in binding to EGFR, and typically any of the loops known as CDR1, CDR2 or CDR3 will participate in EGFR binding.

In one aspect, the single domain polypeptide is a fibronectin based scaffold protein, i.e., a polypeptide based on a fibronectin type III domain (Fn3). An example of fibronectin-based scaffold proteins are Adnectins™ (Adnexus, a Bristol-Myers Squibb R&D Company). Fibronectin is a large protein which plays essential roles in the formation of extracellular matrix and cell-cell interactions; it consists of many repeats of three types (types I, II, and III) of small domains (Baron et al., 1991). Fn3 itself is the paradigm of a large subfamily which includes portions of cell adhesion molecules, cell surface hormone and cytokine receptors, chaperoning, and carbohydrate-binding domains. For reviews see Bork & Doolittle, Proc Natl Acad Sci USA. 1992 Oct. 1; 89(19):8990-4; Bork et al., J Mol Biol. 1994 Sep. 30; 242(4):309-20; Campbell & Spitzfaden, Structure. 1994 May 15; 2(5):333-7; Harpez & Chothia, J Mol Biol. 1994 May 13; 238(4):528-39).

In some embodiments, the application provides fibronectin type III (Fn3) domains that bind EGFR. Such domains may comprise, in order from N-terminus to C-terminus, a beta or beta-like strand, A; a loop, AB; a beta or beta-like strand, B; a loop, BC; a beta or beta-like strand C; a loop CD; a beta or beta-like strand D; a loop DE; a beta or beta-like strand, E; a loop, EF; a beta or beta-like strand F; a loop FG; and a beta or beta-like strand G. Any or all of loops AB, BC, CD, DE, EF and FG may participate in EGFR binding. In some embodiments, loops BC and FG participate in EGFR binding. In some embodiments, loops BC, DE and FG participate in EGFR binding.

In some embodiments, the disclosure provides Fn3 domains having at least one loop selected from loop BC, DE, and FG with an altered amino acid sequence relative to the sequence of the corresponding loop of the human Fn3 domain. By "altered" is meant one or more amino acid sequence alterations relative to a template sequence (corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis. In some embodiments, the EGFR binding Fn3 domain inhibits EGFR binding to one or more EGFR ligands. In some embodiments, the EGFR binding Fn3 inhibits EGFR signaling.

In some embodiments, the Fn3 domain is an Fn3 domain derived from human fibronectin, particularly the tenth Fn3 domain of fibronectin ($^{10}$Fn3), as shown in SEQ ID NO: 1. A variety of mutant $^{10}$Fn3 scaffolds have been reported. In one aspect, one or more of Asp 7, Glu 9, and Asp 23 is replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO02/04523). A variety of additional alterations in the $^{10}$Fn3 scaffold that are either beneficial or neutral have been disclosed. See, for example, Batori et al., Protein Eng. 2002 December; 15(12):1015-20; Koide et al., Biochemistry 2001 Aug. 28; 40(34):10326-33.

Both variant and wild-type $^{10}$Fn3 proteins are characterized by the same structure, namely seven beta-strand domain sequences designated A through G and six loop regions (AB loop, BC loop, CD loop, DE loop, EF loop, and FG loop) which connect the seven beta-strand domain sequences. The beta strands positioned closest to the N- and C-termini may adopt a beta-like conformation in solution. In SEQ ID NO:1, the AB loop corresponds to residues 15-16, the BC loop corresponds to residues 22-30, the CD loop corresponds to residues 39-45, the DE loop corresponds to residues 51-55, the EF loop corresponds to residues 60-66, and the FG loop corresponds to residues 76-87.

In some embodiments, an EGFR binding $^{10}$Fn3 polypeptide may be at least 60%, 65%, 70%, 75%, 80%, 85%, or 90% identical to the human $^{10}$Fn3 domain, shown in SEQ ID NO:1. Much of the variability will generally occur in one or more of the loops. Each of the beta or beta-like strands of a $^{10}$Fn3 polypeptide may consist essentially of an amino acid sequence that is at least 80%, 85%, 90%, 95% or 100% identical to the sequence of a corresponding beta or beta-like strand of SEQ ID NO: 1, provided that such variation does not disrupt the stability of the polypeptide in physiological conditions.

In some embodiments, the disclosure provides EGFR binding polypeptides comprising a tenth fibronectin type III ($^{10}$Fn3) domain, wherein the $^{10}$Fn3 domain comprises a loop, AB; a loop, BC; a loop, CD; a loop, DE; a loop EF; and a loop FG; and has at least one loop selected from loop BC, DE, and FG with an altered amino acid sequence relative to the sequence of the corresponding loop of the human $^{10}$Fn3 domain. By "altered" is meant one or more amino acid sequence alterations relative to a template sequence (corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In some embodiments, one or more loops selected from BC, DE, and FG may be extended or shortened in length relative to the corresponding human fibronectin loop. In some embodiments, the length of the loop may be extended by from 2-25 amino acids. In some embodiments, the length of the loop may be decreased by 1-11 amino acids. In particular, the FG loop of $^{10}$Fn3 is 12 residues long, whereas the corresponding loop in antibody heavy chains ranges from 4-28 residues. To optimize antigen binding, therefore, the length of the FG loop of $^{10}$Fn3 may be altered in length as well as in sequence to cover the CDR3 range of 4-28 residues to obtain the greatest possible flexibility and affinity in antigen binding. In some embodiments, the integrin-binding motif "arginine-glycine-aspartic acid" (RGD) may be replaced by a polar amino acid-neutral amino acid-acidic amino acid sequence (in the N-terminal to C-terminal direction).

In some embodiments, the polypeptide comprising a $^{10}$Fn3 domain comprises the amino acid sequence of any one of SEQ ID NOS: 207-231. Additional sequences may be added to the N- or C-terminus. For example, an additional MG sequence may be placed at the N-terminus. The M will usually be cleaved off, leaving a GVS . . . sequence at the N-terminus. In some embodiments, linker sequences may be placed at the C-terminus of the $^{10}$Fn3 domain, e.g., SEQ ID NOS: 233 and 235.

In certain aspects, the disclosure provides short peptide sequences that mediate EGFR binding. Such sequences may mediate EGFR binding in an isolated form or when inserted into a particular protein structure, such as an immunoglobulin or immunoglobulin-like domain. Examples of such sequences include the amino acid residues that correspond to the BC, DE, and FG loops from SEQ ID NOS: 207-231. In some embodiments, the peptides bind to EGFR with a $K_D$ of less than $10^{-6}$M, $10^{-7}$M, $10^{-8}$M, $10^{-9}$M, $10^{-9}$M or less.

Polypeptide binding to EGFR may be assessed in terms of equilibrium constants (e.g., dissociation, $K_D$) and in terms of kinetic constants (e.g., on rate constant, $k_{on}$ and off rate constant, $k_{off}$). A single domain polypeptide will typically be selected to bind to EGFR with a $K_D$ of less than $10^{-6}$M, $10^{-7}$M, $10^{-8}$M, $10^{-9}$M, $10^{-9}$M or less, although higher $K_D$ values may be tolerated where the $k_{off}$ is sufficiently low or the $k_{on}$ is sufficiently high. In some embodiments, the EGFR binding polypeptide binds to a related receptor, such as HER2 or HER3, with a $K_D$ of more than $10^{-6}$M, $10^{-5}$M, $10^4$M, $10^{-3}$M, $10^{-2}$M or greater.

In one aspect, the application provides for EGFR binding polypeptides further comprising a pharmacokinetic (PK) moiety. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The EGFR binding polypeptides may be attached to a moiety that reduces the clearance rate of the polypeptide in a mammal (e.g., mouse, rat, or human) by greater than three-fold relative to the unmodified polypeptide. Other measures of improved pharmacokinetics may include serum half-life, which is often divided into an alpha phase and a beta phase. Either or both phases may be improved significantly by addition of an appropriate moiety.

Moieties that tend to slow clearance of a protein from the blood, herein refered to as "PK moieties", include polyoxy-alkylene moieties, e.g., polyethylene glycol, sugars (e.g., sialic acid), and well-tolerated protein moieties (e.g., Fc, Fc fragments, transferrin, or serum albumin). The EGFR binding polypeptides may be fused to albumin or a fragment (portion) or variant of albumin as described in U.S. Publication No. 20070048282.

In some embodiments, the PK moiety is a serum albumin binding protein such as those described in U.S. Publication Nos. 2007/0178082 and 2007/0269422.

In some embodiments, the PK moiety is a serum immunoglobulin binding protein such as those described in U.S. Publication No. 2007/0178082.

In some embodiments, the EGFR binding polypeptide comprises polethylene glycol (PEG). One or more PEG molecules may be attached at different positions on the protein, and such attachment may be achieved by reaction with amines, thiols or other suitable reactive groups. The amine moiety may be, for example, a primary amine found at the N-terminus of a polypeptide or an amine group present in an amino acid, such as lysine or arginine. In some embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the EGFR-binding site; d) between the C-terminus and the most C-terminal beta strand or beta-like strand; and e) at the C-terminus.

Pegylation may be achieved by site-directed pegylation, wherein a suitable reactive group is introduced into the protein to create a site where pegylation preferentially occurs. In some embodiments, the protein is modified to introduce a cysteine residue at a desired position, permitting site directed pegylation on the cysteine. In some embodiments, the EGFR binding polypeptide comprises a Cys containing linker such as SEQ ID NO: 235, which permits site directed pegylation. PEG may vary widely in molecular weight and may be branched or linear.

In some embodiments, the EGFR binding polypeptide comprises a Fn3 domain and a PK moiety. In some embodiments, the Fn3 domain is a $^{10}$Fn3 domain. In some embodiments, the PK moiety increases the serum half-life of the EGFR binding polypeptide by more than 5, 10, 20, 30, 40, 50, 60, 70, 80, 90, 100, 120, 150, 200, 400, 600, 800, 1000% or more relative to the Fn3 domain alone.

In some embodiments, the PK moiety is operably linked to the Fn3 domain via at least one disulfide bond, a peptide bond, a polypeptide, a polymeric sugar, or a polyethylene glycol moiety. Exemplary polypeptide linkers include PSTSTST (SEQ ID NO: 232), EIDKPSQ (SEQ ID NO: 233), and GS linkers, such as GSGSGSGSGS (SEQ ID NO: 234) and multimers thereof. In some embodiments the PK moiety is human serum albumin. In some embodiments, the PK moiety is transferrin.

In certain aspects, the disclosure provides EGFR binding polypeptides that bind to EGFR from a first mammal and to a homolog thereof from a second mammal. Such polypeptides are particularly useful where the first mammal is a human and the second mammal is a desirable mammal in which to conduct preclinical testing, such as a mouse, rat, guinea pig, dog, or non-human primate. In some embodiments, an EGFR binding polypeptide will bind to both the preselected human target protein and to the homolog thereof with a $K_D$ of less than $10^{-6}$M, $10^{-7}$M, $10^{-8}$M, $10^{-9}$M, $10^{-9}$M or less.

EGFR binding polypeptides may bind to any part of EGFR. In some embodiments, the polypeptides bind to an extracellular domain of a EGFR. In some embodiments, the polypeptides bind to the ligand binding domain of EGFR and disrupt the interaction of EGFR with one or more ligands, including TGF-alpha and EGF. In some embodiments, EGFR binding polypeptides compete with an anti-EGFR antibody for binding to EGFR. The anti-EGFR antibody may be selected from any known anti-EGFR antibody including panitumumab (Amgen), nimotuzumab (YM Biosciences), zalutumumab (Genmab), EMD72000 (Merck KGaA), and cetuximab (ImClone Systems)

In some embodiments, the polypeptides bind to EGFR and disrupt receptor dimerization. In some embodiments, the EGFR binding polypeptide inhibits EGFR signaling.

In some embodiments, polypeptide binding to EGFR does not activate EGFR at sub-$IC_{50}$ concentrations in cell-based assays.

In some embodiments, EGFR binding polypeptides inhibit downstream signaling of EGFR. EGFR ligand binding leads to homo- or heterodimeric receptor dimerization with EGFR or another HER family member. Dimerization promotes receptor autophosphorylation, which in turn leads to the activation of several signaling pathways. One pathway which is activated is the MAPK pathway, including the phosphorylation of MEK. Another activated pathway is the phosphatidylinositol 3-kinase (PI3K) pathway, including phosphorylation of AKT. Signaling is transduced to the nucleus, resulting in the activation of various transcription factors. In some embodiments, EGFR binding polypeptides inhibit EGFR ligand mediated-EGFR phosphorylation, ERK phosphorylation, AKT phosphorylation, or any other EGFR signaling pathway member with an $IC_{50}$ of less than $10^{-5}$, $10^{-6}$, $10^{-7}$, $10^{-8}$, or $10^{-9}$ M.

Multi-Domain Embodiments

One aspect of the application provides for EGFR binding polypeptides further comprising a second domain. The second domain may bind EGFR or a different protein, preferably a human protein. In some embodiments, the second domain binds a target selected from FGFR, FGFR1, FGFR2, FGFR3, FGFR4, FGFR5, c-Kit, human p185 receptor-like tyrosine kinase, EGFR, HER2, HER3, HER4, c-Met, folate receptor, PDGFR, VEGFR1, VEGFR2, VEGFR3, human vascular endothelial growth factor (VEGF)-A, VEGF-C, VEGF-D, human CD20, human CD18, human CD11a, human apoptosis receptor-2 (Apo-2), human alpha4beta7 integrin, human GPIIb-IIIa integrin, stem cell factor (SCF), human CD3, IGF-IR, Ang1, Ang2, fibroblast growth factor, epidermal growth factor, hepatocyte growth factor, or Tie2.3. In some embodiments, the second domain binds a human target protein with a $K_D$ of less than $10^{-6}$M, $10^{-7}$M, $10^{-8}$M, $10^{-9}$M, or $10^{-9}$M. In some embodiments, the second domain binds an protein related to the target protein with a $K_D$ of more than $10^{-6}$M, $10^{-5}$M, $10^{4}$M, $10^{-3}$M, $10^{-2}$M or greater. In some embodiments, the second domain inhibits the binding target.

One aspect of the application provides an EGFR binding polypeptide further comprising a second domain that binds a tumor associated target or antigen. In some embodiments antigen targeting will help localize the EGFR binding polypeptide in terms of tissue distribution or increased local concentration affect either in the tissue or desired cell type. Alternatively, the second domain may provide an additional mechanism of action to combat cancer along with the EGFR binding polypeptide.

In some embodiments, the second domain binds a tumor associated target or antigen, such as, for example, carbonic anhydrase IX, A3, antigen specific for A33 antibody, BrE3-antigen, CD1, CD1a, CD3, CD5, CD15, CD16, CD19, CD20, CD21, CD22, CD23, CD25, CD30, CD45, CD74, CD79a, CD80, HLA-DR, NCA 95, NCA90, HCG and its subunits, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1-antigen, KS1-4, Le-Y, macrophage inhibition factor (MIF), MAGE, MUC1, MUC2, MUC3, MUC4, PAM-4-antigen, PSA, PSMA, RS5, S100, TAG-72, p53, tenascin, IL-6, IL-8, insulin growth factor-I (IGF-I), insulin growth factor-II (IGF-II), Tn antigen, Thomson-Friedenreich antigens, tumor necrosis antigens, placenta growth factor (PlGF), 17-1A-antigen, an angiogenesis marker (e.g., ED-B fibronectin), an oncogene marker, an oncogene product, and other tumor-associated antigens. Recent reports on tumor associated antigens include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63), each incorporated herein by reference.

Any type of tumor and any type of tumor antigen may be targeted with the corresponding biology of the therapeutic. The cancer can be one or more of, for example, breast cancer, colon cancer, ovarian carcinoma, osteosarcoma, cervical cancer, prostate cancer, lung cancer, synovial carcinoma, pancreatic cancer, melanoma, multiple myeloma, neuroblastoma, and rhabdomyosarcoma, or other cancer yet to be determined in which EGFR levels are elevated, up-regulated, mutated or altered in physiology compared to non-oncogenic cells.

Other exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer.

In some embodiments, the second domain is selected from an antibody moiety.

An antibody moiety refers to immunoglobulin molecules and immunologically active portions of immunoglobulin molecules, i.e., molecules that contain an antigen binding site that immunospecifically binds an antigen. As such, the term antibody moiety encompasses not only whole antibody molecules, but also antibody multimers and antibody fragments as well as variants (including derivatives) of antibodies, antibody multimers and antibody fragments. Examples of antibody moieties include, but are not limited to single chain Fvs (scFvs), Fab fragments, Fab' fragments, F(ab')$_2$, disulfide linked Fvs (sdFvs), and Fvs. Antibody moieties may be, for example, monoclonal, chimeric, human, or humanized.

In some embodiments, the antibody moiety is selected from (i) a Fab fragment, having VL, CL, VH and CH1 domains; (ii) a Fab' fragment, which is a Fab fragment having one or more cysteine residues at the C-terminus of the CH1 domain; (iii) a Fd fragment having VH and CH1 domains; (iv) a Fd' fragment having VH and CH1 domains and one or more cysteine residues at the C-terminus of the CH1 domain; (v) a Fv fragment having the VL and VH domains of a single arm of an antibody; (vi) a dAb fragment (Ward et al., Nature 341, 544-546 (1989)) which consists of a VH domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) a "diabody" with two antigen binding sites, comprising a heavy chain variable domain (VH) connected to a light chain variable domain (VL) in the same polypeptide chain (see, e.g., EP Patent Publication No. 404,097; WO93/11161; and Hollinger et al., Proc. Natl. Acad. Sci. USA, 90:6444-6448 (1993)); and (xi) a "linear antibody" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

In some embodiments, an antibody moiety is a single domain antibody. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be derived from any species including, but not limited to mouse, human, camel, llama, goat, rabbit, bovine.

In some embodiments, a single domain antibody is a naturally occurring single domain antibody such as VHH domains. VHHs are heavy chain variable domains derived from immunoglobulins naturally devoid of light chains such as those derived from Camelidae (including camel, dromedary, llama, vicuna, alpaca and guanaco) as described in WO94/04678. VHH molecules are about 10 times smaller than IgG molecules. Since VHH's are known to bind to 'unusual' epitopes such as cavities or grooves, the affinity of such VHH's may be more suitable for therapeutic treatment, PCT Publication No. WO97/49805.

In some embodiments, the single domain antibody is a VHH that binds a serum protein as described in U.S. Publication No. 20070178082. The serum protein may be any suitable protein found in the serum of subject, or fragment thereof. In some embodiments, the serum protein is serum albumin, serum immunoglobulins, thyroxine-binding protein, transferrin, or fibrinogen.

Various techniques have been developed for the production of antibody fragments that may be used to make antibody fragments used in the invention. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

In some embodiments, the second domain comprises one or more avimer sequences. Avimers were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains that may exhibit improved affinity (in some cases sub-nanomolar) and specificity compared with single-epitope binding proteins. Additional details concerning methods of construction and use of avimers are disclosed, for example, in U.S. Patent Publication Nos. 20040175756, 20050048512, 20050053973, 20050089932 and 20050221384, which is incorporated herein by reference in their entirety.

In some embodiments, the second domain comprises one or more lipocalin related sequences, e.g., anticalins or lipocalin derivatives. Anticalins or lipocalin derivatives are a type of binding proteins that have affinities and specificities for various target molecules, including those described herein. Such proteins are described in US Patent Publication Nos. 20060058510, 20060088908, 20050106660, and PCT Publication No. WO2006/056464.

In some embodiments, the second domain comprises one or more tetranectin C-type lectin related sequences or trinectins, e.g., tetranectin C-type lectin or tetranectin C-type lectin derivatives. Tetranectin C-type lectins or tetranectin C-type lectin derivatives are a type of binding proteins that have affinities and specificities for various target molecules including those described herein. Different tetranectin C-type lectin and related proteins are described in PCT Publication Nos. WO2006/053568, WO2005/080418, WO2004/094478, WO2004/039841, WO2004/005335, WO2002/048189, WO98/056906, and U.S. Patent Publication No. 20050202043.

In some embodiments, the second domain comprises one or more natural ankyrin repeat proteins, e.g., DARPins (Molecular Partners).

In some embodiments, the second domain comprises one or more Affibodies™. Affibodies™ are derived from the IgG binding domain of Staphyloccal Protein A. Novel binding properties can be achieved by altering residues located near the binding surface of the Protein A domain.

In some embodiments, the second domain comprises one or more cystein knot based protein scaffolds, i.e., microbodies (Selecore/NascaCell).

In some embodiments, the second domain comprises one or more Trans-bodies™. Trans-bodies™ are based on transferrin scaffolds (BioResis/Pfizer).

In some embodiments, the second domain comprises binding proteins based on gamma-crystallin or ubiquitin. These so-called Affilin™ (Scil Proteins) molecules are characterized by the de novo design of a binding region in beta sheet structures of the proteins. Affilin™ molecules have been described in U.S Publication No. 20070248536.

In some embodiments, the second domain comprises a Fn3 domain. In some embodiments, the Fn3 domain is an Fn3 domain derived from human fibronectin, particularly the tenth Fn3 domain of fibronectin ($^{10}$Fn3). In some embodiments, the EGFR binding polypeptide is a Fn3 domain.

In some embodiments, one or more loops of the Fn3 domain selected from BC, DE, and FG may be extended or shortened in length relative to the corresponding human fibronectin loop. In some embodiments, the length of the loop may be extended by from 2-25 amino acids. In some embodiments, the integrin-binding motif "arginine-glycine-aspartic acid" (RGD) may be replaced by a polar amino acid-neutral amino acid-acidic amino acid sequence (in the N-terminal to C-terminal direction).

In some embodiments, the Fn3 domain binds human IGF-IR, EGFR, or VEGFR2. In some embodiments, the Fn3 domain binds human IGF-IR, comprises the amino acid sequence of any one of SEQ ID NOS: 2-125, 184-204, 236, and inhibits IGF-IR signaling. In some embodiments, the Fn3 domain binds human EGFR, comprises the amino acid sequence of any one of SEQ ID NOS: 207-231, and inhibits EGFR signaling. In some embodiments, the Fn3 domain binds human VEGFR2, comprises the amino acid sequence of any one of SEQ ID NOS: 126-183, 205, 206, and inhibits VEGFR2 signaling. In some embodiments, the Fn3 domain is a $^{10}$Fn3 domain comprising the amino acid sequence of any one of SEQ ID NOS: 2-231 or 236. In some embodiments, the $^{10}$Fn3 domain comprises an amino acid sequence at least 75, 80, 85, 90, 95, or 98% identical to any one of SEQ ID NOS: 2-231 or 236.

Conjugation

One aspect of the application provides polypeptides comprising an EGFR binding polypeptide and a second domain operably linked via at least one disulfide bond, a peptide bond, a polypeptide, a polymeric sugar, or a PEG moiety.

In some embodiments, the EGFR binding polypeptide and the second domain are operably linked via a polypeptide. In some embodiments, the polypeptide linker is SEQ ID NOS: 233 or 235.

In some embodiments, the EGFR binding polypeptide and the second domain are operably linked via a polypeptide linker having a protease site that is cleavable by a protease in the blood or target tissue. Such embodiments can be used to release two or more therapeutic proteins for better delivery or therapeutic properties or more efficient production compared to separately producing such proteins.

In some embodiments, the EGFR binding polypeptide and the second domain are operably linked via a biocompatible polymer such as a polymeric sugar. Such polymeric sugar can include an enzymatic cleavage site that is cleavable by an enzyme in the blood or target tissue. Such embodiments can be used to release two or more therapeutic proteins for better delivery or therapeutic properties or more efficient production compared to separately producing such proteins.

In some embodiments, the EGFR binding polypeptide and the second domain are operably linked via a polymeric linker. Polymeric linkers can be used to optimally vary the distance between each protein moiety to create a protein with one or more of the following characteristics: 1) reduced or increased steric hindrance of binding of one or more protein domain when binding to a protein of interest, 2) increased protein stability or solubility without searching for additional amino acid substitutions to increase stability or solubility (e.g., solubility at least about 20 mg/ml, or at least about 50 mg/ml), 3) decreased protein aggregation without searching for additional amino acid substitutions to decrease stability (e.g., as measured by SEC), and 4) increased the overall avidity or affinity of the protein by adding additional binding domains.

In some embodiments, the EGFR binding polypeptide is a $^{10}$Fn3 domain comprising the linker of SEQ ID NO: 235. PEG is conjugated to the cysteine moiety in the linker sequence and operably links the EGFR binding polypeptide to a second domain.

PEGylated Embodiments

One aspect of the application provides linking the EGFR binding polypeptides to nonproteinaceous polymers. In some embodiments, the polymer is polyethylene glycol ("PEG"), polypropylene glycol, or polyoxyalkylenes, as described in U.S. Pat. Nos. 4,640,835; 4,496,689; 4,301,144; 4,670,417; 4,791,192 or 4,179,337. In some embodiments, the EGFR binding polypeptides comprise an Fn3 domain. In some embodiments, the polymer is a PEG moiety. In addition, the application provides N or C terminal PEG conjugation to antibody moieties (e.g., camel antibodies and their derivatives, as well as single chain and domain antibodies; and particularly those expressed from microbes) and antibody-like moieties (e.g., derivatives of lipocalins, ankyrins, multiple Cys-Cys domains, and tetranectins; and particularly those expressed from microbes).

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_{n-1}CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, European Published Application No. 473084A and U.S. Pat. No. 5,932,462. One form of PEGs includes two PEG side-chains (PEG2) linked via the primary amino groups of a lysine (Monfardini, C., et al., Bioconjugate Chem. 6 (1995) 62-69).

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al, J. Biol. Chem., 252, 3571 (1977) and J. Biol. Chem., 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

The size of PEG utilized will depend on several factors including the intended use of the EGFR binding polypeptide. Larger PEGs are preferred to increase half life in the body, blood, non-blood extracellular fluids or tissues. For in vivo cellular activity, PEGs of the range of about 10 to 60 kDa are preferred, as well as PEGs less than about 100 kDa and more preferably less than about 60 kDa, though sizes greater than about 100 kDa can be used as well. For in vivo imaging application, smaller PEGs, generally less than about 20 kDa, may be used that do not increase half life as much as larger PEGs so as to permit quicker distribution and less half life. A variety of molecular mass forms of PEG can be selected, e.g., from about 1,000 Daltons (Da) to 100,000 Da (n is 20 to 2300), for conjugating to binding polypeptides of the invention. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270). In some embodiments, one PEG moiety is conjugated to the EGFR binding polypeptide. In some embodiments, the PEG moiety is about 30, 40, 50, 60, 70, 80, or 90 KDa.

In some embodiments, PEGylated EGFR binding polypeptides contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, or from about 10,000 Da to 36,000 Da. In a one embodiment, the PEG in pegylated binding polypeptide is a substantially linear, straight-chain PEG.

One skilled in the art can select a suitable molecular mass for PEG, e.g., based on how the pegylated binding polypeptide will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91-114 (1993).

In some embodiments, an EGFR binding polypeptide is covalently linked to one poly(ethylene glycol) group of the formula: —CO—$(CH_2)_x$—$(OCH_2CH_2)_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's ε-amino group of a lysine is the available (free) amino group.

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. Nos. 5,281,698 and 5,932,462). In a similar type of reaction, 1,1'-(dibenzotriazolyl)carbonate and di-(2-pyridyl) carbonate may be reacted with PEG to form PEG-benzotriazolyl and PEG-pyridyl mixed carbonate (U.S. Pat. No. 5,382,657), respectively.

Pegylation of an EGFR binding polypeptide can be performed according to the methods of the state of the art, for example by reaction of the binding polypeptide with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., Bioconjugate Chem. 6 (1995) 62-69). Such methods may used to pegylated at an ε-amino group of a binding polypeptide lysine or the N-terminal amino group of the binding polypeptide.

In another embodiment, PEG molecules may be coupled to sulfhydryl groups on a binding polypeptide (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments, the pegylated an EGFR binding polypeptide is produced by site-directed pegylation, particularly by conjugation of PEG to a cysteine moiety at the N- or C-terminus. In some embodiments, the EGFR binding polypeptide is a Fn3 domain covalently bound to a PEG moiety, wherein at least one of the loops of said Fn3 domain participates in EGFR binding. The PEG moiety may be attached to the Fn3 polypeptide by site directed pegylation, such as by attachment to a Cys residue, where the Cys residue may be positioned at the N-terminus of the Fn3 polypeptide or between the N-terminus and the most N-terminal beta or beta-like strand or at the C-terminus of the Fn3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into an binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (see Himanen et al., Nature. (2001) 20-27; 414 (6866):933-8) and thus the surface-exposed residues identified. In one embodiment, cysteine residues are introduced into binding polypeptides at or near the N- and/or C-terminus, or within loop regions. Pegylation of cysteine residues may be carried out using, for example, PEG-maleiminde, PEG-vinylsulfone, PEG-iodoacetamide, or PEG-orthopyridyl disulfide.

In some embodiments, the pegylated binding polypeptide comprises a PEG molecule covalently attached to the alpha amino group of the N-terminal amino acid. Site specific N-terminal reductive amination is described in Pepinsky et al., (2001) JPET, 297,1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254,12579, and in Chamow et al., (1994) Bioconjugate Chem. 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Publication No. 2002/0044921 and PCT Publication No. WO94/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, *Bioconjug Chem.* 2004; 15(5): 1005-1009.

Conventional separation and purification techniques known in the art can be used to purify PEGylated binding polypeptide, such as size exclusion (e.g., gel filtration) and ion exchange chromatography. Products may also be separated using SDS-PAGE. Products that may be separated include mono-, di-, tri- poly- and unpegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment of the invention, the PEG in a pegylated EGFR binding polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated EGFR binding polypeptides will preferably retain at least about 25%, 50%, 60%, 70%, 80%, 85%, 90%, 95% or 100% of the biological activity associated with the unmodified protein. In one embodiment, biological activity refers to its ability to bind to EGFR, as assessed by $K_D$, $k_{on}$ or $k_{off}$. In one specific embodiment, the pegylated binding polypeptide protein shows an increase in binding to EGFR relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Deimmunization of EGFR Binding Polypeptides

In one aspect, the application provides deimmunized EGFR binding polypeptides. In some embodiments, the sequence of an EGFR binding polypeptide has been altered to eliminate one or more B- or T-cell epitopes. In some embodiments, the EGFR binding polypeptide comprises an $^{10}$Fn3 domain.

The EGFR binding polypeptide may be deimmunized to render it non-immunogenic, or less immunogenic, to a given species. Deimmunization can be achieved through structural alterations to the polypeptide. Any deimmunization technique known to those skilled in the art can be employed. One suitable technique, for example, for deimmunizing proteins is described in WO 00/34317, the disclosure of which is incorporated herein in its entirety. In summary, a typical protocol within the general method described therein includes the following steps.

1. Determining the amino acid sequence of the polypeptide;
2. Identifying potential T-cell epitopes within the amino acid sequence of the polypeptide by any method including determination of the binding of peptides to MHC molecules, determination of the binding of peptide: HLA complexes to the T-cell receptors from the species to receive the therapeutic protein, testing of the polypeptide or parts thereof using transgenic animals with HLA molecules of the species to receive the therapeutic protein, or testing such transgenic animals reconstituted with immune system cells from the species to receive the therapeutic protein;

3. By genetic engineering or other methods for producing modified polypeptide, altering the polypeptide to remove one or more of the potential T-cell epitopes and producing such an altered polypeptide for testing.

In one embodiment, the sequences of the polypeptide can be analyzed for the presence of MHC class II binding motifs. For example, a comparison may be made with databases of MHC-binding motifs such as, for example by searching the "motifs" database on the worldwide web at sitewehil.wehi.edu.au. Alternatively, MHC class II binding peptides may be identified using computational threading methods such as those devised by Altuvia et al. (J. Mol. Biol. 249 244-250 (1995)) whereby consecutive overlapping peptides from the polypeptide are testing for their binding energies to MHC class II proteins. Computational binding prediction algorithms include iTope™, Tepitope, SYFPEITHI, EpiMatrix (EpiVax), and MHCpred. In order to assist the identification of MHC class II-binding peptides, associated sequence features which relate to successfully presented peptides such as amphipathicity and Rothbard motifs, and cleavage sites for cathepsin B and other processing enzymes can be searched for.

Having identified potential (e.g. human) T-cell epitopes, these epitopes are then eliminated by alteration of one or more amino acids, as required to eliminate the T-cell epitope. Usually, this will involve alteration of one or more amino acids within the T-cell epitope itself. This could involve altering an amino acid adjacent the epitope in terms of the primary structure of the protein or one which is not adjacent in the primary structure but is adjacent in the secondary structure of the molecule. The usual alteration contemplated will be amino acid substitution, but it is possible that in certain circumstances amino acid addition or deletion will be appropriate. All alterations can be accomplished by recombinant DNA technology, so that the final molecule may be prepared by expression from a recombinant host, for example by well established methods, but the use of protein chemistry or any other means of molecular alteration may also be used.

Once identified T-cell epitopes are removed, the deimmunized sequence may be analyzed again to ensure that new T-cell epitopes have not been created and, if they have, the epitope(s) can be deleted.

Not all T-cell epitopes identified computationally need to be removed. A person skilled in the art will appreciate the significance of the "strength" or rather potential immunogenicity of particular epitopes. The various computational methods generate scores for potential epitopes. A person skilled in the art will recognize that only the high scoring epitopes may need to be removed. A skilled person will also recognize that there is a balance between removing potential epitopes and maintaining binding affinity of the polypeptide. Therefore, one strategy is to sequentially introduce substitutions into the polypeptide and then test for antigen binding and immunogenicity.

In one aspect the deimmunized polypeptide is less immunogenic (or rather, elicits a reduced HAMA response) than the original polypeptide in a human subject. Assays to determine immunogenicity are well within the knowledge of the skilled person. Art-recognized methods of determining immune response can be performed to monitor a HAMA response in a particular subject or during clinical trials. Subjects administered deimmunized polypeptide can be given an immunogenicity assessment at the beginning and throughout the administration of said therapy. The HAMA response is measured, for example, by detecting antibodies to the deimmunized polypeptide, in serum samples from the subject using a method known to one in the art, including surface plasmon resonance technology (BIACORE) and/or solid-phase ELISA analysis. Alternatively, in vitro assays designed to measure a T-cell activation event are also indicative of immunogenicity.

Additional Modifications

In some embodiments, the EGFR binding polypeptides are glycosylated. In some embodiments, the polypeptides are Fn3 domains. Fn3 domains do not normally contain glycosylation sites, however, such glycosylation may be engineered into the protein.

Glycosylation of proteins is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. These can be engineered into the proteins of the invention, in particular fibronectin-based scaffold proteins and their corresponding polynucleotides. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to proteins is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

In some embodiments, the EGFR binding polypeptides are modified to enhance antigen-dependent cell-mediated cytotoxicity (ADCC) and/or complement dependent cytotoxicity (CDC). In some embodiments, the EGFR binding polypeptide is an Fn3 domain further comprising an Fc region. In some embodiments, the Fc region is a variant that enhances ADCC or CDC. The Fc region variant may comprise a human Fc region sequence (e.g., a human IgG1, IgG2, IgG3 or IgG4 Fc region) comprising an amino acid modification (e.g., a substitution) at one or more amino acid positions.

In one embodiment, the variant Fc region may mediate antibody-dependent cell-mediated cytotoxicity (ADCC) in the presence of human effector cells more effectively, or bind an Fc gamma receptor (FcγR) with better affinity, than a native sequence Fc region. Such Fc region variants may comprise an amino acid modification at any one or more of positions 256, 290, 298, 312, 326, 330, 333, 334, 360, 378 or 430 of the Fc region, wherein the numbering of the residues in the Fc region is that of the EU index as in Kabat.

Nucleic Acid-Protein Fusion Technology

In one aspect, the application provides fibronectin type III domains that bind a human target, such as, for example, EGFR, VEGFR2, IGF-IR, and other proteins. One way to rapidly make and test Fn3 domains with specific binding properties is the nucleic acid-protein fusion technology of Adnexus, a Bristol-Myers Squibb R&D Company. This disclosure describes the use of such in vitro expression and tagging technology, termed PROfusion™, that exploits nucleic acid-protein fusions (RNA- and DNA-protein fusions) to identify novel polypeptides and amino acid motifs that are important for binding to EGFR and other proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558; 6,261,804; 6,214,553; 6,281,344; 6,207,446; 6,518,018; PCT Publication Nos. WO00/34784; WO01/64942; WO02/032925; and Roberts and Szostak, Proc Natl. Acad. Sci. 94:12297-12302, 1997, herein incorporated by reference. Further discussion of nucleic acid-protein fusion technology can be found in the Examples and the Material and Methods section of the application.

Vectors & Polynucleotides Embodiments

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 Jan. 21; 100(2):438-42; Sinclair et al. Protein Expr Purif. 2002 October; 26(1):96-105; Connell N D. Curr Opin Biotechnol. 2001 October; 12(5):446-9; Makrides et al. Microbiol Rev. 1996 September; 60(3):512-38; and Sharp et al. Yeast. 1991 October; 7(7):657-78.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO90/13646. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

Expression and cloning vectors usually contain a promoter that is recognized by the host organism and is operably linked to the nucleic acid encoding the protein of the invention, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the protein of the invention.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP Patent Publication No. 73,657. Yeast enhancers also are advantageously used with yeast promoters.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human .beta.-interferon cDNA in mouse cells under the control of a thymidine kinase promoter from herpes simplex virus. Alternatively, the rous sarcoma virus long terminal repeat can be used as the promoter.

Transcription of a DNA encoding proteins of the invention by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the multivalent antibody-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See WO94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Suitable host cells for the expression of glycosylated proteins of the invention are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

In some instance it will be desired to produce proteins in vertebrate cells, such as for glycosylation, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59. (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells;

FS4 cells; a human hepatoma line (Hep G2); and myeloma or lymphoma cells (e.g., Y0, J558L, P3 and NSO cells) (see U.S. Pat. No. 5,807,715). Plant cell cultures of cotton, corn, potato, soybean, petunia, tomato, and tobacco can also be utilized as hosts.

Protein Production

Host cells are transformed with the herein-described expression or cloning vectors for protein production and cultured in conventional nutrient media modified as appropriate for inducing promoters, selecting transformants, or amplifying the genes encoding the desired sequences.

The host cells used to produce the proteins of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO90/03430; WO87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Proteins of the invention can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The proteins of the present invention can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Imaging, Diagnostic and Other Applications

In one aspect, the application provides EGFR binding polypeptides labeled with a detectable moiety. The polypeptides may be used for a variety of diagnostic applications. The detectable moiety can be any one which is capable of producing, either directly or indirectly, a detectable signal. For example, the detectable moiety may be a radioisotope, such as H3, C14 or 13, P32, S35, or I131; a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for conjugating a protein to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). In vitro methods, include conjugation chemistry well know in the art including chemistry compatible with proteins, such as chemistry for specific amino acids, such as Cys and Lys. In order to link a moiety (such as PEG) to a protein of the invention, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups depending on the application. For polypeptides without a Cys amino acid, a Cys can be engineered in a location to allow for activity of the protein to exist while creating a location for conjugation.

EGFR binding polypeptides linked with a detectable moiety also are useful for in vivo imaging. The polypeptide may be linked to a radio-opaque agent or radioisotope, administered to a subject, preferably into the bloodstream, and the presence and location of the labeled protein in the subject is assayed. This imaging technique is useful in the staging and treatment of malignancies. The protein may be labeled with any moiety that is detectable in a subject, whether by nuclear magnetic resonance, radiology, or other detection means known in the art.

EGFR binding polypeptides also are useful as affinity purification agents. In this process, the polypeptides are immobilized on a suitable support, such a Sephadex resin or filter paper, using methods well known in the art.

EGFR binding polypeptides can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

In certain aspects, the disclosure provides methods for detecting EGFR in a sample. A method may comprise contacting the sample with a EGFR binding polypeptide described herein, wherein said contacting is carried out under conditions that allow polypeptide-EGFR complex formation; and detecting said complex, thereby detecting said EGFR in said sample. Detection may be carried out using any technique known in the art, such as, for example, radiography, immunological assay, fluorescence detection, mass spectroscopy, or surface plasmon resonance. The sample will often by a biological sample, such as a biopsy, and particularly a biopsy of a tumor, a suspected tumor. The sample may be from a human or other mammal. The EGFR binding polypeptide may be labeled with a labeling moiety, such as a radioactive moiety, a fluorescent moiety, a chromogenic moiety, a chemiluminescent moiety, or a hapten moiety. The EGFR binding polypeptide may be immobilized on a solid support.

Therapeutic/In Vivo Uses

In one aspect, the application provides EGFR binding polypeptides useful in the treatment of EGFR related disorders. The application also provides methods for administering EGFR binding polypeptides to a subject. In some embodiments, the subject is a human. In some embodiments, the subject has an EGFR related disorder, such as cancer. In some embodiments, the EGFR binding polypeptide inhibits EGFR signaling. In some embodiments, the EGFR binding polypeptide inhibits EGFR binding to one or more EGFR ligands.

In some embodiments, administration of EGFR binding polypeptides to an animal causes a reduction in EGFR levels in EGFR-expressing tumors. In some embodiments, the polypeptide causes a reduction in receptor levels by at least 20, 30, 40, 50, 60, 70, 80% or more compared to an untreated animal.

In some embodiments, administration of an EGFR binding polypeptide inhibits tumor cell growth in vivo. The tumor cell may be derived from any cell type including, without limitation, epidermal, epithelial, endothelial, leukemia, sarcoma, multiple myeloma, or mesodermal cells. Examples of common tumor cell lines for use in xenograft tumor studies include A549 (non-small cell lung carcinoma) cells, DU-145 (prostate) cells, MCF-7 (breast) cells, Colo 205 (colon) cells, 3T3/]GF-IR (mouse fibroblast) cells, NCI H441 cells, HEP G2 (hepatoma) cells, MDA MB 231 (breast) cells, HT-29 (colon) cells, MDA-MB-435s (breast) cells, U266 cells, SH-SY5Y cells, Sk-Mel-2 cells, NCI-H929, RPM18226, and A431 cells. In some embodiments, the polypeptide inhibits tumor cell growth relative to the growth of the tumor in an untreated animal. In some embodiments, the polypeptide inhibits tumor cell growth by 50, 60, 70, 80% or more relative to the growth of the tumor in an untreated animal. In some embodiments, the inhibition of tumor cell growth is measured at least 7 days or at least 14 days after the animals have started treatment with the polypeptide. In some embodiments, another antineoplastic agent is administered to the animal with the polypeptide.

In certain aspects, the disclosure provides methods for treating a subject having a condition which responds to the inhibition of EGFR, i.e., an "EGFR-associated disease". Such a method may comprise administering to said subject an effective amount of any of the EGFR inhibiting polypeptides described herein. In some embodiments, the EGFR binding polypeptide inhibits EGFR signaling. In some embodiments, the EGFR binding polypeptide inhibits EGFR binding to one or more EGFR ligands.

The term "EGFR-associated disease" relates to pathological states which are dependent on EGFR activity. EGFR is involved either directly or indirectly in the signal transduction pathways of various cell activities, including proliferation, adhesion and migration, as well as differentiation. The diseases associated with EGFR activity include the proliferation of tumour cells, pathological neovascularisation, which promotes the growth of solid tumours, neovascularisation in the eye (diabetic retinopathy, age-induced macular degeneration and the like) and inflammation (psoriasis, rheumatoid arthritis and the like).

In certain aspects, the disclosure provides methods for administering EGFR binding polypeptides for the treatment and/or prophylaxis of tumours and/or tumour metastases, where the tumour is particularly preferably selected from the group consisting of brain tumour, tumour of the urogenital tract, tumour of the lymphatic system, stomach tumour, laryngeal tumour, monocytic leukaemia, lung adenocarcinoma, small-cell lung carcinoma, pancreatic cancer, glioblastoma and breast carcinoma, without being restricted thereto.

In certain aspects, the disclosure provides methods for administering EGFR binding polypeptide for the treatment of diseases selected from the group of cancerous diseases consisting of squamous cell carcinoma, bladder cancer, stomach cancer, liver cancer, kidney cancer, colorectal cancer, breast cancer, head cancer, neck cancer, oesophageal cancer, gynecological cancer, thyroid cancer, lymphoma, chronic leukaemia and acute leukaemia.

In certain aspects, the disclosure provides methods for administering EGFR binding polypeptide t for the treatment and/or prophylaxis of diseases caused, mediated and/or propagated by angiogenesis. A disease of this type involving angiogenesis is an ocular disease, such as retinal vascularisation, diabetic retinopathy, age-induced macular degeneration and the like.

In certain aspects, the disclosure provides methods for administering EGFR binding polypeptide for the treatment and/or prophylaxis of diseases selected from the group consisting of retinal vascularisation, diabetic retinopathy, age-induced macular degeneration and/or inflammatory diseases.

In certain aspects, the disclosure provides methods for administering EGFR binding polypeptide for the treatment and/or prophylaxis of diseases selected from the group consisting of psoriasis, rheumatoid arthritis, contact dermatitis, delayed hypersensitivity reaction, inflammation, endometriosis, scarring, benign prostate hyperplasia, immunological diseases, autoimmune diseases and immunodeficiency diseases.

In certain aspects, the disclosure provides methods for administering EGFR binding polypeptide for the treatment and/or prophylaxis of bone pathologies selected from the group consisting of osteosarcoma, osteoarthritis and rickets.

One aspect of the application provides EGFR binding polypeptides that inhibit EGFR tyrosine phosphorylation or receptor levels in vivo or both. In one embodiment, administration of an EGFR binder to an animal causes a reduction in EGFR phosphotyrosine signal in EGFR-expressing tumors. In some embodiments, the EGFR binder causes a reduction in phosphotyrosine signal by at least 20%. In some embodiments, the EGFR binder causes a decrease in phosphotyrosine signal by at least 50, 60, 70, 80, 90% or more.

Additional Agents that May be Used with Appropriate Embodiments of the Invention One aspect of the invention provides EGFR binding polypeptides linked to a cytotoxic agent. Such embodiments can be prepared by in vitro or in vivo methods as appropriate. In vitro methods, include conjugation chemistry well know in the art including chemistry compatible with proteins, such as chemistry for specific amino acids, such as Cys and Lys. In order to link a cytotoxic agent to a polypeptide, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups. For example, conjugates can be constructed using a disulfide exchange reaction or by forming a thioether bond between the antibody and the cytotoxic agent. Preferred cytotoxic agents are maytansinoids, taxanes and analogs of CC-1065.

In some embodiments, an EGFR binding polypeptide is linked to a bacterial toxin, a plant toxin, ricin, abrin, a ribonuclease (RNase), DNase I, a protease, Staphylococcal enterotoxin-A, pokeweed antiviral protein, gelonin, diphtherin toxin, Pseudomonas exotoxin, Pseudomonas endotoxin, Ranpimase (Rap), Rap (N69Q), an enzyme, or a fluorescent protein.

In some embodiments, an EGFR binding polypeptide is linked to maytansinoids or maytansinoid analogs. Examples of suitable maytansinoids include maytansinol and maytansinol analogs. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

In some embodiments, an EGFR binding polypeptide is linked to a taxanes. Taxanes suitable for use in the present invention are disclosed in U.S. Pat. Nos. 6,372,738 and 6,340,701.

In some embodiments, an EGFR binding polypeptide is linked to CC-1065 or its analogs. CC-1065 and its analogs are disclosed in U.S. Pat. Nos. 6,372,738; 6,340,701; 5,846, 545 and 5,585,499.

An attractive candidate for the preparation of such cytotoxic conjugates is CC-1065, which is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine (B. K. Bhuyan et al., Cancer Res., 42, 3532-3537 (1982)).

Cytotoxic drugs such as methotrexate, daunorubicin, doxorubicin, vincristine, vinblastine, melphalan, mitomycin C, chlorambucil, and calicheamicin are also suitable for the preparation of conjugates of the present invention, and the drug molecules can also be linked to EGFR binding polypeptides through an intermediary carrier molecule such as serum albumin.

In other therapeutic treatments or compositions, EGFR binding polypeptides are co-administered, or administered sequentially, with one or more additional therapeutic agents. Suitable therapeutic agents include, but are not limited to, targeted therapeutics, other targeted biologics, and cytotoxic or cytostatic agents. In some instances in will be preferred to administer agents from the same or separate therapeutically acceptable vial, syringe or other administration device that holds a liquid formulation.

Cancer therapeutic agents are those agents that seek to kill or limit the growth of cancer cells while having minimal effects on the patient. Thus, such agents may exploit any difference in cancer cell properties (e.g., metabolism, vascularization or cell-surface antigen presentation) from healthy host cells. Differences in tumor morphology are potential sites for intervention: for example, the second therapeutic can be an antibody such as an anti-VEGF antibody that is useful in retarding the vascularization of the interior of a solid tumor, thereby slowing its growth rate. Other therapeutic agents include, but are not limited to, adjuncts such as granisetron HCl, androgen inhibitors such as leuprolide acetate, antibiotics such as doxorubicin, antiestrogens such as tamoxifen, antimetabolites such as interferon alpha-2a, cytotoxic agents such as taxol, enzyme inhibitors such as ras farnesyl-transferase inhibitor, immunomodulators such as aldesleukin, and nitrogen mustard derivatives such as melphalan HCl, and the like.

The therapeutic agents that can be combined with EGFR binding polypeptides for improved anti-cancer efficacy include diverse agents used in oncology practice (Reference: Cancer, Principles & Practice of Oncology, DeVita, V. T., Hellman, S., Rosenberg, S. A., 6th edition, Lippincott-Raven, Philadelphia, 2001), such as docetaxel, paclitaxel, doxorubicin, epirubicin, cyclophosphamide, trastuzumab, capecitabine, tamoxifen, toremifene, letrozole, anastrozole, fulvestrant, exemestane, goserelin, oxaliplatin, carboplatin, cisplatin, dexamethasone, antide, bevacizumab, 5-fluorouracil, leucovorin, levamisole, irinotecan, etoposide, topotecan, gemcitabine, vinorelbine, estramustine, mitoxantrone, abarelix, zoledronate, streptozocin, rituximab, idarubicin, busulfan, chlorambucil, fludarabine, imatinib, cytarabine, ibritumomab, tositumomab, interferon alpha-2b, melphalam, bortezomib, altretamine, asparaginase, gefitinib, erlonitib, anti-EGF receptor antibody (e.g., cetuximab or panitumab), ixabepilone, epothilones or derivatives thereof, and conjugates of cytotoxic drugs and antibodies against cell-surface receptors. Preferred therapeutic agents are platinum agents (such as carboplatin, oxaliplatin, cisplatin), taxanes (such as paclitaxel, docetaxel), gemcitabine, and camptothecin.

The one or more additional therapeutic agents can be administered before, concurrently, or after the EGFR binding polypeptides. The skilled artisan will understand that for each therapeutic agent there may be advantages to a particular order of administration. Similarly, the skilled artisan will understand that for each therapeutic agent, the length of time between which the agent, and an antibody, antibody fragment or conjugate of the invention is administered, will vary.

Formulation and Administration

Therapeutic formulations comprising EGFR binding polypeptides are prepared for storage by mixing the described proteins having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/ or non-ionic surfactants such as TWEEN™, PLURONICS™ or polyethylene glycol (PEG).

The formulations herein may also contain more than one active compound as necessary for the particular indication being treated, preferably those with complementary activities that do not adversely affect each other. Examples of combinations of active compounds are provided in herein. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the proteins of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated proteins of the invention may remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

While the skilled artisan will understand that the dosage of each therapeutic agent will be dependent on the identity of the agent, the preferred dosages can range from about 10 mg/square meter to about 2000 mg/square meter, more preferably from about 50 mg/square meter to about 1000 mg/square meter.

For therapeutic applications, the EGFR binding polypeptides are administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The method of the present invention can be practiced in vitro, in vivo, or ex vivo.

Administration of EGFR binding polypeptides, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, the protein typically will be formulated at a concentration of about 0.1 mg/ml to 100 mg/ml, although wide variation outside of these ranges is permitted. For the treatment of disease, the appropriate dosage ofEGFR binding polypeptides will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The protein is suitably administered to the patient at one time or over a series of treatments.

The present invention also includes kits comprising one or more of the elements described herein, and instructions for the use of those elements. In a preferred embodiment, a kit of the present invention includes an EGFR binding polypeptides and a therapeutic agent. The instructions for this preferred embodiment include instructions for inhibiting the growth of a cancer cell using the EGFR binding polypeptide and the therapeutic agent, and/or instructions for a method of treating a patient having a cancer using the EGFR binding polypeptide and the therapeutic agent.

Preferably, the therapeutic agent used in the kit is selected from the group consisting of docetaxel, paclitaxel, doxorubicin, epirubicin, cyclophosphamide, trastuzumab, capecitabine, tamoxifen, toremifene, letrozole, anastrozole, fulvestrant, exemestane, goserelin, oxaliplatin, carboplatin, cisplatin, dexamethasone, antide, bevacizumab, 5-fluorouracil, leucovorin, levamisole, irinotecan, etoposide, topotecan, gemcitabine, vinorelbine, estramustine, mitoxantrone, abarelix, zoledronate, streptozocin, rituximab, idarubicin, busulfan, chlorambucil, fludarabine, imatinib, cytarabine, ibritumomab, tositumomab, interferon alpha-2b, melphalam, bortezomib, altretamine, asparaginase, gefitinib, erlonitib, anti-EGF receptor antibody (e.g., cetuximab or panitumumab), ixabepilone, and an epothilone or derivative thereof. More preferably, the therapeutic agent is a platinum agent (such as carboplatin, oxaliplatin, cisplatin), a taxane (such as paclitaxel, docetaxel), gemcitabine, or camptothecin.

The elements of the kits of the present invention are in a suitable form for a kit, such as a solution or lyophilized powder. The concentration or amount of the elements of the kits will be understood by the skilled artisan to varying depending on the identity and intended use of each element of the kit.

The cancers and cells there from referred to in the instructions of the kits include breast cancer, colon cancer, ovarian carcinoma, osteosarcoma, cervical cancer, prostate cancer, lung cancer, synovial carcinoma, pancreatic cancer, melanoma, multiple myeloma, neuroblastoma, and rhabdomyosarcoma.

The dosage of cytotoxic or therapeutic agents administered in the methods described herein can be readily determined by those skilled in the art. Pharmaceutical package inserts may also be consulted when determining the proper dosage.

Additional Patent References

Methods and compositions described in the following additional patent applications and patents are also included in this disclosure:

U.S. Publication Nos. 20050186203; 20050084906; 20050008642; 20040202655; 20040132028; 20030211078;

20060083683; 20060099205; 20060228355; 20040081648; 20040081647; 20050074865; 20040259155; 20050038229; 20050255548; 20060246059; and U.S. Pat. Nos. 5,707,632; 6,818,418; and 7,115,396; and PCT International Application Publication Nos. WO2005/085430; WO2004/019878; WO2004/029224; WO2005/056764; WO2001/064942; and WO2002/032925.

Incorporation by Reference

All documents and references, including patent documents and websites, described herein are individually incorporated by reference to into this document to the same extent as if there were written in this document in full or in part.

EXAMPLES

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

Example 1

Initial Identification of EGFR Binding Molecules

A library of approximately $10^{13}$ RNA-protein fusion variants was constructed based on the scaffold of the tenth type 3 domain of human fibronectin with three randomized regions at positions 23-29, 52-55 and 77-86, amino acid numbering according to SEQ ID NO: 1 (the "NNS" library) (Xu et al, Chemistry & Biology 9:933-942, 2002). Similar libraries were constructed in which mixtures of phosphoramidite trimers were used instead of degenerate codons to give randomized regions lacking tryptophan, phenylalanine and cysteine (the "-WFC" library), or lacking tryptophan, phenylalanine, cysteine, leucine, isoleucine, methionine and valine (the "NVH" library). After conversion to mRNA/cDNA heteroduplexes, libraries of a trillion or more mRNA/cDNA-protein fusions each were incubated with 100 nM EGFR-Fc in solution, and existing complexes were captured on protein G-coated magnetic beads. The cDNA was eluted by treatment with high pH, amplified by PCR, and were used to generate new more focused libraries of mRNA/cDNA-protein fusions that were enriched for binders of EGFR. Five cycles of amplification and selection were carried out in this manner and target binding was monitored by quantitative PCR. Analogous experiments were carried out using the s525 variant of EGFR-Fc (amino acids 1-525 of EGFR fused to Fc), or using EGFR-Fc in the presence of EGF. In each case, the RNA-protein fusion library bound to the target after 5 cycles of selection.

Example 2

Identification of EGFR Binding Clones

Proteins encoded by independent clones were analyzed for binding to the full length ectodomain of EGFR as well as a truncated version containing the first 525 amino acids (EGFR 525) of the EGFR ectodomain in single point direct binding assays. Anti-His antibodies were used to capture protein clones in an oriented fashion followed by incubation with full length EGFR or EGFR 525 Fc fusion proteins. Bound receptor-Fcs were detected via anti-human Fc HRP conjugate with a chromogenic readout (i.e. A450). Representative results (partial) from the screening are presented in Table 1 where the relative binding strengths of 24 clones to full length and truncated EGFRs are shown. Compared to the control (SGE), all clones demonstrate significant EGFR binding. The SGE control is the $^{10}$FN3 domain as shown in SEQ ID NO: 1 with the integrin binding domain (RGD) substituted with amino acids SGE.

TABLE 1

| Clone | EGFR-FL-Fc A450 | EGFR 525-Fc A450 | SEQ ID NO: |
|---|---|---|---|
| SGE | 0.1434 | 0.1385 | |
| 679A01 | 1.568 | 1.5285 | 207 |
| 679A05 | 1.428 | 1.7188 | 208 |
| 679A10 | 0.787 | 0.9251 | 209 |
| 679B01 | 0.213 | 0.5389 | 210 |
| 679B09 | 0.455 | 0.3754 | 211 |
| 679B10 | 1.376 | 1.7437 | 212 |
| 679C10 | 0.467 | 0.803 | 213 |
| 679F03 | 2.367 | 2.4468 | 214 |
| 679F09 | 2.416 | 2.4685 | 215 |
| 679G06 | 2.102 | 0.1282 | 216 |
| 867A01 | 1.4045 | 0.1369 | 217 |
| 867E02 | 1.4179 | 1.4313 | 218 |
| 867A03 | 2.2985 | 1.8519 | 219 |
| 867B04 | 2.8105 | 2.5532 | 220 |
| 867C04 | 1.9493 | 1.5665 | 221 |
| 867A05 | 1.8684 | 1.6112 | 222 |
| 867B05 | 2.8208 | 2.5487 | 223 |
| 867E05 | 1.7157 | 1.6823 | 224 |
| 867C07 | 2.4325 | 2.1811 | 225 |
| 867B08 | 2.6106 | 2.4947 | 226 |
| 867H08 | 1.8953 | 1.7903 | 227 |
| 867B09 | 2.7704 | 2.4136 | 228 |
| 867B10 | 2.955 | 2.5545 | 229 |
| 867F10 | 2.7801 | 2.3242 | 230 |

Example 3

Cell-Based Competitive Ligand Binding Assay

The Cell-Based Competitive Ligand Binding Assay measures the ability of a test sample to bind to EGFR on the surface of human A431 cells and compete with the binding of the natural EGF ligand labeled with a europium tag (Eu-EGF). Competition of the test sample with Eu-EGF for binding to the EGFR's on the cell surface is measured by a decrease in fluorescent signal. Competitive binding of an anti-EGFR antibody (LA-1) is compared to the binding of two EGFR binding clones (679F03, 679F09 and 867A01) in FIGS. 2-4.

Example 4

Initial Optimization of an EGFR-Specific Clone

In order to identify clones with improved affinity and specificity, further mutagenesis was performed to create more focused libraries to optimize the loops binding to EGFR.

Three libraries were constructed in which one loop at a time was replaced with random sequence. The libraries were constructed at the DNA level as described in the Material and Methods section, except that random sequences in two out of three loops were replaced with fixed sequence corresponding to the clone being optimized.

Amplification, synthesis of mRNA-protein fusions, and affinity selection were carried out with these three libraries. Binding percentages were monitored each round and PROfusion™ was continued until each library showed binding above 1%. At this point, the random loops were amplified from each library and reassembled to make a master library in which all 3 loops were optimized (FIG. 5).

The master library containing all 3 optimized loops was taken through cycles of amplification, synthesis of mRNA-protein fusions, and affinity selection. EGFR-Fc was used at decreasing concentrations to select for the highest affinity binders. In round 1, the concentration of EGFR-Fc was 100 nM. In round 2, the concentration of EGFR-Fc was 1 nM. In rounds 3 and 4, the concentration of EGFR-Fc was 0.1 nM.

Example 5

Cell Based Competitive Ligand Binding Assay to Assess Optimized Derivative Clones Selected optimized clones are compared to a pre-optimized clone for their ability to bind to EGFs on the surface of human A431 cells and compete with the binding of the natural EGF ligand labeled with a europium tag (Eu-EGF). Following HTPP and quantitation, many clones may exhibit superior inhibition to the staring clone with $IC_{50}$s in the low nM range.

Example 6

Examination of the Thermal Stability of Optimized EGFR Competitive $IC_{50}$ Clones One liter *E. coli* growths of selected EGFR optimized clones are prepared and the proteins are purified. Differential Scanning calorimetry (DSC) is performed to characterize the energetics of unfolding, or melting temperature, $T_m$, of individual clones.

Example 7

Examination of the Solution Properties of Optimized EGFR Competitive Clones

One liter *E. coli* growths of selected optimized clones are prepared and the proteins are purified. Size-exclusion chromatography (SEC) is used to determine monomeric behavior. Monomericity is confirmed using SEC combined with Multi-Angle Laser Light Scattering (MALLS). "Classical" light scattering (also known as "static" or "Rayleigh" scattering or MALLS) provides a direct measure of molecular mass. It is therefore very useful for determining whether the native state of a protein is a monomer or a higher oligomer, and for measuring the masses of aggregates or other non-native species.

Example 8

Determination of Binding Affinity and Kinetics of Optimized EGFR Competitive Clones One liter *E. coli* growths of selected optimized clones are prepared and the proteins are purified. Surface plasmon resonance (BIAcore) analysis is performed using recombinant, immobilized EGFR and solution-phase clones in order to determine binding kinetics and binding affinities.

Example 9

Determination of Binding of Optimized EGFR Competitive Clones to Other HER-Family Members One liter *E. coli* growths of selected optimized clones are prepared and the proteins are purified. To ensure that the EGFR competitive clones are indeed specific for EGFR, they are evaluated at high concentration against other HER family members or another unrelated receptor using BIAcore methodology. The HER family members or another unrelated receptor are immobilized onto a BIAcore chip as is an irrelevant protein to control for non-specific binding. Clones are passed over the chip at 10 µM to look for non-specific binding or specificity.

Example 10

Activity of EGFR Clones in Cell-Based Assays

The purified EGFR clones are evaluated in cell-based assays in order to confirm activity. In this example, results from clone 679F09 (SEQ ID NO: 215) are described. Clone 679F09 was screened for the ability to directly interfere with ligand-stimulated EGFR activation and downstream MAP kinase signaling. Immunocytochemical assays (In Cell Westerns) were used to measure 1) total phosphorylation of the EGFR, 2) phosphorylation on tyrosine 1068 of the EGFR, a functionally important residue responsible for binding of cytosolic signaling proteins and 3) ERK phosphorylation, a component of the MAP kinase pathway that stimulates growth in response to EGFR activation. These assays were carried out in both A431 epidermoid carcinoma cells and FaDu head & neck carcinoma cells.

In FaDu cells, clone 679F09 blocked EGF-stimulated EGFR phosphorylation on tyrosine 1068 with an $IC_{50}$ of 1.32 µM and blocked EGF-stimulated ERK phosphorylation with an $IC_{50}$ of 2.8 µM. In A431 cells, clone 679F09 blocked EGF-stimulated total EGFR phosphorylation with an $IC_{50}$ of 2.4 µM, EGF-stimulated EGFR phosphorylation on tyrosine 1068 with an $IC_{50}$ of 2.88 µM and blocked EGF-stimulated ERK phosphorylation with an $IC_{50}$ of 3.1 µM.

ELISA assays to measure phosphorylation of AKT, total EGFR phosphorylation, EGFR phosphorylation on tyrosine 1068, and ERK phosphorylation were used to evaluate these same endpoints in DiFi colon carcinoma cells, as this line was not suitable for In Cell Western assays. In DiFi cells, clone 679F09 blocked EGF-stimulated AKT phosphorylation with an $IC_{50}$ between 1.8 µM and 5.3 µM, blocked EGF-stimulated total EGFR phosphorylation with an $IC_{50}$ of 5.3 µM, blocked EGF-stimulated EGFR phosphorylation on tyrosine 1068 with an $IC_{50}$ of 1.49 µM, and blocked EGF-stimulated ERK phosphorylation with an $IC_{50}$ of greater than 4.4 µM.

Example 11

Epitope Mapping

An In Cell Western (ICW) assay was used to determine if EGFR clones could interfere with the binding of other EGFR antibodies to a known epitope on the EGFR extracellular domain. A panel of antibodies was assembled with defined binding regions (Table 2). EGFR clones were incubated with A431 cells, unbound protein was washed away and bound protein crosslinked to the receptor with BS3.

Cells were fixed and probed with an antibody where the binding site is known. If the EGFR clone shares common epitopes with the antibody, binding of the clone to EGFR prevents or reduces binding by the antibody.

Table 2 depicts the results of the competition binding studies with EGFR binding clone 679F09, as well as anti-EGFR antibodies cetuximab and panitumumab.

TABLE 2

Antibodies to the EGFR extracellular domain with defined binding determinants.

| | Clone | SUPPLIER | SPECIES | EPITOPE | Competing |
|---|---|---|---|---|---|
| 1 | | Abcam ab38165 | Rab | Peptide AA 42-58 | |
| 2 | E234 | Abcam ab32198 | Rab | Peptide AA 40-80 (No ICC) | |
| 3 | N-20 | Santa Cruz #31155 | Goat IgG | AA 110-160 | |
| 4 | ICR10 | Abcam ab231 Santa Cruz #57095 | Rat IgG2a | AA 124-176[b], neutralizing[e] | |
| 5 | EGFR1 | Abcam ab30 Chemicon MAB88910 Labvision MS-311 | Mu IgG1 | AA 176-294, neutralizing[b] ab30&MAB88910@ (1 mg/ml) | |
| 6 | 199.12 | Labvision MS-396-P | Mu IgG2a | AA 124-176, non-neutralizing[b] | |
| 7 | LA22 | Upstate 05-104 | Mu IgG2a | AA 351-364, neutralizing[a] | C, P |
| 8 | | Abcam ab15669 | Rab | Peptide AA376-394[d] | |
| 9 | 225 | Sigma E2156 Labvision MS-269-P | Mu IgG1 | AA 294-475, neutralizing[b,c] | C, P, 679F09 |
| 10 | 528 | Abcam ab3103 Santa Cruz #120 Labvision MS-268-P | Mu IgG2a | AA 294-475, neutralizing[b,c] | C, P |
| 11 | B1D8 | Labvision MS-666-P | Mu IgG2a | AA 294-475[b] | C, P, 679F09 |
| 12 | LA1 | Upstate 05-101 | Mu IgG1 | neutralizing | C, P, 679F09 |
| 13 | H11 | Labvision MS-316-P | Mu IgG1 | AA 294-475, non-neutralizing[b] | 679F09 |
| 14 | 111.6 | Labvision MS-378-P | Mu IgG1 | AA 294-475, neutralizing[b] | 679F09 |
| 15 | 29.1 | Sigma E2760 Abcam ab10414 | Mu IgG1 | External carbohydrate non-neutralizing | |

Dilute Abs 1:100, weak binders can be diluted 1:50.
[a]JBC264 (1989) 17469 Ala351-Asp364,
[b]J Immunological Methods 287 (2004) 147,
[c]Mol Biol Med1 (1983) 511,
[d]Raised against a peptide to mouse EGFR,
[e]Int J Oncol4 (1994) 277.
C—cetuximab;
P—panitumumab.

Example 12

Re-Optimization of Clones

One of the commonly seen degradation processes for proteins during storage is the oxidation of methionine or other amino acid residues, such as tryptophan, tyrosine, or histidine. Optimization may be performed in order to select for clones which retain the desirable properties of biological activity and biophysical properties of the starting clone, but are substituted in undesirable methionine residue(s), if present, in the loops. The same approach is used when any tryptophan, tyrosine, histidine residues in the loops are identified as being prone to oxidative damage.

Example 13

Direct Binding Assay for Re-Optimized Derivatives

A direct binding assay is used to screen re-optimized derivatives for enhanced binding to EGFR. Clones that show binding in a single-point assay are analyzed further using a gradient of clone concentrations.

Example 14

Examination of the Solution Properties of Re-Optimized EGFR Competitive Clones

Size-exclusion chromatography (SEC) of HTPP material for re-optimized EGFR competitive clones typically reveals monomeric behavior indicating that at higher protein concentration, optimized clones do not have a tendency to aggregate.

Example 15

Determination of Binding Affinity and Kinetics of Re-Optimized EGFR Competitive Clones One liter *E. coli* growths of selected FG loop optimized EGFR competitive clones are prepared and the proteins are purified. BIAcore analysis is performed using recombinant, immobilized EGFR and solution-phase clones in order to determine binding kinetics and binding affinities. Typically, binding affinities may range from double-digit to triple digit pM for the clones.

Example 16

Determination of Binding of Re-Optimized EGFR Competitive Clones to Other HER Family Members One liter *E. coli* growths of selected FG loop optimized EGFR competitive clones is prepared and the proteins are purified. To ensure that the EGFR competitive clones are indeed specific for EGFR, they are evaluated at high concentration against other HER receptors or another unrelated receptor using Biacore methodology. Typically, the majority of clones will exhibit no detectable binding to other EGFR family members or other unrelated receptors at this high concentration illustrating that these clones are indeed specific to EGFR.

Example 17

Examination of the Thermal Stability of Re-Optimized Clones to EGFR

One liter *E. coli* growths of selected re-optimized EGFR competitive clones are prepared and the proteins are purified. Differential Scanning calorimetry (DSC) is performed to characterize the energetics of unfolding, or melting temperature, $T_m$, of individual clones.

Example 18

PEGylation of Fn3 Domains

PEGylation of Fn3 domains is performed to enhance pharmacokinetic properties. Optimized clones are produced in an *E. coli* expression system with a C-terminal cysteine substitution.

SEQ ID NO: 235 is linked to the N-terminus of a clone lacking cysteine residues. The single sulfhydryl of the cysteine residue from SEQ ID NO: 235 is used to couple to PEG variants using standard maleimide chemistry to yield two different PEGylated forms. Both a linear 20 kDa bifunctional PEG and a mono-functional branched 40 kDa PEG (NOF Corporation) are conjugated to clones. The PEGylated protein forms are purified from unreacted protein and PEG by ion exchange and size-exclusion chromatography. Covalent linkage of the two PEG forms are verified by SDS-PAGE, mass spectrometry and analytical size exclusion chromatography coupled with multi-angle laser light scattering.

Example 19

Determination of Binding Affinity and Kinetics of PEGylated Fn3 Domain Clone Variants Surface plasmon resonance (Biacore) analysis is performed using recombinant, EGFR-Fc captured on anti-human antibody surface and solution-phase analyte (PEGylated clone) in order to determine binding kinetics and binding affinities of PEGylated variants.

Example 20

Evaluation of EGFR Binding Clones for Antiproliferative Activity in an EGFR-Dependent Cell Line Clones were evaluated for antiproliferative activity in the DiFi colon carcinoma cell line, which depends on EGFR signaling for growth. A primary screen was carried out at 10 µM and 1 µM in duplicate to identify active clones. An active clone demonstrated greater than 50% inhibition at either concentration and preferably exhibited a dose response. Active clones were followed up with $IC_{50}$ determinations by testing serial dilutions at eight concentrations in triplicate. The main assay method measured incorporation of $^3$H-thymidine into newly synthesized DNA, but a metabolic detection assay was occasionally used as well that measured conversion of a water soluble tetrazolium salt to a colored byproduct. Standard compounds were included in each experiment to verify assay performance and reproducibility.

Using the $^3$H-thymidine incorporation assay in DiFi cells, clone 679F09 mildly inhibited proliferation in one experiment, yet failed to inhibit proliferation in two separate experiments.

Example 21

Generation of EGFR/IGF-IR PEGylated Bispecific Molecules

Bispecific molecules directed to both EGFR and IGF-1R are created by linking together fibronectin based scaffold domain clones specific to each target using a bifunctional PEG molecule. A cysteine residue is substituted at the C-terminus of each clone so that the bifunctional PEG can link the two clones through maleimide chemistry.

In the present example, the IGF-IR binding clone represented in SEQ ID NO: 203 and the EGFR binding clone represented in SEQ ID NO: 231 are utilized. One of two approaches is used to generate the appropriate bispecific molecule. Equimolar mixtures of the EGFR clone, the IGF-IR clone, and maleimide-PEG-X-kDa-maleimide are mixed for the appropriate period of time and the products are separated by ion-exchange chromatography under pH conditions optimum for the separation of the two isolated clones based upon differences in pI. The theoretical products and their ratios from this separation are 1 part homospecific EGFR, 1 part homospecific IGF-IR, and 2 parts bispecific EGFR/IGF-IR. A second approach is predicated upon the sequential addition of species to PEG-linker. An excess of linker, for example a 10-fold excess, is added to the one of the species and the reaction allowed to proceed to completion. The PEGylated mono-species is recovered from PEG-linked homodimer and unreacted PEG-linker by ion-exchange chromatography. The isolated PEGylated mono-species is then reacted with an equimolar quantity of the other clone species to create the bispecific molecule.

Example 22

Generation of EGFR/VEGFR2 PEGylated Bispecific Molecules

Bispecific molecules directed to both EGFR and VEGFR2 are created by linking together fibronectin based scaffold domain clones specific to each target using a bifunctional PEG molecule. A cysteine residue is substituted at the C-terminus of each clone so that the bifunctional PEG can link the two clones through maleimide chemistry.

In the present example, the VEGFR2 binding clone represented in SEQ ID NO: 128 and the EGFR binding clone represented in SEQ ID NO: 231 are utilized. One of two approaches is used to generate the appropriate bispecific molecule. Equimolar mixtures of the EGFR clone, the VEGFR2 clone, and maleimide-PEG-X-kDa-maleimide are mixed for the appropriate period of time and the products are separated by ion-exchange chromatography under pH conditions optimum for the separation of the two isolated clones based upon differences in pI. The theoretical products and their ratios from this separation are 1 part homospecific EGFR, 1 part homospecific VEGFR2, and 2 parts bispecific EGFR/VEGFR2. A second approach is predicated upon the sequential addition of species to PEG-linker. An excess of linker, for example a 10-fold excess, is added to the one of the species and the reaction allowed to proceed to completion. The PEGylated mono-species is recovered from PEG-linked homodimer and unreacted PEG-linker by ion-exchange chromatography. The isolated PEGylated mono-species is then reacted with an equimolar quantity of the other clone species to create the bispecific molecule.

Example 23

Generation of EGFR/EGFR PEGylated Bispecific Molecules

Bidomain molecules directed to EGFR are created by linking together fibronectin based scaffold domain clones specific to EGFR using a bifunctional PEG molecule. A cysteine residue is substituted at the C-terminus of each clone so that the bifunctional PEG can link the two clones through maleimide chemistry.

In the present example, the EGFR binding clone represented in SEQ ID NO: 231 is utilized. A 2:1 ration of the EGFR clone and maleimide-PEG-X-kDa-maleimide are mixed for the appropriate period of time and the products are separated by ion-exchange chromatography. The theoretical products and their ratios from this separation are 2 parts homospecific EGFR and 2 parts EGFR/EGFR.

Example 24

Generation of EGFR/IGF-IR Polypeptide-Linked Bispecific Molecules

Bispecific molecules directed to both EGFR and IGF-IR are created by connecting the two clones via a polypeptide linker. The orientation of the two clones with regards to the N-terminal clone versus the C-terminal clone is arbitrary, but in the present example, the EGFR clone is in the N-terminal position. In the present example, the EGFR binding clone represented in SEQ ID NO: 215 and the IGF-IR binding clone represented in SEQ ID NO: 236 are utilized.

Hence the DNA construct in the present example is EGFR binding clone-polypeptide linker-IGFR binding clone. This is expressed in *E. coli* and purified per usual either from inclusion bodies or from the soluble fraction.

Example 25

Generation of EGFR/VEGFR2 Polypeptide-Linked Bispecific Molecules

Bispecific molecules directed to both EGFR and VEGFR2 are created by connecting the two clones via a polypeptide linker. The orientation of the two clones with regards to the N-terminal clone versus the C-terminal clone is arbitrary, but in the present example, the EGFR clone is in the N-terminal position. In the present example, the EGFR binding clone represented in SEQ ID NO: 215 and the VEGFR2 binding clone represented in SEQ ID NO: 129 are utilized.

Hence the DNA construct in the present example is EGFR binding clone-polypeptide linker-VEGFR binding clone. This is expressed in *E. coli* and purified per usual either from inclusion bodies or from the soluble fraction.

Example 28

Generation of EGFR/EGFR Polypeptide-Linked Bispecific Molecules

Bisdomain molecules directed to EGFR are created by connecting the two clones via a polypeptide linker. In the present example, the EGFR binding clone represented in SEQ ID NO: 215 is utilized. Hence the DNA construct in the present example is EGFR binding clone-polypeptide linker-EGFR binding clone. This is expressed in *E. coli* and purified per usual either from inclusion bodies or from the soluble fraction.

Material and Methods Used Herein

The following materials and methods were used for the experiments described in the Examples.

Recombinant Proteins:

EGFR-Fc (R&D Systems, Minneapolis, Minn.) consisting of the ectodomain of human EGFR as a Fc fusion was purchased and shown to be functional for EGF binding by Biacore. The first 525 amino acids of the human EGFR extracellular domain was cloned into a mammalian expression vector containing the hinge and constant regions of human IgG1. Transient transfection of the plasmid produced a fusion protein, EGFR 525-Fc, which was subsequently purified by Protein A chromatography. This protein was shown to be capable of binding EGF using a similar Biacore assay as was done for the full length ectodomain fusion.

Primers:

The following oligonucleotides were prepared by chemical synthesis for eventual use in library construction and mutagenesis of selected clones.

T7TMV:
(SEQ ID NO: 237)
5'-TAA TAC GAC TCA CTA TAG GGA CAA TTA CTA TTT ACA ATT ACA ATG-3'

FnAB:
(SEQ ID NO: 238)
5'-GGG ACA ATT ACT ATT TAC AAT TAC AAT GGT TTC TGA TGT GCC GCG CGA CCT GGA AGT GGT TGC TGC CAC CCC CAC CAG CCT GCT GAT CAG CTG G-3'

FnBC:
(SEQ ID NO: 239)
5'-AGC CTG CTG ATC AGC TGG NNS NNS NNS NNS NNS NNS NNS CGA TAT TAC CGC ATC ACT-3'

FnBC8:
(SEQ ID NO: 240)
5'-AGC CTG CTG ATC AGC TGG NVH NVHNVH NVH NVH NVH NVH NVH TAT TAC CGC ATC ACT-3'

FnBC (trimer):
(SEQ ID NO: 241)
5'-AGC CTG CTG ATC AGC TGG X X X X X X X CGA TAT TAC CGC ATC ACT-3' to construct a BC loop using trimer phosphoramidites FnCD:
(SEQ ID NO: 242)
5'-AGG CAC AGT GAA CTC CTG GAC AGG GCT ATT GCC TCC TGT TTC GCC GTA AGT GAT GCG GTA ATA TCG-3'

FnDE:
(SEQ ID NO: 243)
5'-CAG GAG TTC ACT GTG CCT NNS NNS NNS NNS ACA GCT ACC ATC AGC GGC-3'

FnDE (trimer):
(SEQ ID NO: 244)
5'-CAG GAG TTC ACT GTG CCT X X X X ACA GCT ACC ATC AGC GGC-3' to construct a DE loop using trimer phosphoramidites FnEF:
(SEQ ID NO: 245)
5'-AGT GAC AGC ATA CAC AGT GAT GGT ATA ATC AAC GCC AGG TTT AAG GCC GCT GAT GGT AGC TGT-3'

FnFG6:
(SEQ ID NO: 246)
5'-ACT GTG TAT GCT GTC ACT NNS NNS NNS NNS NNS NNS CCA ATT TCC ATT AAT TAC-3' to give an FG loop with 6 random amino acids.

FnFG6 (trimer):
(SEQ ID NO: 247)
5'-ACT GTG TAT GCT GTC ACT X X X X X X CCA ATT TCC ATT AAT TAC-3' to give an FG loop with 6 random amino acids using trimer phosphoramidites.

FnFG8:
(SEQ ID NO: 248)
5'-ACT GTG TAT GCT GTC ACT NNS NNS NNS NNS NNS NNS NNS NNS CCA ATT TCC ATT AAT TAC-3' to give an FG loop with 8 random amino acids.

-continued

FnFG8 (trimer):
(SEQ ID NO: 249)
5'-ACT GTG TAT GCT GTC ACT X X X X X X X X CCA
ATT TCC ATT AAT TAC-3' to give an FG loop with 8
random amino acids using trimer phosphoramidites FnFG10:
(SEQ ID NO: 250)
5'-ACT GTG TAT GCT GTC ACT NNS NNS NNS NNS
NNS NNS NNS NNS NNS CCA ATT TCC ATT AAT TAC-3'
to give an FG loop with 10 random amino acids.

FnFG10:
(SEQ ID NO: 251)
5'-ACT GTG TAT GCT GTC ACT X X X X X X X X X X
CCA ATT TCC ATT AAT TAC-3' to give an FG loop
with 10 random amino acids using trimer
phosphoramidites.

FnFG12:
(SEQ ID NO: 252)
5'-ACT GTG TAT GCT GTC ACT NNS NNS NNS NNS NNS
NNS NNS NNS NNS NNS NNS CCA ATT TCC ATT AAT
TAC-3' to give an FG loop with 12 random amino
acids.

FnFG14:
(SEQ ID NO: 253)
5'-ACT GTG TAT GCT GTC ACT NNS NNS NNS NNS NNS
NNS NNS NNS NNS NNS NNS NNS NNSCCA ATT TCC
ATT AAT TAC-3' to give an FG loop with 14 random
amino acids.

FnG:
(SEQ ID NO: 254)
5'-TTA AAT AGC GGA TGC CTT GTC GTC GTC GTC CTT
GTA GTC TGT GCG GTA ATT GGA AAT TGG-3'

FLAG:
(SEQ ID NO: 255)
5'-TTT TTT TTT TTT TTT TTT TTA AAT AGC GGA TGC
CTT GTC GTC GTC GTC CTT GTA-3'

679F09BC:
(SEQ ID NO: 256)
5'-AGC CTG CTG ATC AGC TGG CAG GTT CCG CGT CCG
ATG TAC CAA TAT TAC CGC ATC ACT TAC-3'

679F09DE:
(SEQ ID NO: 257)
5'-CAG GAG TTC ACT GTG CCT GGT GGT GTT CGT ACA
GCT ACC ATC AGC GGC-3'

679F09FG:
(SEQ ID NO: 258)
5'-ACT GTG TAT GCT GTC ACT GAC TAC ATG CAT TCT
GAA TAC CGT CAG TAC CCA ATT TCC ATT AAT TAC-3'

FnCD':
(SEQ ID NO: 259)
5'-AGG CAC AGT GAA CTC CTG GAC AGG GCT ATT GCC
TCC TGT TTC GCC GTA AGT GAT GCG GTA ATA-3'

FnB:
(SEQ ID NO: 260)
5'-AGC CTG CTG ATC AGC TGG-3'

FnD:
(SEQ ID NO: 261)
5'-CAG GAG TTC ACT GTG CCT-3'

FnF:
(SEQ ID NO: 262)
5'-ACT GTG TAT GCT GTC ACT-3'

Primary Library Construction:

A diverse library was constructed by extension of the overlapping synthetic oligonucleotides listed above, using KOD polymerase (EMD Biosciences, San Diego, Calif.). In these oligonucleotide designations, "N" indicates a mixture of A, C, G and T; "V" indicates a mixture of A, C and G, "H" indicates a mixture of A, C and T, and "S" indicates a mixture of C and G. Loop definitions are identical to those described previously (Xu et al, 2002). The BC loop was constructed by extension of 50 pmol FnBC with 100 pmol FnCD in a 100 µl KOD reaction that was supplemented with 1 M Betaine and 3% DMSO. The reaction was taken through 10 temperature cycles of 30s at 94° C., 30s at 52° C. and 1 min at 68° C. to ensure complete extension of the fragments. The DE and FG loops were constructed in a similar manner, using 200 pmol FnDE with 100 pmol FnEF for the DE loop and 100 pmol FnFG10 with 200 pmol FnG for the FG loop. Following extension of the 3 individual loops, the DE and FG loops were combined and extended together for an additional 10 temperature cycles of 30s at 94° C., 30s at 52° C. and 1 min at 68° C. The BC loop was extended with 100 pmol FnAB in the same manner. The DE/FG mixture and the BC loop were each diluted 10-fold with fresh KOD reagents and extended with FLAG and T7TMV respectively, for 10 temperature cycles 30s at 94° C., 30s at 52° C. and 1 min at 68° C. Finally the fragments were combined and extended together for 10 temperature cycles of 30s at 94° C., 30s at 52° C. and 1 min at 68° C. This produced a library with 7 random amino acids in the BC loop, 4 random amino acids in the DE loop, and 10 random amino acids in the FG loop. Additional libraries were constructed with different FG loop lengths by using oligonucleotides FnFG6, FnFG8, FnFG12 or FnFG14 instead of FnFG10. The libraries containing FG loop lengths between 6 and 14 amino acids were combined to give the "NNS" library.

The "NVH" and "WFC" libraries were made using the same method, except that oligonucleotides FnBC, FnDE and FnFG were replaced with FnBC (trimer), FnDE (trimer) and FnFG (trimer) respectively. In these oligonucleotides, X denotes a mixture of trimer phosphoramidites (Glen Research, Sterling, Va.) that encode 13 amino acids for the "NVH" library (Lys, Asn, Thr, Gln, His, Pro, Arg, Glu, Asp, Ala, Gly, Tyr, Ser) or 17 amino acids for the "-WFC" library (Lys, Asn, Thr, Gln, His, Pro, Arg, Glu, Asp, Ala, Gly, Tyr, Ser, Leu, Ile, Met, Val).

RNA-Protein Fusion Production:

Double-stranded DNA libraries were converted into RNA-protein fusions (PROfusion™) essentially as described (Xu et al, 2002, Kurz et al, Nuc. Acid Res. 28:83, 2000). Briefly, the DNA library was transcribed using an in vitro transcription kit (MEGAscript™, Ambion, Austin, Tex.) and the resulting RNA was desalted by size exclusion chromatography on a NAP-5 column (GE Healthcare). 2 nmol RNA was crosslinked by irradiation at 314 nM for 20 min in 200 µl of a solution containing 150 mM NaCl, 10 mM Tris-HCl (pH8) and a 1.5-fold excess of puromycin-containing linker (5'-Pso u agc gga ugc XXX XXX CC Pu-3' (Pu=puromycin, Pso=C6-psoralen, u, a, g, c=2'-OMe-RNA, X=9-atom PEG spacer.))

The mRNA-puromycin molecules were then translated in 3 ml rabbit reticulocyte lysate (Ambion, Austin, Tex.). The resulting mRNA-protein fusions were purified using oligo dT cellulose (GE Healthcare) and reverse-transcribed using 2 nmol of the primer FLAG and superscript II reverse transcriptase (Invitrogen) according to the manufacturers instructions.

The cDNA/mRNA-protein fusions were purified by M2 Flag agarose (Sigma, St Louis, Mo.) and quantitated by PCR. This gave a purified library of approximately $10^{12}$ full length clones that were amplified by PCR using primers T7TMV and FLAG for use in subsequent PROfusion™ experiments.

Affinity Selection for Binding to EGFR:

Human IgG (Sigma) was coated on protein G-coated magnetic beads (Invitrogen) to produce a negative selection matrix. The RNA-protein fusion library was mixed with the negative selection matrix to remove clones that bind to protein G or the Fc region of the target. The beads were separated on a magnet and the unbound fraction was collected and added to 100 nM EGFR-Fc in PBS with 0.05% Tween 20 and 1 mg/ml BSA (Ambion). After 30 min, the bound proteins were captured on Protein G-coated magnetic beads and were washed 6 times using a Kingfisher magnetic particle processor (Thermo Electron, Waltham, Mass.). The cDNA was eluted in 100 mM KOH, was neutralized with 100 mM Tris-HCl, and was amplified by PCR to generate a second-generation library enriched in molecules that bound EGFR. The consecutive processes of amplification, synthesis of RNA-protein fusions, and affinity selection were carried out a total of 5 times and the bound molecules were quantitated by PCR. The binding populations obtained after rounds 4 and 5 were amplified and ligated by recombination (InFusion™, Clontech, Mountain View, Calif.) into an E. coli expression vector containing a promoter for T7 RNA polymerase and an in-frame His$_6$ tag. The ligated mixture was transformed into E. coli strain BL21 (DE3) pLysS (Invitrogen) that expresses T7 RNA polymerase upon induction with IPTG, thereby giving inducible protein expression.

Construction of Single-Loop Randomized Libraries from Clone 679F09

Three libraries were constructed in which single loops were replaced with random sequence. The libraries were constructed at the DNA level by overlap extension with KOD polymerase as described above, except that random sequences in two out of three loops were replaced with fixed sequence corresponding to clone 679F09. The fixed sequences were provided in the BC loop by oligonucleotide 679F09BC, and in the DE loop by oligonucleotide 679F09DE, and in the FG loop by oligonucleotide 679F09FG. These replaced the corresponding random oligonucleotides FnBC, FnDE, or FnFG10 during library construction. Randomization of position XX necessitated the use of primer FnCD' in place of FnCD, and FnBC8 in place of FnBC. In addition, the use of "NVH" codons removed hydrophobic amino acids from the library.

The library in which the BC loop from clone 679F09 was replaced by random amino acids was made by assembling the oligonucleotides: T7TMV+FnAB+FnBC8+FnCD'+679F09DE+FnEF+679F09FG+FnG+FLAG as described above. The library in which the DE loop from clone 679F09 was replaced by random amino acids was made by assembling the oligonucleotides: T7TMV+FnAB+679F09BC+FnCD'+FnDE (trimer)+FnEF+679F09FG+FnG+FLAG. The library in which the FG loop from clone 679F09 was replaced by random amino acids was assembled from the oligonucleotides: T7TMV+FnAB+669F09BC+FnCD'+679F09+FnEF+FnFG10 (trimer)+FnG+FLAG.

Construction of 3-Loop Randomized Libraries from Clone 679F09

The three single-loop libraries derived from clone 679F09 were subjected to PROfusion™ selection as described above. The surviving clones in each library contained 2 loops from the parent clone and 1 loop from the random sequence that was compatible with binding of each clone. The three random loops, one from each library, were amplified using oligonucleotide primers that bound the surrounding scaffold regions. The BC loop was amplified from the library containing the variable BC loop using oligonucleotide primers FnB and FnCD'. The DE loop was amplified from the library containing the variable DE loop using oligonucleotide primers FnD and FnEF. The FG loop was amplified from the library containing the variable FG loop using oligonucleotide primers FnF and FnG. The three excised loops were purified by agarose gel electrophoresis, mixed in equal proportions and amplified by KOD polymerase with primers FnAB and FnG followed by T7TMV and FLAG.

Optimization of Clones Containing 3 Random Loops:

The 3-loop randomized library was taken through cycles of amplification, synthesis of RNA-protein fusions, and affinity selections as described above. EGFR-Fc was used at decreasing concentrations to select for the highest affinity binders. After 4 rounds, the resulting protein populations were cloned into E. coli for analysis as described above.

Direct Binding ELISA for EGFR

The protein populations resulting from the above selections are expressed in E. coli as His6 tagged proteins. The direct binding ELISA relies on the oriented capture of His6 tagged clones onto anti-His monoclonal antibody plates (EMD Biosciences, San Diego, Calif.) blocked with casein block buffer (Pierce, Rockford, Ill.) for 1-2 hrs. Typically a 1:50 dilution of HTPP material (0.2-2 ug) is captured for 1 hr, followed by incubation with 50 nM of the EGFR-Fc targets. Bound EGFR-Fcs are detected by incubation with anti-human HRP. Bound HRP conjugate is detected using the colorimetric substrate TMB (BD Biosciences, San Jose, Calif.) following the manufacturer's instructions.

Cell-Based Competitive Ligand Binding Assay

The clones resulting from the above selections are assayed in the Cell-Based Competitive Ligand Binding Assay to determine if the clones are competitive with EGF, the natural ligand, for binding to the EGFR located on the surface of cells. Human epithelial carcinoma cells, clone A431, which express large numbers of EGFRs on the cell surface, are plated into 96 well tissue culture plates and allowed to adhere for 48 hours. The cells are washed with serum free media and dilutions of the selected clones are incubated with the cells for 15 minutes, 37° C. in a humidified incubator in 5% $CO_2$. This incubation allows binding of the clone to the EGFR on the cell surface. Europium labeled EGF (Eu-EGF) at a final concentration of 10 nM is then added to the cells and incubated for an additional 3 hours at 4° C. After incubation, the cells are washed with cold PBS to remove unbound clones and Eu-EGF and 50 ul of Enhancement Solution (Perkin Elmer) is added to the cells and incubated for 45 mins at 37° C. This step dissociates the europium label from the EGF ligand producing a fluorescent signal which is measured by time resolved fluorescence. The intensity of the signal is correlated with the amount of Eu-EGF bound to the cell's surfaces. A dose response decrease in signal intensity indicates that a given clone competes with the europium labeled natural EGF ligand for binding to the EGFR.

High Throughput Protein Production (HTPP):

Selected binders cloned into pDEST-14 vector and transformed into E. coli BL21 (DE3) pLysS cells are inoculated in 5 ml LB medium containing 50 μg/mL carbenicillin and 34 μg/mL chloromphenicol in a 24-well format and grown at 37° C. overnight. Fresh 5 ml LB medium (50 μg/mL carbenicillin and 34 μg/mL chloromphenicol) cultures are prepared for inducible expression by aspirating 200 μl from the overnight culture and dispensing it into the appropriate well. The cultures are grown at 37° C. until $A_{600}$ 0.6-1.0. After induction with 1 mM isopropyl-β-thiogalactoside (IPTG) the culture is grown for another 4 hours at 30° C. and harvested by centrifugation for 30 minutes at 3220 g at 4° C. Cell Pellets are frozen at −80° C.

Cell pellets (in 24-well format) are lysed by resuspension in 450 µl of Lysis buffer (50 mM $NaH_2PO_4$, 0.5 M NaCl, 1× Complete™ Protease Inhibitor Cocktail-EDTA free (Roche), 1 mM PMSF, 10 mM CHAPS, 40 mM Imidazole, 1 mg/ml lysozyme, 30 ug/ml DNAse, 2 ug/ml aprotonin, pH 8.0) and shaken at room temperature for 1 hour. Lysates are clarified and re-racked into a 96-well format by transfer into a 96-well Whatman GF/D Unifilter fitted with a 96-well, 650 µl catch plate and are centrifuged for 5 minutes at 200 g. The clarified lysates are transferred to a 96-well Ni-Chelating Plate that has been equilibrated with equilibration buffer (50 mM $NaH_2PO_4$, 0.5 M NaCl, 10 mM CHAPS, 40 mM Imidazole, pH 8.0) and is incubated for 5 min. Unbound material is removed by vacuum. The resin is washed 2×0.3 ml/well with Wash buffer #1 (50 mM $NaH_2PO_4$, 0.5 M NaCl, 5 mM CHAPS, 40 mM Imidazole, pH 8.0) with each wash removed by vacuum. Next the resin is washed with 3×0.3 ml/well with PBS with each wash step removed by vacuum. Prior to elution each well is washed with 50 µl Elution buffer (PBS+20 mM EDTA), incubated for 5 min and this wash is discarded by vacuum. Protein is eluted by applying an additional 100 ul of Elution buffer to each well. After a 30 minute incubation at room temperature the plate(s) are centrifuged for 5 minutes at 200 g and eluted protein is collected in 96-well catch plates containing 5 µl of 0.5M $MgCl_2$ affixed to the bottom of the Ni-plates. Eluted protein is quantified using a BCA assay with lysozyme as the protein standard.

Midscale Expression and Purification of Soluble Fibronectin-Based Scaffold Protein Binders:

For expression, selected clone(s), followed by the $His_6$ tag, are cloned into a pET9d (EMD Biosciences, San Diego, Calif.) vector and are expressed in E. coli BL21 (DE3) pLysS cells. Twenty ml of an inoculum culture (generated from a single plated colony) is used to inoculate 1 liter of LB medium containing 50 µg/mL carbenicillin and 34 µg/mL chloromphenicol. The culture is grown at 37° C. until $A_{600}$ 0.6-1.0. After induction with 1 mM isopropyl-β-thiogalactoside (IPTG) the culture is grown for 4 hours at 30° C. and is harvested by centrifugation for 30 minutes at ≥10,000 g at 4° C. Cell Pellets are frozen at −80° C. The cell pellet is resuspended in 25 mL of lysis buffer (20 mM $NaH_2PO_4$, 0.5 M NaCl, 1× Complete™ Protease Inhibitor Cocktail-EDTA free (Roche), 1 mM PMSF, pH 7.4) using an Ultra-turrax homgenizer (IKA works) on ice. Cell lysis is achieved by high pressure homongenization (≥18,000 psi) using a Model M-110S Microfluidizer (Microfluidics). The soluble fraction is separated by centrifugation for 30 minutes at 23,300 g at 4° C. The supernatant is clarified via 0.45 µm filter. The clarified lysate is loaded onto a HisTrap column (GE) pre-equilibrated with 20 mM $NaH_2PO_4$, 0.5 M NaCl, pH 7.4. The column is then washed with 25 column volumes of 20 mM $NaH_2PO_4$, 0.5 M NaCl, pH 7.4, followed by 20 column volumes of 20 mM $NaH_2PO_4$, 0.5 M NaCl, 25 mM imidazole pH 7.4, and then 35 column volumes of 20 mM $NaH_2PO_4$, 0.5 M NaCl, 40 mM imidazole pH 7.4. Protein is eluted with 15 column volumes of column volumes of 20 mM $NaH_2PO_4$, 0.5 M NaCl, 500 mM imidazole pH 7.4, fractions are pooled based on absorbance at $A_{280}$ and are dialyzed against 1×PBS, 50 mM Tris, 150 mM NaCl, pH 8.5 or 50 mM NaOAc; 150 mM NaCl; pH4.5. Any precipitate is removed by filtering at 0.22 µm.

PEGylation of EGFR Binding Clones

The EGFR binding clone-PEG40 molecule is prepared by using a 2-fold excess of PEG-40-kDa (NOF Corporation) to the C-version of the clone via maleimide chemistry. The reaction is allowed to proceed at room temperature for 2.5 hours. Free PEG-40 is separated from clone-PEG-40 by Cation Exchange Chromatography (SP-HiTrap; GE). The reaction mixture is diluted 1:10 with 20 mM $NaH_2PO_4$, pH 6.7 and is applied to an SP-HiTrap column pre-equilibrated with Equilibration buffer (20 mM $NaH_2PO_4$, 10 mM NaCl, pH 6.7), washed with Equilbration buffer and is eluted using 20 mM $NaH_2PO_4$, 0.5M NaCl, pH 6.7. Eluted fractions are pooled based on SDS-PAGE analysis. The SP-pooled eluate is buffer exchanged via G25 Chromatography (GE) into PBS.

The PEG20-EGFR binding clone-PEG20 is prepared by using a 2-fold excess of purified clone-C to PEG-20-kDa (NOF Corporation) via maleimide chemistry. The reaction is carried out at room temperature for 1 hour. Unpegylated protein is separated from the PEG20-clone-PEG20 by SEC Chromatography (Superose 6; GE) in 20 mM $NaH_2PO_4$, 10 mM NaCl, pH 6.7 buffer. The fractions containing the PEG20-clone-PEG20 are pooled and are further purified to removed mono-pegylated clone. This is achieved by cation exchange chromatography (SP; GE). A SP-HiTrap column is pre-equilibrated with Buffer A (20 mM $NaH_2PO_4$, 10 mM NaCl, pH 6.7), the SEC eluate is applied, the column is then washed with buffer A, and then a gradient from 0-10% buffer B (20 mM $NaH_2PO_4$, 1.0M NaCl, pH 6.7) over 5 column volumes and held for an additional 5 column volumes is run. PEG20-clone-PEG20 is eluted from the SP-column by eluting with 50% Buffer B. Fractions are pooled by A280 and buffer exchanged into PBS by G25 Chromatography (GE).

BIAcore Analysis of the Soluble Fibronectin-Based Scaffold Proteins:

The binding kinetics of fibronectin-based scaffold proteins binding proteins to the target is measured using Biacore 3000 or T100 biosensors (GE Healthcare, Piscataway, N.J.). Anti-human antibody (GE Healthcare, Piscataway, N.J.) is directly immobilized on Flow cells 1 and 2 (Fc1 and Fc2) of Biasensor CM5 chip following the manufacturer's instructions. The kinetic analysis involves the capture of EGFR-Fc (R&D Systems, Minneapolis, Minn.) or the in-house generated truncated EGFR 525-Fc on anti-human IgG on Fc2 followed by injection of the clone in solution on Fc1 and Fc2. The anti-human antibody surface is regenerated by 2 successive injections of 3M $MgCl_2$. Sensorgrams are obtained at each concentration and are evaluated using the manufacturer's program Biaevaluation or Biacore T100 software, to determine the rate constants $k_a$ ($k_{on}$) and $k_d$ ($k_{off}$). The dissociation constant, $K_D$ is calculated from the ratio of rate constants $k_{off}/k_{on}$. Typically, a concentration series (0 µM to 2 µM) of purified clone diluted in the running buffer HBS-EP (10 mM Hepes 150 mM NaCl 3 mM EDTA 0.05% Surfactant P20) is evaluated for binding to anti-human IgG captured human EGFR-Fc fusion protein.

For experiments determining binding to other related family member such as HER2 or HER3, recombinant ectodomain-Fc fusions are captured using anti-human IgG antibody as described above. Specific binding to either human EGFR, or other related family members such as HER2 or HER3 is calculated by subtracting the binding observed to the blank reference flow cell 1. VEGFR2-Fc, a non-related receptor, serves as an additional non-specific binding reference. EGFR binding clones are diluted to 10 µM in HBS-EP (10 mM Hepes 150 mM NaCl 3 mM EDTA 0.05% Surfactant P20) and are injected at 20 uL/min for 5 minutes over the flow cells at 25 C and dissociation is observed over 10 mins.

Differential Scanning Calorimetry:

Differential Scanning calorimetry (DSC) analysis of mid-scaled clones is performed to determine thermal stability. A 1 mg/ml solution of appropriate clone is scanned in a N-DSC II calorimeter (calorimetry Sciences Corp) by ramping the temperature from 5° C. to 95° C. at a rate of 1 degree per minute under 3 atm pressure. The data is analyzed vs. a control run of the appropriate buffer using a best fit using Orgin Software (OrginLab Corp).

Size-Exclusion Chromatography:

Size-exclusion chromatography (SEC) is performed using a TSKgel Super SW2000 column (TOSOH Biosciences, LLC), 4.6 mm×30 cm, on an Agilent 1100 HPLC system with UV detection at A214 nm and A280 nm and with fluorescence detection (excitation=280 nm, emission=350 nm). A buffer of 100 mM sodium sulfate, 100 mM sodium phosphate, 150 mM sodium chloride, pH 6.8 at a flow rate of 100 µL/min is employed. Samples (0.1 to 1 µg each) at a concentration of approximately 100 µg/mL are injected separately. Gel filtration standards (Bio-Rad Laboratories, Hercules, Calif.) are used for molecular weight calibration.

SEC MALLS Analysis of Clones:

Size Exclusion Chromatography (SEC) is performed on a Waters Breeze HPLC system equipped with a Waters 2487 UV detector using a Superdex 200 column (GE Healthcare) with a mobile phase of 100 mM Sodium Sulfate, 100 mM Sodium Phosphate, 150 mM Sodium Chloride pH 6.8 applied at a flow rate of 0.6 ml/min. Samples are diluted to approximately 1.0 mg/ml with mobile phase and 50 µl is injected. Multi-Angle Laser Light Scattering (MALLS) analysis is performed using a miniDAWN Light Scattering detector (Wyatt Technology Corporation) and Optilab DSP Differential Refractometer (Wyatt Technology Corporation) plumbed in-line after the UV detector. Analysis of the light scattering data is performed using Astra V version 5.1.9.1 software (Wyatt Technologies Corporation). To calculate the concentration of the clone by absorbance at 280 nm, a theoretical molar extinction coefficient based on amino acid sequence is used. For concentration determination by Refractive Index, an estimated specific refractive index increment (dn/dc) of 0.185 mL/g is used.

MALDI TOF Mass Spectrometry:

EGFR binding clones are analyzed by Matrix Assisted Laser Desorption Ionization Time of Flight (MALDI-TOF) mass spectrometry (FIG. 14) using a Voyager DE PRO mass spectrometer (Applied Biosystems). Samples are diluted to approximately 1.0 mg/ml with 0.1% TFA. Approximately 12 µl of sample is loaded onto a C4 ZipTip (Millipore Corporation) and is washed with 0.1% Trifluoroacetic Acid (TFA) to remove salts and contaminants. Sample is eluted directly from the ZipTip onto the target plate using 2 µl of Sinapinic Acid matrix (10 mg/ml in 70% Acetonitrile, 0.1% TFA). Standardization of the instrument is performed using two proteins of known mass: Cytochrome C (12361.96 Da) and Apomyoglobin (16952.27 Da) prepared to a final concentration of 5 µM in Sinapinic Acid and spotted onto the plate. Spectra are acquired with the following instrument settings: Accelerating Voltage 25000V, Grid Voltage 91%, Guide Wire 0.1%, Extraction Delay Time 400 nsec, Laser Intensity 3824. Raw spectra are processed in Data Explorer v. 4.5 (Applied Biosystems) by applying baseline correction and the Gaussian Smooth algorithm with a filter width value of 9.

$^3$H-Thymidine Cell Proliferation Assay

Cells were plated at 2,500 cells per well in 96-well microtiter plates. Compounds solubilized in PBS were added 24 hours later and the cultures were incubated for an additional 72 hours. Cells were pulsed with 4 uCi/mL [$^3$H] thymidine (Amersham Pharmacia Biotech, Buckinghamshire, United Kingdom) for 3 hours, trypsinized, and harvested onto UniFilter-96, GF/B plates (Perkin-Elmer, Boston, Mass.). Incorporation into DNA was measured by scintillation counting on a TopCount NXT (Packard, Meriden, Conn.). Results are expressed as an $IC_{50}$, which is the drug concentration required to inhibit cell proliferation by 50% to that of untreated control cells. Data are averages of triplicate wells with SEs indicated.

Water Soluble Tetrazolium Salt Proliferation Assay

Cells were seeded in complete media without phenol red and treated with EGFR binding clones as described above. At the end of the treatment period, 10 ul/well of the WST-8 reagent (Dojindo Molecular Technologies, Gaithersburg Md.) was added to each well and the plate was incubated for three hours at 37 degrees in 5% $CO_2$. Accumulation of formazan dye was quantified by reading absorbance at 450 nm on a SpectraMAX Plus (Molecular Devices, Sunnyvale, Calif.).

In Cell Western Assay

Cells were seeded into poly-D-lysine coated microtiter plates (Becton Dickinson, Franklin Lakes, N.J.) at 24,000 cells/well for A431 epidermoid carcinoma or FaDu head & neck carcinoma cells and allowed to adhere overnight. Cells were washed and then incubated for 24 hours in serum free media. Serial dilutions of clones were then applied to the cells and incubated for 4 hours prior to stimulation with 100 ng/ml EGF for 10 minutes. Following stimulation, cells were fixed for 20 minutes in PBS containing 3.7% formaldehyde and then permeabilized in PBS containing 0.1% triton-X-100 for 15 minutes. Cells were blocked for one hour in Odyssey blocker and incubated with antibodies to detect either EGFR phosphorylated on tyrosine 1068 (Cell Signaling, Beverly, Mass.) and actin (Sigma, St. Louis, Mo.) or ERK (MAP kinase phosphorylated on tyrosine 202/threonine 204 and total ERK (Santa Cruz Biotechnology, Santa Cruz, Calif.). After washing three times in PBS containing 0.1% tween-20, secondary antibodies were added (Invitrogen, Carlsbad, Calif. or Rockland, Gilbertsville, Pa.). Cells were washed three times in PBS containing 0.1% tween-20 and imaged on a Li-Cor Odyssey Infrared Imaging System (Li-Cor Biosciences, Lincoln, Nebr.). Each clone was assayed in triplicate and $IC_{50}$ values were calculated from linear regression analysis of percent inhibition of maximum signal minus background.

Epitope Mapping by Blocking EGFR Antibodies

A431 cells were seeded into poly-D-lysine coated microtiter plates at 24,000 cells/well and allowed to adhere overnight. The next day each well was washed once with cold PBS and cells were preincubated with various concentrations of clones for 1 hour at 4° C. Unbound protein was washed away with cold PBS and bound protein was cross-linked to the receptor by treating with 1 mM BS3 in PBS pH=8.0 at 4° C. for 1 hour. The contents of the plate were dumped and the crosslinking reaction was quenched by adding 50 ul per well of 50 mM Tris-HCl pH=7.5 and incubating for 15 minutes at room temp. The plate was washed once in PBS+0.1% tween-20 and fixed for 20 minutes in PBS+3.7% formaldehyde. The plate was blocked in Odyssey blocker for 1 hour at room temp. Blocking solution was removed and various primary antibodies diluted 1:100 or 1:50 in Odyssey blocker were added to the plate and incubated for 1 hour at room temp. The plate was washed three times and secondary antibodies diluted 1:800 in Odyssey blocker+0.2% Tween-20 along with TOPRO3 counterstain 1:3000 were added to the plate and incubated for 1 hour at room temp. The plate was washed three times and imaged on a Li-Cor Odyssey infrared imaging system at 160 uM resolution.

ELISA Assay for Determination of Total EGFR Phosphotyrosine Levels in DiFi Cells Inhibition of EGF-stimulated EGFR phosphorylation was determined by plating $1\times10^5$ DiFi cells in each well of a microtiter plate and allowing them to adhere overnight. The next day, media was replaced with serum free media and cells were starved for 16 hours. EGFR binding clones or control antibodies were incubated with cells at 37° C. for 4 hours. Cells were then stimulated with 20 ng/ml of EGF for 10 minutes and cell lysates were prepared in HNTG [50 mM Hepes, 150 mM NaCl, 0.5% triton-X-100, 8% glycerol, 2 mM $Na_3PO_4$, 1.5 mM $MgCl_2$, 1 mM EDTA containing the protease inhibitors AEBSF, aprotinin, leupeptin, bestatin, pepstatin-A and E64]. Lysates were transferred to a capture plate coated with a primary antibody specific for the human extracellular domain of the EGF receptor (Cell Signaling, Beverly, Mass.). The detection antibody was replaced with a mouse monoclonal antiphosphotyrosine antibody conjugated to horseradish peroxidase (4G10, Upstate Biotechnology, Lake Placid, N.Y.). The chromogenic substrate, tetramethylbenzidine, was used to measure the absorbance on a spectrophotometer at 450 nm. Samples were tested in triplicate and $IC_{50}$ values were determined by subtracting background and calculating percent inhibition of total maximum signal in each assay.

The invention claimed is:

1. A nucleic acid encoding a polypeptide comprising a tenth fibronectin type III ($^{10}$Fn3) domain, wherein the $^{10}$Fn3 domain (i) comprises an AB loop, a BC loop, a CD loop, a DE loop, an EF loop, and an FG loop, wherein the amino acid sequences of the BC, DE, and FG loops are identical to the amino acid sequences of the respective BC, DE, and FG loops of a $^{10}$Fn3 domain with an amino acid sequence selected from the group consisting of SEQ ID NOs: 207-231; and (ii) binds human epidermal growth factor receptor (EGFR) with a dissociation constant of less than $10^{-4}$M.

2. The nucleic acid of claim 1, wherein the $^{10}$Fn3 domain binds human EGFR with a dissociation constant of less than $10^{-6}$ M.

3. The nucleic acid of claim 1, wherein the polypeptide further comprises one or more pharmacokinetic (PK) moieties selected from: a polyoxyalkylene moiety, a human serum albumin binding protein, sialic acid, human serum albumin, IgG, an IgG binding protein, transferrin, and an Fc fragment.

4. The nucleic acid of claim 3, wherein the PK moiety and the $^{10}$Fn3 domain are operably linked via a polypeptide comprising the amino acid sequence of SEQ ID NOs: 232-235.

5. The nucleic acid of claim 1, wherein the polypeptide further comprises a second domain selected from: an antibody moiety; a derivative of lipocalin; a derivative of tetranectin; an avimer; a derivative of ankyrin; and a second fibronectin type III (Fn3) domain, wherein the second domain binds to a human protein, and wherein the second Fn3 domain (i) comprises an AB loop, a BC loop, a CD loop, a DE loop, an EF loop, and an FG loop; (ii) has at least one loop selected from loop BC, DE, and FG with a randomized amino acid sequence relative to the sequence of the corresponding loop of the human Fn3 domain; and (iii) binds a human protein that is not bound by the human Fn3 domain.

6. The nucleic acid of claim 5, wherein the second domain is a second Fn3 domain, and wherein the second Fn3 domain binds the human protein with a dissociation constant of less than $10^{-4}$ M.

7. The nucleic acid of claim 5, wherein the second domain is a second Fn3 domain, and wherein the second Fn3 domain is a tenth fibronectin type III domain ($^{10}$Fn3).

8. The nucleic acid of claim 7, wherein the second $^{10}$ Fn3 domain comprises a polypeptide selected from:
    (i) a polypeptide comprising the amino acid sequence of any of one of SEQ ID NOs: 2-231 and 236; and
    (ii) a polypeptide comprising the amino acid sequence at least 90% identical to any of one of SEQ ID NOs: 2-231 and 236.

9. The nucleic acid of claim 5, wherein the polypeptide inhibits the binding of transforming growth factor alpha (TGF-alpha) or epidermal growth factor (EGF) to EGFR and does not activate human EGFR at sub $IC_{50}$ concentrations in a cell-based assay.

10. The nucleic acid of claim 1, wherein the polypeptide has been deimmunized to remove one or more T-cell epitopes.

11. The nucleic acid of claim 1, wherein the polypeptide inhibits total EGF-stimulated phosphotyrosine activation of EGFR with an $IC_{50}$ of less than 10μM.

12. The nucleic acid of claim 1, wherein said polypeptide inhibits AKT phosphorylation with an $IC_{50}$ of less than 10μM.

13. A nucleic acid encoding a polypeptide comprising a tenth fibronectin type III ($^{10}$Fn3) domain, wherein the $^{10}$Fn3 domain (i) comprises an AB loop, a BC loop, a CD loop, a DE loop, an EF loop, and an FG loop; (ii) comprises an amino acid sequence at least 80% identical to any one of SEQ ID NOs: 207-231; and does not comprise an integrin binding motif comprising arginine-glycine-aspartic acid (RGD).

14. The nucleic acid of claim 13, wherein the polypeptide comprises an amino acid sequence at least 90% identical to any one of SEQ ID NOs: 207-231.

* * * * *

```
                        SEQUENCE LISTING

<160> NUMBER OF SEQ ID NOS: 264

<210> SEQ ID NO 1
<211> LENGTH: 94
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Val Ser Asp Val Pro Arg Asp Leu Glu Val Val Ala Ala Thr Pro Thr
1               5                   10                  15

Ser Leu Leu Ile Ser Trp Arg Ala Arg Gln Asn Leu Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Val Leu Pro Asn Thr Ala Thr Ile Ser Gly Leu Lys Pro
    50                  55                  60

Gly Val Asp Tyr Thr Ile Thr Val Tyr Ala Val Thr Val Gly Val Pro
65                  70                  75                  80

Phe Tyr Asp Met Leu Ile Gly Leu Leu Tyr Pro Ile Ser Ile Asn Tyr
                85                  90                  95

Arg Thr
```

```
<210> SEQ ID NO 3
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Val Ser Asp Val Pro Arg Asp Leu Glu Val Val Ala Ala Thr Pro Thr
1               5                   10                  15

Ser Leu Leu Ile Ser Trp Leu Pro Pro Gly Phe Val Ile Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Arg Leu Thr Thr Ala Thr Ile Ser Gly Leu Lys Pro
    50                  55                  60

Gly Val Asp Tyr Thr Ile Thr Val Tyr Ala Val Thr Ser Ser Asn Gly
65                  70                  75                  80

Phe Tyr Ser Lys Ile Leu Ser Leu Trp Trp Pro Ile Ser Ile Asn Tyr
                85                  90                  95

Arg Thr

<210> SEQ ID NO 4
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Val Ser Asp Val Pro Arg Asp Leu Glu Val Val Ala Ala Thr Pro Thr
1               5                   10                  15

Ser Leu Leu Ile Ser Trp Gly Pro His Val Leu Gly Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Trp Glu Arg Thr Ala Thr Ile Ser Gly Leu Lys Pro
    50                  55                  60

Gly Val Asp Tyr Thr Ile Thr Val Tyr Ala Val Thr Leu Arg Thr Gly
65                  70                  75                  80

Leu Pro Thr Leu His Ser Pro Gly Pro Ile Ser Ile Asn Tyr Arg Thr
                85                  90                  95

<210> SEQ ID NO 5
<211> LENGTH: 91
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Val Ser Asp Val Pro Arg Asp Leu Glu Val Val Ala Ala Thr Pro Thr
1               5                   10                  15

Ser Leu Leu Ile Ser Trp Ile Phe Ile Pro Ser Thr Arg Tyr Tyr
            20                  25                  30
```

```
Arg Ile Thr Tyr Gly Glu Thr Gly Gly Asn Ser Pro Val Gln Glu Phe
            35                  40                  45

Thr Val Pro Thr Met Asp His Thr Ala Thr Ile Ser Gly Leu Lys Pro
 50                  55                  60

Gly Val Asp Tyr Thr Ile Thr Val Tyr Ala Val Thr Leu Asp His Arg
 65                  70                  75                  80

Ser Leu Trp Pro Ile Ser Ile Asn Tyr Arg Thr
            85                  90
```

<210> SEQ ID NO 6
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

```
Val Ser Asp Val Pro Arg Asp Leu Glu Val Val Ala Ala Thr Pro Thr
 1               5                  10                  15

Ser Leu Leu Ile Ser Trp Pro Thr His Tyr Lys Val Ala Arg Tyr Tyr
            20                  25                  30

Arg Ile Thr Tyr Gly Glu Thr Gly Gly Asn Ser Pro Val Gln Glu Phe
            35                  40                  45

Thr Val Pro Tyr His Asp His Thr Ala Thr Ile Ser Gly Leu Lys Pro
 50                  55                  60

Gly Val Asp Tyr Thr Ile Thr Val Tyr Ala Val Thr Asp Tyr Lys Met
 65                  70                  75                  80

Lys Pro Arg Asn Tyr Gly Pro Ile Ser Ile Asn Tyr Arg Thr
            85                  90
```

<210> SEQ ID NO 7
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Val Ser Asp Val Pro Arg Asp Leu Glu Val Val Ala Ala Thr Pro Thr
 1               5                  10                  15

Ser Leu Leu Ile Ser Trp Ser Tyr Glu Ser Lys Tyr Arg Tyr Tyr
            20                  25                  30

Arg Ile Thr Tyr Gly Glu Thr Gly Gly Asn Ser Pro Val Gln Glu Phe
            35                  40                  45

Thr Val Pro Ala Tyr Tyr Pro Thr Ala Thr Ile Ser Gly Leu Lys Pro
 50                  55                  60

Gly Val Asp Tyr Thr Ile Thr Val Tyr Ala Val Thr Glu Lys Gly His
 65                  70                  75                  80

Tyr Arg Tyr Ile Tyr Ala Pro Ile Ser Ile Asn Tyr Arg Thr
            85                  90
```

<210> SEQ ID NO 8
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 8

Val Ser Asp Val Pro Arg Asp Leu Glu Val Val Ala Ala Thr Pro Thr
1               5                   10                  15

Ser Leu Leu Ile Ser Trp Gly Ser His Leu Lys Val Lys Arg Tyr Tyr
            20                  25                  30

Arg Ile Thr Tyr Gly Glu Thr Gly Gly Asn Ser Pro Val Gln Glu Phe
        35                  40                  45

Thr Val Pro Phe Thr Ser Arg Thr Ala Thr Ile Ser Gly Leu Lys Pro
    50                  55                  60

Gly Val Asp Tyr Thr Ile Thr Val Tyr Ala Val Thr Lys Phe Arg Asn
65                  70                  75                  80

Tyr Arg Pro Ile Ser Ile Asn Tyr Arg Thr
                85                  90

<210> SEQ ID NO 9
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 9

Val Ser Asp Val Pro Arg Asp Leu Glu Val Val Ala Ala Thr Pro Thr
1               5                   10                  15

Ser Leu Leu Ile Ser Trp Ala Pro Tyr Val Arg Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Thr Leu Ser Arg Thr Ala Thr Ile Ser Gly Leu Lys Pro
    50                  55                  60

Gly Val Asp Tyr Thr Ile Thr Val Tyr Ala Val Thr Arg Thr Arg Asn
65                  70                  75                  80

Tyr Gly Pro Ile Ser Ile Asn Tyr Arg Thr
                85                  90

<210> SEQ ID NO 10
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 10

Val Ser Asp Val Pro Arg Asp Leu Glu Val Val Ala Ala Thr Pro Thr
1               5                   10                  15

Ser Leu Leu Ile Ser Trp Gly Ser His Leu Lys Val Lys Arg Tyr Tyr
            20                  25                  30

Arg Ile Thr Tyr Gly Glu Thr Gly Gly Asn Ser Pro Val Gln Glu Phe
        35                  40                  45

Thr Val Pro Tyr Thr Ser Arg Thr Ala Thr Ile Ser Gly Leu Lys Pro
    50                  55                  60

Gly Val Asp Tyr Thr Ile Thr Val Tyr Ala Val Thr Lys Ser Gln His
65                  70                  75                  80

Ser Arg Pro Ile Ser Ile Asn Tyr Arg Thr
            85                  90

<210> SEQ ID NO 11
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Val Ser Asp Val Pro Arg Asp Leu Glu Val Val Ala Ala Thr Pro Thr
1               5                   10                  15

Ser Leu Leu Ile Ser Trp Ser Val Glu Ala Met Asp Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Glu Glu Pro Gly Thr Ala Thr Ile Ser Gly Leu Lys Pro
    50                  55                  60

Gly Val Asp Tyr Thr Ile Thr Val Tyr Ala Val Thr Thr Lys Tyr Tyr
65                  70                  75                  80

Tyr Leu Val Ile Glu Pro Pro Ile Ser Ile Asn Tyr Arg Thr
            85                  90

<210> SEQ ID NO 12
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Val Ser Asp Val Pro Arg Asp Leu Glu Val Val Ala Ala Thr Pro Thr
1               5                   10                  15

Ser Leu Leu Ile Ser Trp Asp Pro His Asn Gln Asp Pro Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ala Tyr Ser Thr Ala Thr Ile Ser Gly Leu Lys Pro
    50                  55                  60

Gly Val Asp Tyr Thr Ile Thr Val Tyr Ala Val Thr Asp Lys Glu His
65                  70                  75                  80

His Gln Tyr Leu Ile Asn Pro Ile Ser Ile Asn Tyr Arg Thr
            85                  90

<210> SEQ ID NO 13
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Val Ser Asp Val Pro Arg Asp Leu Glu Val Val Ala Ala Thr Pro Thr
1               5                   10                  15

```
Ser Leu Leu Ile Ser Trp Ile Gly Leu Asp Gly Leu Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Ala Glu Lys Gln Thr Ala Thr Ile Ser Gly Leu Lys Pro
        50                  55                  60

Gly Val Asp Tyr Thr Ile Thr Val Tyr Ala Val Thr Thr Asp Thr Gly
65                  70                  75                  80

Phe Ile Ala Arg Leu Met Ser Leu Ile Tyr Pro Ile Ser Ile Asn Tyr
                85                  90                  95

Arg Thr
```

<210> SEQ ID NO 14
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 14

```
Val Ser Asp Val Pro Arg Asp Leu Glu Val Val Ala Ala Thr Pro Thr
1               5                   10                  15

Ser Leu Leu Ile Ser Trp Ile Tyr Val Leu His His Ile Arg Tyr Tyr
            20                  25                  30

Arg Ile Thr Tyr Gly Glu Thr Gly Gly Asn Ser Pro Val Gln Glu Phe
            35                  40                  45

Thr Val Pro Ser Gln His His Thr Ala Thr Ile Ser Gly Leu Lys Pro
        50                  55                  60

Gly Val Asp Tyr Thr Ile Thr Val Tyr Ala Val Thr Glu Thr Arg Pro
65                  70                  75                  80

Tyr Arg Tyr Leu Met Tyr Pro Ile Ser Ile Asn Tyr Arg Thr
                85                  90
```

<210> SEQ ID NO 15
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 15

```
Val Ser Asp Val Pro Arg Asp Leu Glu Val Val Ala Ala Thr Pro Thr
1               5                   10                  15

Ser Leu Leu Ile Ser Trp Pro Pro Tyr Leu Arg Val Ala Arg Tyr Tyr
            20                  25                  30

Arg Ile Thr Tyr Gly Glu Thr Gly Gly Asn Ser Pro Val Gln Glu Phe
            35                  40                  45

Thr Val Pro Ser Ser Ala Arg Thr Ala Thr Ile Ser Gly Leu Lys Pro
        50                  55                  60

Gly Val Asp Tyr Thr Ile Thr Val Tyr Ala Val Thr Pro Ser Asn Ile
65                  70                  75                  80

Ile Gly Arg His Tyr Gly Pro Ile Ser Ile Asn Tyr Arg Thr
                85                  90
```

<210> SEQ ID NO 16

```
<211> LENGTH: 89
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Val Ser Asp Val Pro Arg Asp Leu Glu Val Val Ala Ala Thr Pro Thr
1               5                   10                  15

Ser Leu Leu Ile Ser Trp Gly Thr His Val Lys Val Pro Arg Tyr Tyr
            20                  25                  30

Arg Ile Thr Tyr Gly Glu Thr Gly Gly Asn Ser Pro Val Gln Glu Phe
        35                  40                  45

Thr Val Pro Tyr Ser Asp His Thr Ala Thr Ile Ser Gly Leu Lys Pro
    50                  55                  60

Gly Val Asp Tyr Thr Ile Thr Val Tyr Ala Val Thr Asp Tyr Asp Tyr
65                  70                  75                  80

Lys Pro Ile Ser Ile Asn Tyr Arg Thr
                85

<210> SEQ ID NO 17
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Val Ser Asp Val Pro Arg Asp Leu Glu Val Val Ala Ala Thr Pro Thr
1               5                   10                  15

Ser Leu Leu Ile Ser Trp Ser Pro Tyr Leu Arg Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Ala Arg Thr Ala Thr Ile Ser Gly Leu Lys Pro
    50                  55                  60

Gly Val Asp Tyr Thr Ile Thr Val Tyr Ala Val Thr Pro Ser Asn Ile
65                  70                  75                  80

Ile Gly Arg His Tyr Gly Pro Ile Ser Ile Asn Tyr Arg Thr
                85                  90

<210> SEQ ID NO 18
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Val Ser Asp Val Pro Arg Asp Leu Glu Val Val Ala Ala Thr Pro Thr
1               5                   10                  15

Ser Leu Leu Ile Ser Trp Glu Val Arg Tyr Tyr Pro Tyr Arg Tyr Tyr
            20                  25                  30

Arg Ile Thr Tyr Gly Glu Thr Gly Gly Asn Ser Pro Val Gln Glu Phe
        35                  40                  45
```

```
Thr Val Pro Ser Lys Tyr Ser Thr Ala Thr Ile Ser Gly Leu Lys Pro
        50                  55                  60

Gly Val Asp Tyr Thr Ile Thr Val Tyr Ala Val Thr Asp Tyr Lys Met
 65                  70                  75                  80

Lys Pro Arg Asn Tyr Gly Pro Ile Ser Ile Asn Tyr Arg Thr
                85                  90

<210> SEQ ID NO 19
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Val Ser Asp Val Pro Arg Asp Leu Glu Val Val Ala Ala Thr Pro Thr
 1               5                  10                  15

Ser Leu Leu Ile Ser Trp Thr Thr His Phe Thr Val Ser Arg Tyr Tyr
                20                  25                  30

Arg Ile Thr Tyr Gly Glu Thr Gly Gly Asn Ser Pro Val Gln Glu Phe
            35                  40                  45

Thr Val Pro Glu Val His Tyr Thr Ala Thr Ile Ser Gly Leu Lys Pro
        50                  55                  60

Gly Val Asp Tyr Thr Ile Thr Val Tyr Ala Val Thr His Arg Arg Arg
 65                  70                  75                  80

Arg Arg Tyr His Pro Ile Ser Ile Asn Tyr Arg Thr
                85                  90

<210> SEQ ID NO 20
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Val Ser Asp Val Pro Arg Asp Leu Glu Val Val Ala Ala Thr Pro Thr
 1               5                  10                  15

Ser Leu Leu Ile Ser Trp Asp His Asp Met Pro Gly Gly Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Ser Tyr Pro Thr Ala Thr Ile Ser Gly Leu Lys Pro
        50                  55                  60

Gly Val Asp Tyr Thr Ile Thr Val Tyr Ala Val Thr Tyr Ser Tyr Leu
 65                  70                  75                  80

Tyr Gln Tyr Asn His Ala Pro Ile Ser Ile Asn Tyr Arg Thr
                85                  90

<210> SEQ ID NO 21
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 21

Val Ser Asp Val Pro Arg Asp Leu Glu Val Val Ala Ala Thr Pro Thr
1               5                   10                  15

Ser Leu Leu Ile Ser Trp Tyr Asn Asp Pro Arg Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Gln Thr Asn Met
65                  70                  75                  80

His Tyr Leu Met His Tyr Pro Ile Ser Ile Asn Tyr Arg Thr
                85                  90

<210> SEQ ID NO 22
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Val Ser Asp Val Pro Arg Asp Leu Glu Val Val Ala Ala Thr Pro Thr
1               5                   10                  15

Ser Leu Leu Ile Ser Trp Gly Ser Lys Leu Leu Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Arg Leu Ala Lys Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 23
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Val Ser Asp Val Pro Arg Asp Leu Glu Val Val Ala Ala Thr Pro Thr
1               5                   10                  15

Ser Leu Leu Ile Ser Trp Ile Tyr Arg Ser Tyr Lys Arg Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Asn Tyr Pro Thr Ala Thr Ile Ser Gly Leu Lys Pro
    50                  55                  60

Gly Val Asp Tyr Thr Ile Thr Val Tyr Ala Val Thr Gln Gln Tyr Ser
65                  70                  75                  80

Ser Pro Thr Tyr Ser His Pro Ile Ser Ile Asn Tyr Arg Thr
                85                  90

```
<210> SEQ ID NO 24
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Val Ser Asp Val Pro Arg Asp Leu Glu Val Val Ala Ala Thr Pro Thr
1               5                   10                  15

Ser Leu Leu Ile Ser Trp Ser Pro Tyr Leu Arg Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ala Ala Arg Thr Ala Thr Ile Ser Gly Leu Lys Pro
    50                  55                  60

Gly Val Asp Tyr Thr Ile Thr Val Tyr Ala Val Thr Ala Ser Leu Ile
65                  70                  75                  80

Ile Gly Arg His Tyr Gly Pro Ile Ser Ile Asn Tyr Arg Thr
                85                  90

<210> SEQ ID NO 25
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Val Ser Asp Val Pro Arg Asp Leu Glu Val Val Ala Ala Thr Pro Thr
1               5                   10                  15

Ser Leu Leu Ile Ser Trp Asn His Thr Leu Lys Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Tyr Thr His Ser Thr Ala Thr Ile Ser Gly Leu Lys Pro
    50                  55                  60

Gly Val Asp Tyr Thr Ile Thr Val Tyr Ala Val Thr Glu Arg Glu Ser
65                  70                  75                  80

Tyr Arg Tyr Met His Ile Pro Ile Ser Ile Asn Tyr Arg Thr
                85                  90

<210> SEQ ID NO 26
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Val Ser Asp Val Pro Arg Asp Leu Glu Val Val Ala Ala Thr Pro Thr
1               5                   10                  15

Ser Leu Leu Ile Ser Trp Ser Asp Thr Leu Arg Val Lys Arg Tyr Tyr
            20                  25                  30
```

```
Arg Ile Thr Tyr Gly Glu Thr Gly Gly Asn Ser Pro Val Gln Glu Phe
            35                  40                  45

Thr Val Pro Tyr His Ser Gln Thr Ala Thr Ile Ser Gly Leu Lys Pro
 50                  55                  60

Gly Val Asp Tyr Thr Ile Thr Val Tyr Ala Val Thr Pro Ser Met Met
 65                  70                  75                  80

Asn Tyr Arg Asn Tyr Gly Pro Ile Ser Ile Asn Tyr Arg Thr
                85                  90
```

<210> SEQ ID NO 27
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 27

```
Val Ser Asp Val Pro Arg Asp Leu Glu Val Val Ala Ala Thr Pro Thr
 1               5                  10                  15

Ser Leu Leu Ile Ser Trp Asp Asn Ser Phe Val Val Gln Arg Tyr Tyr
            20                  25                  30

Arg Ile Thr Tyr Gly Glu Thr Gly Gly Asn Ser Pro Val Gln Glu Phe
            35                  40                  45

Thr Val Pro Arg Tyr Ala Arg Thr Ala Thr Ile Ser Gly Leu Lys Pro
 50                  55                  60

Gly Val Asp Tyr Thr Ile Thr Val Tyr Ala Val Thr Ala Leu Asn Pro
 65                  70                  75                  80

Arg Ala Tyr Arg Pro Ile Ser Ile Asn Tyr Arg Thr
                85                  90
```

<210> SEQ ID NO 28
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 28

```
Val Ser Asp Val Pro Arg Asp Leu Glu Val Val Ala Ala Thr Pro Thr
 1               5                  10                  15

Ser Leu Leu Ile Ser Trp Ser Ser Arg Leu Ile Val Arg Arg Tyr Tyr
            20                  25                  30

Arg Ile Thr Tyr Gly Glu Thr Gly Gly Asn Ser Pro Val Gln Glu Phe
            35                  40                  45

Thr Val Pro Trp Gly Asn Arg Thr Ala Thr Ile Ser Gly Leu Lys Pro
 50                  55                  60

Gly Val Asp Tyr Thr Ile Thr Val Tyr Ala Val Thr Lys Met Arg Asp
 65                  70                  75                  80

Tyr Arg Pro Ile Ser Ile Asn Tyr Arg Thr
                85                  90
```

<210> SEQ ID NO 29
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 29

Val Ser Asp Val Pro Arg Asp Leu Glu Val Val Ala Ala Thr Pro Thr
1               5                   10                  15

Ser Leu Leu Ile Ser Trp Ser Ser Arg Leu Ile Val Arg Arg Tyr Tyr
            20                  25                  30

Arg Ile Thr Tyr Gly Glu Thr Gly Gly Asn Ser Pro Val Gln Glu Phe
        35                  40                  45

Thr Val Pro Trp Gly Asn Arg Thr Ala Thr Ile Ser Gly Leu Lys Pro
    50                  55                  60

Gly Val Asp Tyr Thr Ile Thr Val Tyr Ala Val Thr His Thr Arg Pro
65                  70                  75                  80

Arg Asn Tyr Gln Pro Ile Ser Ile Asn Tyr Arg Thr
                85                  90

<210> SEQ ID NO 30
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 30

Val Ser Asp Val Pro Arg Asp Leu Glu Val Val Ala Ala Thr Pro Thr
1               5                   10                  15

Ser Leu Leu Ile Ser Trp Gly Thr Arg Leu Arg Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Arg Ser Val Glu Thr Ala Thr Ile Ser Gly Leu Lys Pro
    50                  55                  60

Gly Val Asp Tyr Thr Ile Thr Val Tyr Ala Val Thr Leu Asn Ser Leu
65                  70                  75                  80

Arg Arg Tyr Gly Pro Ile Ser Ile Asn Tyr Arg Thr
                85                  90

<210> SEQ ID NO 31
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 31

Val Ser Asp Val Pro Arg Asp Leu Glu Val Val Ala Ala Thr Pro Thr
1               5                   10                  15

Ser Leu Leu Ile Ser Trp Glu Tyr Asp Arg Pro Ala Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Gln Thr Asn Met
65                  70                  75                  80

His Tyr Leu Met His Tyr Pro Ile Ser Ile Asn Tyr Arg Thr
                85                  90

<210> SEQ ID NO 32
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Val Ser Asp Val Pro Arg Asp Leu Glu Val Val Ala Ala Thr Pro Thr
1               5                   10                  15

Ser Leu Leu Ile Ser Trp Ser Thr His Phe Thr Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Val Asn Tyr Thr Ala Thr Ile Ser Gly Leu Lys Pro
    50                  55                  60

Gly Val Asp Tyr Thr Ile Thr Val Tyr Ala Val Thr Arg Thr Arg Asn
65                  70                  75                  80

Tyr Gly Pro Ile Ser Ile Asn Tyr Arg Thr
                85                  90

<210> SEQ ID NO 33
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Val Ser Asp Val Pro Arg Asp Leu Glu Val Val Ala Ala Thr Pro Thr
1               5                   10                  15

Ser Leu Leu Ile Ser Trp Asp Lys His Ala Tyr Tyr Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Glu Asn His Leu Thr Ala Thr Ile Ser Gly Leu Lys Pro
    50                  55                  60

Gly Val Asp Tyr Thr Ile Thr Val Tyr Ala Val Thr Asp Arg Thr His
65                  70                  75                  80

Ser Arg Ile Tyr His Arg Pro Ile Ser Ile Asn Tyr Arg Thr
                85                  90

<210> SEQ ID NO 34
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Val Ser Asp Val Pro Arg Asp Leu Glu Val Val Ala Ala Thr Pro Thr
1               5                   10                  15

-continued

Ser Leu Leu Ile Ser Trp Pro Asn Asn Thr Ser Arg Gly Arg Tyr Tyr
                20                  25                  30

Arg Ile Thr Tyr Gly Glu Thr Gly Gly Asn Ser Pro Val Gln Glu Phe
            35                  40                  45

Thr Val Pro Ala Ser Tyr Pro Thr Ala Thr Ile Ser Gly Leu Lys Pro
        50                  55                  60

Gly Val Asp Tyr Thr Ile Thr Val Tyr Ala Val Thr Glu Arg Val Ala
65                  70                  75                  80

Tyr Arg Tyr Met His Lys Pro Ile Ser Ile Asn Tyr Arg Thr
                85                  90

<210> SEQ ID NO 35
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Val Ser Asp Val Pro Arg Asp Leu Glu Val Val Ala Ala Thr Pro Thr
1               5                   10                  15

Ser Leu Leu Ile Ser Trp Ser His Arg Leu Arg Val Lys Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser His Tyr Gln Thr Ala Thr Ile Ser Gly Leu Lys Pro
        50                  55                  60

Gly Val Asp Tyr Thr Ile Thr Val Tyr Ala Val Thr Glu Lys Thr Ser
65                  70                  75                  80

Tyr Arg Ile Met His Ser Pro Ile Ser Ile Asn Tyr Arg Thr
                85                  90

<210> SEQ ID NO 36
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Val Ser Asp Val Pro Arg Asp Leu Glu Val Val Ala Ala Thr Pro Thr
1               5                   10                  15

Ser Leu Leu Ile Ser Trp Glu Tyr Asp Gly Thr Ala Gly Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Ser Tyr Pro Thr Ala Thr Ile Ser Gly Leu Lys Pro
        50                  55                  60

Gly Val Asp Tyr Thr Ile Thr Val Tyr Ala Val Thr Tyr Ser Tyr Leu
65                  70                  75                  80

Tyr Gln Tyr Asn His Ala Pro Ile Ser Ile Asn Tyr Arg Thr
                85                  90

<210> SEQ ID NO 37
<211> LENGTH: 94
<212> TYPE: PRT

-continued

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Val Ser Asp Val Pro Arg Asp Leu Glu Val Val Ala Ala Thr Pro Thr
1               5                   10                  15

Ser Leu Leu Ile Ser Trp Ser His Arg Leu Arg Val Lys Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser His Tyr Gln Thr Ala Thr Ile Ser Gly Leu Lys Pro
    50                  55                  60

Gly Val Asp Tyr Thr Ile Thr Val Tyr Ala Val Thr Pro Ala Val Tyr
65                  70                  75                  80

Tyr Ser Tyr Asn Tyr Gly Pro Ile Ser Ile Asn Tyr Arg Thr
                85                  90

<210> SEQ ID NO 38
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Val Ser Asp Val Pro Arg Asp Leu Glu Val Val Ala Ala Thr Pro Thr
1               5                   10                  15

Ser Leu Leu Ile Ser Trp Asn His Thr Leu Lys Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Tyr Thr His Ser Thr Ala Thr Ile Ser Gly Leu Lys Pro
    50                  55                  60

Gly Val Asp Tyr Thr Ile Thr Val Tyr Ala Val Thr Asn Tyr Lys Gly
65                  70                  75                  80

Pro Arg Gly Tyr Gly Pro Ile Ser Ile Asn Tyr Arg Thr
                85                  90

<210> SEQ ID NO 39
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Val Ser Asp Val Pro Arg Asp Leu Glu Val Val Ala Ala Thr Pro Thr
1               5                   10                  15

Ser Leu Leu Ile Ser Trp Ser Asp Val Phe Pro Ala Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala His Ser Pro Thr Ala Thr Ile Ser Gly Leu Lys Pro
    50                  55                  60

```
Gly Val Asp Tyr Thr Ile Thr Val Tyr Ala Val Thr Pro Ser Met Met
 65                  70                  75                  80

Asn Tyr Arg Asn Tyr Gly Pro Ile Ser Ile Asn Tyr Arg Thr
                 85                  90
```

<210> SEQ ID NO 40
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

```
Val Ser Asp Val Pro Arg Asp Leu Glu Val Val Ala Ala Thr Pro Thr
 1               5                  10                  15

Ser Leu Leu Ile Ser Trp Asp Asn Asn Phe Leu Val Gln Arg Tyr Tyr
                20                  25                  30

Arg Ile Thr Tyr Gly Glu Thr Gly Gly Asn Ser Pro Val Gln Glu Phe
            35                  40                  45

Thr Val Pro Arg Tyr Ala His Thr Ala Thr Ile Ser Gly Leu Lys Pro
        50                  55                  60

Gly Val Asp Tyr Thr Ile Thr Val Tyr Ala Val Thr Lys Met Arg Asp
 65                  70                  75                  80

Tyr Arg Pro Ile Ser Ile Asn Tyr Arg Thr
                 85                  90
```

<210> SEQ ID NO 41
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

```
Val Ser Asp Val Pro Arg Asp Leu Glu Val Val Ala Ala Thr Pro Thr
 1               5                  10                  15

Ser Leu Leu Ile Ser Trp Pro Phe Gln Ala Val Ser Asn Arg Tyr Tyr
                20                  25                  30

Arg Ile Thr Tyr Gly Glu Thr Gly Gly Asn Ser Pro Val Gln Glu Phe
            35                  40                  45

Thr Val Pro Ala Tyr Pro Asn Thr Ala Thr Ile Ser Gly Leu Lys Pro
        50                  55                  60

Gly Val Asp Tyr Thr Ile Thr Val Tyr Ala Val Thr Tyr Met Ser Gly
 65                  70                  75                  80

His Arg Leu Leu His Ala Pro Ile Ser Ile Asn Tyr Arg Thr
                 85                  90
```

<210> SEQ ID NO 42
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Val Ser Asp Val Pro Arg Asp Leu Glu Val Val Ala Ala Thr Pro Thr
1               5                   10                  15

Ser Leu Leu Ile Ser Trp Tyr Pro Ser Leu Ile Leu Glu Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp Leu Arg Leu Thr Ala Thr Ile Ser Gly Leu Lys Pro
    50                  55                  60

Gly Val Asp Tyr Thr Ile Thr Val Tyr Ala Val Thr Asp Lys Lys Ser
65                  70                  75                  80

Tyr Arg Tyr Tyr His Ala Pro Ile Ser Ile Asn Tyr Arg Thr
                85                  90

<210> SEQ ID NO 43
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Val Ser Asp Val Pro Arg Asp Leu Glu Val Val Ala Ala Thr Pro Thr
1               5                   10                  15

Ser Leu Leu Ile Ser Trp Tyr Asn Asp Pro Arg Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Ile Lys Gly Ile
65                  70                  75                  80

Tyr Gln Tyr Thr Tyr His Pro Ile Ser Ile Asn Tyr Arg Thr
                85                  90

<210> SEQ ID NO 44
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Val Ser Asp Val Pro Arg Asp Leu Glu Val Val Ala Ala Thr Pro Thr
1               5                   10                  15

Ser Leu Leu Ile Ser Trp Tyr Asn Asp Pro Arg Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Tyr Ser Tyr Leu
65                  70                  75                  80

Tyr Gln Tyr Asn His Ala Pro Ile Ser Ile Asn Tyr Arg Thr
                85                  90

```
<210> SEQ ID NO 45
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Val Ser Asp Val Pro Arg Asp Leu Glu Val Val Ala Ala Thr Pro Thr
1               5                   10                  15

Ser Leu Leu Ile Ser Trp Gln Tyr Asn Thr Ser Arg Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ser Tyr Pro Thr Ala Thr Ile Ser Gly Leu Lys Pro
    50                  55                  60

Gly Val Asp Tyr Thr Ile Thr Val Tyr Ala Val Thr Glu Arg Val Ala
65                  70                  75                  80

Tyr Arg Tyr Met His Lys Pro Ile Ser Ile Asn Tyr Arg Thr
                85                  90

<210> SEQ ID NO 46
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Val Ser Asp Val Pro Arg Asp Leu Glu Val Val Ala Ala Thr Pro Thr
1               5                   10                  15

Ser Leu Leu Ile Ser Trp Pro Val His Arg Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Gly Gln Phe Thr Ala Thr Ile Ser Gly Leu Lys Pro
    50                  55                  60

Gly Val Asp Tyr Thr Ile Thr Val Tyr Ala Val Thr Leu Gly Lys Phe
65                  70                  75                  80

Arg Ser Tyr Leu Pro Ile Ser Ile Asn Tyr Arg Thr
                85                  90

<210> SEQ ID NO 47
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Val Ser Asp Val Pro Arg Asp Leu Glu Val Val Ala Ala Thr Pro Thr
1               5                   10                  15

Ser Leu Leu Ile Ser Trp Ser Tyr Asn Met Lys Pro His Arg Tyr Tyr
            20                  25                  30

Arg Ile Thr Tyr Gly Glu Thr Gly Gly Asn Ser Pro Val Gln Glu Phe
        35                  40                  45
```

```
Thr Val Pro Ser Ser Tyr Pro Thr Ala Thr Ile Ser Gly Leu Lys Pro
 50                  55                  60

Gly Val Asp Tyr Thr Ile Thr Val Tyr Ala Val Thr Asp Arg Tyr Met
 65                  70                  75                  80

Tyr Arg Met Leu His Lys Pro Ile Ser Ile Asn Tyr Arg Thr
                 85                  90

<210> SEQ ID NO 48
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Val Ser Asp Val Pro Arg Asp Leu Glu Val Val Ala Ala Thr Pro Thr
 1               5                  10                  15

Ser Leu Leu Ile Ser Trp Gly Thr Arg Leu Arg Val Ser Arg Tyr Tyr
                 20                  25                  30

Arg Ile Thr Tyr Gly Glu Thr Gly Gly Asn Ser Pro Val Gln Glu Phe
             35                  40                  45

Thr Val Pro Arg Ser Val Glu Thr Ala Thr Ile Ser Gly Leu Lys Pro
 50                  55                  60

Gly Val Asp Tyr Thr Ile Thr Val Tyr Ala Val Thr Leu Asn Ser Leu
 65                  70                  75                  80

Arg Arg Tyr Gly Pro Ile Ser Ile Asn Tyr Arg Thr
                 85                  90

<210> SEQ ID NO 49
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Val Ser Asp Val Pro Arg Asp Leu Glu Val Val Ala Ala Thr Pro Thr
 1               5                  10                  15

Ser Leu Leu Ile Ser Trp Gly Thr Val Arg Arg Val Ala Arg Tyr Tyr
                 20                  25                  30

Arg Ile Thr Tyr Gly Glu Thr Gly Gly Asn Ser Pro Val Gln Glu Phe
             35                  40                  45

Thr Val Pro Ala Leu Gly Thr Thr Ala Thr Ile Ser Gly Leu Lys Pro
 50                  55                  60

Gly Val Asp Tyr Thr Ile Thr Val Tyr Ala Val Thr Arg Thr Arg Asn
 65                  70                  75                  80

Tyr Gly Pro Ile Ser Ile Asn Tyr Arg Thr
                 85                  90

<210> SEQ ID NO 50
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 50

Val Ser Asp Val Pro Arg Asp Leu Glu Val Val Ala Ala Thr Pro Thr
1               5                   10                  15

Ser Leu Leu Ile Ser Trp Tyr Leu Asp Thr Thr Arg Asp Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Tyr Pro Met Thr Ala Thr Ile Ser Gly Leu Lys Pro
    50                  55                  60

Gly Val Asp Tyr Thr Ile Thr Val Tyr Ala Val Thr Glu Ser Ile Gln
65                  70                  75                  80

Tyr Arg Arg Ile His Arg Pro Ile Ser Ile Asn Tyr Arg Thr
                85                  90

<210> SEQ ID NO 51
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Val Ser Asp Val Pro Arg Asp Leu Glu Val Val Ala Ala Thr Pro Thr
1               5                   10                  15

Ser Leu Leu Ile Ser Trp Ala Pro Tyr Val Arg Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Thr Leu Ser Arg Thr Ala Thr Ile Ser Gly Leu Lys Pro
    50                  55                  60

Gly Val Asp Tyr Thr Ile Thr Val Tyr Ala Val Thr Arg Thr Arg Asn
65                  70                  75                  80

Tyr Gly Pro Ile Ser Ile Asn Tyr Arg Thr
                85                  90

<210> SEQ ID NO 52
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Val Ser Asp Val Pro Arg Asp Leu Glu Val Val Ala Ala Thr Pro Thr
1               5                   10                  15

Ser Leu Leu Ile Ser Trp Ser Glu His Asp Tyr Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro His Asn Tyr Pro Thr Ala Thr Ile Ser Gly Leu Lys Pro
    50                  55                  60

Gly Val Asp Tyr Thr Ile Thr Val Tyr Ala Val Thr Asp His Gly Gln
65                  70                  75                  80

Tyr Arg Lys Met His Ser Pro Ile Ser Ile Asn Tyr Arg Thr
```

-continued

```
                     85                  90

<210> SEQ ID NO 53
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Val Ser Asp Val Pro Arg Asp Leu Glu Val Val Ala Ala Thr Pro Thr
1               5                   10                  15

Ser Leu Leu Ile Ser Trp Val Gln Glu Phe Thr Val Pro Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Gln Thr Asn Met
65                  70                  75                  80

His Tyr Leu Met His Tyr Pro Ile Ser Ile Asn Tyr Arg Thr
                85                  90

<210> SEQ ID NO 54
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Val Ser Asp Val Pro Arg Asp Leu Glu Val Val Ala Ala Thr Pro Thr
1               5                   10                  15

Ser Leu Leu Ile Ser Trp Gly Arg Val Ser Lys His Arg Arg Tyr Tyr
            20                  25                  30

Arg Ile Thr Tyr Gly Glu Thr Gly Gly Asn Ser Pro Val Gln Glu Phe
        35                  40                  45

Thr Val Pro Val Pro Gly Thr Thr Ala Thr Ile Ser Gly Leu Lys Pro
    50                  55                  60

Gly Val Asp Tyr Thr Ile Thr Val Tyr Ala Val Thr Arg Glu Ala Pro
65                  70                  75                  80

Thr Gly Ile Arg Pro Ile Ser Ile Asn Tyr Arg Thr
                85                  90

<210> SEQ ID NO 55
<211> LENGTH: 88
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Val Ser Asp Val Pro Arg Asp Leu Glu Val Val Ala Ala Thr Pro Thr
1               5                   10                  15

Ser Leu Leu Ile Ser Trp Lys Lys Tyr Tyr His Met Asp Arg Tyr Tyr
            20                  25                  30
```

Arg Ile Thr Tyr Gly Glu Thr Gly Asn Ser Pro Val Gln Glu Phe
            35                  40                  45

Thr Val Pro Asp Ala Tyr Ser Thr Ala Thr Ile Ser Gly Leu Lys Pro
 50                  55                  60

Gly Val Asp Tyr Thr Ile Thr Val Tyr Ala Val Thr Tyr Asp Gly Ile
65                  70                  75                  80

Pro Ile Ser Ile Asn Tyr Arg Thr
                85

<210> SEQ ID NO 56
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Val Ser Asp Val Pro Arg Asp Leu Glu Val Val Ala Ala Thr Pro Thr
 1               5                  10                  15

Ser Leu Leu Ile Ser Trp Val Asn Asp Pro Gln Arg Asn Arg Tyr Tyr
                20                  25                  30

Arg Ile Thr Tyr Gly Glu Thr Gly Asn Ser Pro Val Gln Glu Phe
            35                  40                  45

Thr Val Pro Ala Tyr Tyr Pro Thr Ala Thr Ile Ser Gly Leu Lys Pro
 50                  55                  60

Gly Val Asp Tyr Thr Ile Thr Val Tyr Ala Val Thr Tyr Ser His Ile
65                  70                  75                  80

Lys Tyr Leu Tyr His Lys Pro Ile Ser Ile Asn Tyr Arg Thr
                85                  90

<210> SEQ ID NO 57
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Val Ser Asp Val Pro Arg Asp Leu Glu Val Val Ala Ala Thr Pro Thr
 1               5                  10                  15

Ser Leu Leu Ile Ser Trp Glu Tyr Asp Arg Val Lys Lys Arg Tyr Tyr
                20                  25                  30

Arg Ile Thr Tyr Gly Glu Thr Gly Gly Asn Ser Pro Val Gln Glu Phe
            35                  40                  45

Thr Val Pro Ala Tyr Tyr Pro Thr Ala Thr Ile Ser Gly Leu Lys Pro
 50                  55                  60

Gly Val Asp Tyr Thr Ile Thr Val Tyr Ala Val Thr Glu His Ser His
65                  70                  75                  80

Val Arg Arg Met His Val Pro Ile Ser Ile Asn Tyr Arg Thr
                85                  90

<210> SEQ ID NO 58
<211> LENGTH: 90
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 58

Val Ser Asp Val Pro Arg Asp Leu Glu Val Val Ala Ala Thr Pro Thr
1               5                   10                  15

Ser Leu Leu Ile Ser Trp Ala Ser Gln Val Leu Gly His Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Leu Pro Asn Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 59
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Val Ser Asp Val Pro Arg Asp Leu Glu Val Val Ala Ala Thr Pro Thr
1               5                   10                  15

Ser Leu Leu Ile Ser Trp Gly Leu Asp Asp Tyr Tyr Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Tyr Pro Thr Ala Thr Ile Ser Gly Leu Lys Pro
    50                  55                  60

Gly Val Asp Tyr Thr Ile Thr Val Tyr Ala Val Thr Asp Arg Lys His
65                  70                  75                  80

Tyr Met Tyr Tyr His His Pro Ile Ser Ile Asn Tyr Arg Thr
                85                  90

<210> SEQ ID NO 60
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Val Ser Asp Val Pro Arg Asp Leu Glu Val Val Ala Ala Thr Pro Thr
1               5                   10                  15

Ser Leu Leu Ile Ser Trp Lys Tyr Tyr Gly Ser Arg Asp Arg Tyr Tyr
            20                  25                  30

Arg Ile Thr Tyr Gly Glu Thr Gly Gly Asn Ser Pro Val Gln Glu Phe
        35                  40                  45

Thr Val Pro Glu Ser Tyr Pro Thr Ala Thr Ile Ser Gly Leu Lys Pro
    50                  55                  60

Gly Val Asp Tyr Thr Ile Thr Val Tyr Ala Val Thr Asp Ser Arg Leu
```

```
65                  70                  75                  80
Tyr Arg Tyr Tyr His Ala Pro Ile Ser Ile Asn Tyr Arg Thr
                85                  90

<210> SEQ ID NO 61
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Val Ser Asp Val Pro Arg Asp Leu Glu Val Val Ala Ala Thr Pro Thr
1               5                   10                  15

Ser Leu Leu Ile Ser Trp Ser Arg Ala Val Arg Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Ala Asn Met Phe Thr Ala Thr Ile Ser Gly Leu Lys Pro
        50                  55                  60

Gly Val Asp Tyr Thr Ile Thr Val Tyr Ala Val Thr Ile Pro His Tyr
65                  70                  75                  80

Arg Asn Tyr Lys Pro Ile Ser Ile Asn Tyr Arg Thr
                85                  90

<210> SEQ ID NO 62
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Val Ser Asp Val Pro Arg Asp Leu Glu Val Val Ala Ala Thr Pro Thr
1               5                   10                  15

Ser Leu Leu Ile Ser Trp Ser Tyr Val Tyr Ala Pro Tyr Arg Tyr Tyr
            20                  25                  30

Arg Ile Thr Tyr Gly Glu Thr Gly Gly Asn Ser Pro Val Gln Glu Phe
            35                  40                  45

Thr Val Pro Ala His Tyr Pro Thr Ala Thr Ile Ser Gly Leu Lys Pro
        50                  55                  60

Gly Val Asp Tyr Thr Ile Thr Val Tyr Ala Val Thr Glu Lys Thr Ser
65                  70                  75                  80

Tyr Arg Ile Met His Ser Pro Ile Ser Ile Asn Tyr Arg Thr
                85                  90

<210> SEQ ID NO 63
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Val Ser Asp Val Pro Arg Asp Leu Glu Val Val Ala Ala Thr Pro Thr
1               5                   10                  15
```

```
Ser Leu Leu Ile Ser Trp Tyr Tyr Met Pro His Arg Asn Arg Tyr Tyr
            20                  25                  30

Arg Ile Thr Tyr Gly Glu Thr Gly Gly Asn Ser Pro Val Gln Glu Phe
            35                  40                  45

Thr Val Pro Ala Ser Tyr Pro Thr Ala Thr Ile Ser Gly Leu Lys Pro
        50                  55                  60

Gly Val Asp Tyr Thr Ile Thr Val Tyr Ala Val Thr Asp Gln Asn Tyr
65                  70                  75                  80

Tyr Arg Tyr Tyr His Lys Pro Ile Ser Ile Asn Tyr Arg Thr
                85                  90
```

<210> SEQ ID NO 64
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

```
Val Ser Asp Val Pro Arg Asp Leu Glu Val Val Ala Ala Thr Pro Thr
1               5                   10                  15

Ser Leu Leu Ile Ser Trp Thr Tyr Asp Ala His Lys Arg Arg Tyr Tyr
            20                  25                  30

Arg Ile Thr Tyr Gly Glu Thr Gly Gly Asn Ser Pro Val Gln Glu Phe
            35                  40                  45

Thr Val Pro Ser Ser Tyr Pro Thr Ala Thr Ile Ser Gly Leu Lys Pro
        50                  55                  60

Gly Val Asp Tyr Thr Ile Thr Val Tyr Ala Val Thr Glu Lys Gly Ser
65                  70                  75                  80

Leu Lys Ile Leu His Tyr Pro Ile Ser Ile Asn Tyr Arg Thr
                85                  90
```

<210> SEQ ID NO 65
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

```
Val Ser Asp Val Pro Arg Asp Leu Glu Val Val Ala Ala Thr Pro Thr
1               5                   10                  15

Ser Leu Leu Ile Ser Trp Ala Pro Tyr Val Arg Val Ala Arg Tyr Tyr
            20                  25                  30

Arg Ile Thr Tyr Gly Glu Thr Gly Gly Asn Ser Pro Val Gln Glu Phe
            35                  40                  45

Thr Val Pro Thr Leu Ser Arg Thr Ala Thr Ile Ser Gly Leu Lys Pro
        50                  55                  60

Gly Val Asp Tyr Thr Ile Thr Val Tyr Ala Val Thr Ser Pro Ser Leu
65                  70                  75                  80

Arg Asp Tyr Arg Pro Ile Ser Ile Asn Tyr Arg Thr
                85                  90
```

<210> SEQ ID NO 66
<211> LENGTH: 94

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Val Ser Asp Val Pro Arg Asp Leu Glu Val Val Ala Ala Thr Pro Thr
1               5                   10                  15

Ser Leu Leu Ile Ser Trp Tyr Pro Glu Tyr Val Arg Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ser Tyr Pro Thr Ala Thr Ile Ser Gly Leu Lys Pro
    50                  55                  60

Gly Val Asp Tyr Thr Ile Thr Val Tyr Ala Val Thr Lys Gly Val
65                  70                  75                  80

His Tyr Leu Tyr His Ser Pro Ile Ser Ile Asn Tyr Arg Thr
                85                  90

<210> SEQ ID NO 67
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Val Ser Asp Val Pro Arg Asp Leu Glu Val Val Ala Ala Thr Pro Thr
1               5                   10                  15

Ser Leu Leu Ile Ser Trp Pro Asp Ile Pro Ile Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Val Val Gly Thr Thr Ala Thr Ile Ser Gly Leu Lys Pro
    50                  55                  60

Gly Val Asp Tyr Thr Ile Thr Val Tyr Ala Val Thr Ser Ser Met Leu
65                  70                  75                  80

Tyr Ile Gln Ile Glu Pro Pro Ile Ser Ile Asn Tyr Arg Thr
                85                  90

<210> SEQ ID NO 68
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Val Ser Asp Val Pro Arg Asp Leu Glu Val Val Ala Ala Thr Pro Thr
1               5                   10                  15

Ser Leu Leu Ile Ser Trp Ala His Ser Gly Tyr Ser Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Glu Ser Tyr Pro Thr Ala Thr Ile Ser Gly Leu Lys Pro
```

```
                 50                  55                  60
Gly Val Asp Tyr Thr Ile Thr Val Tyr Ala Val Thr Asp Lys Asn Thr
 65                  70                  75                  80

Tyr Arg Tyr Tyr His Lys Pro Ile Ser Ile Asn Tyr Arg Thr
                 85                  90

<210> SEQ ID NO 69
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Val Ser Asp Val Pro Arg Asp Leu Glu Val Val Ala Ala Thr Pro Thr
  1               5                  10                  15

Ser Leu Leu Ile Ser Trp Asp His Ser Gly Ser Ser Tyr Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Glu Ser Tyr Pro Thr Ala Thr Ile Ser Gly Leu Lys Pro
         50                  55                  60

Gly Val Asp Tyr Thr Ile Thr Val Tyr Ala Val Thr Asp Lys Asn Thr
 65                  70                  75                  80

Tyr Arg Tyr Tyr His Lys Pro Ile Ser Ile Asn Tyr Arg Thr
                 85                  90

<210> SEQ ID NO 70
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Val Ser Asp Val Pro Arg Asp Leu Glu Val Val Ala Ala Thr Pro Thr
  1               5                  10                  15

Ser Leu Leu Ile Ser Trp His Val Thr Ser Asp Arg Asn Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Ala Thr Tyr Pro Thr Ala Thr Ile Ser Gly Leu Lys Pro
         50                  55                  60

Gly Val Asp Tyr Thr Ile Thr Val Tyr Ala Val Thr Ile Tyr Lys Gly
 65                  70                  75                  80

His Gln Ile Gln Tyr Thr Pro Ile Ser Ile Asn Tyr Arg Thr
                 85                  90

<210> SEQ ID NO 71
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71
```

Val Ser Asp Val Pro Arg Asp Leu Glu Val Val Ala Ala Thr Pro Thr
1               5                   10                  15

Ser Leu Leu Ile Ser Trp Ile Pro Tyr Ser Gly Pro Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala His Tyr Pro Thr Ala Thr Ile Ser Gly Leu Lys Pro
    50                  55                  60

Gly Val Asp Tyr Thr Ile Thr Val Tyr Ala Val Thr Gln Ser Val Ile
65                  70                  75                  80

Val Tyr Lys Gln Ala Ala Pro Ile Ser Ile Asn Tyr Arg Thr
                85                  90

<210> SEQ ID NO 72
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Val Ser Asp Val Pro Arg Asp Leu Glu Val Val Ala Ala Thr Pro Thr
1               5                   10                  15

Ser Leu Leu Ile Ser Trp Ser Tyr Asp Gln Ser Arg Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Met Tyr Pro Thr Ala Thr Ile Ser Gly Leu Lys Pro
    50                  55                  60

Gly Val Asp Tyr Thr Ile Thr Val Tyr Ala Val Thr Asp Lys Asn Thr
65                  70                  75                  80

Tyr Arg Tyr Tyr His Lys Pro Ile Ser Ile Asn Tyr Arg Thr
                85                  90

<210> SEQ ID NO 73
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Val Ser Asp Val Pro Arg Asp Leu Glu Val Val Ala Ala Thr Pro Thr
1               5                   10                  15

Ser Leu Leu Ile Ser Trp Gly Glu Pro Leu Glu Asp Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp His Ser Gln Thr Ala Thr Ile Ser Gly Leu Lys Pro
    50                  55                  60

Gly Val Asp Tyr Thr Ile Thr Val Tyr Ala Val Thr Ala Gly Ser Trp
65                  70                  75                  80

Leu Arg Ile Trp Pro Ile Ser Ile Asn Tyr Arg Thr
                85                  90

```
<210> SEQ ID NO 74
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Val Ser Asp Val Pro Arg Asp Leu Glu Val Val Ala Ala Thr Pro Thr
1               5                   10                  15

Ser Leu Leu Ile Ser Trp Pro Lys Arg Pro Met Asn Met Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Ala Tyr Thr Ala Thr Ile Ser Gly Leu Lys Pro
    50                  55                  60

Gly Val Asp Tyr Thr Ile Thr Val Tyr Ala Val Thr Tyr Leu Tyr Ala
65                  70                  75                  80

Thr Tyr Val Met His Gln Pro Ile Ser Ile Asn Tyr Arg Thr
                85                  90

<210> SEQ ID NO 75
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Val Ser Asp Val Pro Arg Asp Leu Glu Val Val Ala Ala Thr Pro Thr
1               5                   10                  15

Ser Leu Leu Ile Ser Trp Ser Tyr Asp Gln Ser Arg Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Met Tyr Pro Thr Ala Thr Ile Ser Gly Leu Lys Pro
    50                  55                  60

Gly Val Asp Tyr Thr Ile Thr Val Tyr Ala Val Thr Glu Arg Asp Arg
65                  70                  75                  80

Tyr Ser Tyr Met His His Pro Ile Ser Ile Asn Tyr Arg Thr
                85                  90

<210> SEQ ID NO 76
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Val Ser Asp Val Pro Arg Asp Leu Glu Val Val Ala Ala Thr Pro Thr
1               5                   10                  15

Ser Leu Leu Ile Ser Trp Pro Phe Gln Ala Val Ser Asn Arg Tyr Tyr
            20                  25                  30

Arg Ile Thr Tyr Gly Glu Thr Gly Gly Asn Ser Pro Val Gln Glu Phe
```

```
                35                  40                  45
Thr Val Pro Ala Phe Pro Asn Thr Ala Thr Ile Ser Gly Leu Lys Pro
         50                  55                  60
Gly Val Asp Tyr Thr Ile Thr Val Tyr Ala Val Thr Lys Met Arg Asp
 65                  70                  75                  80
Tyr Arg Pro Ile Ser Ile Asn Tyr Arg Thr
                 85                  90
```

<210> SEQ ID NO 77
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

```
Val Ser Asp Val Pro Arg Asp Leu Glu Val Val Ala Ala Thr Pro Thr
  1               5                  10                  15
Ser Leu Leu Ile Ser Trp Tyr His Asp Met His Arg Ser Arg Tyr Tyr
                 20                  25                  30
Arg Ile Thr Tyr Gly Glu Thr Gly Gly Asn Ser Pro Val Gln Glu Phe
             35                  40                  45
Thr Val Pro Ser Tyr Tyr Pro Thr Ala Thr Ile Ser Gly Leu Lys Pro
         50                  55                  60
Gly Val Asp Tyr Thr Ile Thr Val Tyr Ala Val Thr Lys Gly Ser Gly
 65                  70                  75                  80
Tyr Gln Val Met His Thr Pro Ile Ser Ile Asn Tyr Arg Thr
                 85                  90
```

<210> SEQ ID NO 78
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

```
Val Ser Asp Val Pro Arg Asp Leu Glu Val Val Ala Ala Thr Pro Thr
  1               5                  10                  15
Ser Leu Leu Ile Ser Trp Ala Tyr Tyr Met Gly Gly Tyr Arg Tyr Tyr
                 20                  25                  30
Arg Ile Thr Tyr Gly Glu Thr Gly Gly Asn Ser Pro Val Gln Glu Phe
             35                  40                  45
Thr Val Pro Gly Ser Tyr Pro Thr Ala Thr Ile Ser Gly Leu Lys Pro
         50                  55                  60
Gly Val Asp Tyr Thr Ile Thr Val Tyr Ala Val Thr Asp Arg Lys His
 65                  70                  75                  80
Tyr Met Tyr Tyr His His Pro Ile Ser Ile Asn Tyr Arg Thr
                 85                  90
```

<210> SEQ ID NO 79
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 79

Val Ser Asp Val Pro Arg Asp Leu Glu Val Val Ala Ala Thr Pro Thr
1               5                   10                  15

Ser Leu Leu Ile Ser Trp Tyr Tyr Met Pro His Arg Asn Arg Tyr Tyr
            20                  25                  30

Arg Ile Thr Tyr Gly Glu Thr Gly Asn Ser Pro Val Gln Glu Phe
        35                  40                  45

Thr Val Pro Ser Thr Tyr Pro Thr Ala Thr Ile Ser Gly Leu Lys Pro
    50                  55                  60

Gly Val Asp Tyr Thr Ile Thr Val Tyr Ala Val Thr Asn His His Val
65                  70                  75                  80

His Arg Leu Met His Ile Pro Ile Ser Ile Asn Tyr Arg Thr
                85                  90

<210> SEQ ID NO 80
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Val Ser Asp Val Pro Arg Asp Leu Glu Val Val Ala Ala Thr Pro Thr
1               5                   10                  15

Ser Leu Leu Ile Ser Trp His Glu Asp Pro Ser Thr Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Tyr Tyr Pro Thr Ala Thr Ile Ser Gly Leu Lys Pro
    50                  55                  60

Gly Val Asp Tyr Thr Ile Thr Val Tyr Ala Val Thr Asp Tyr His Glu
65                  70                  75                  80

Leu Val Tyr Met His His Pro Ile Ser Ile Asn Tyr Arg Thr
                85                  90

<210> SEQ ID NO 81
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Val Ser Asp Val Pro Arg Asp Leu Glu Val Val Ala Ala Thr Pro Thr
1               5                   10                  15

Ser Leu Leu Ile Ser Trp Asp Glu Ile Glu Phe Pro Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Pro Arg Gly Thr Ala Thr Ile Ser Gly Leu Lys Pro
    50                  55                  60

Gly Val Asp Tyr Thr Ile Thr Val Tyr Ala Val Thr Met His Tyr Tyr
65                  70                  75                  80

Leu Arg Val Trp Pro Ile Ser Ile Asn Tyr Arg Thr
            85                  90

<210> SEQ ID NO 82
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Val Ser Asp Val Pro Arg Asp Leu Glu Val Val Ala Ala Thr Pro Thr
1               5                   10                  15

Ser Leu Leu Ile Ser Trp Ser Thr His Phe Thr Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Val Asn Tyr Thr Ala Thr Ile Ser Gly Leu Lys Pro
    50                  55                  60

Gly Val Asp Tyr Thr Ile Thr Val Tyr Ala Val Thr His Ser Arg Pro
65                  70                  75                  80

Arg His Tyr His Pro Ile Ser Ile Asn Tyr Arg Thr
            85                  90

<210> SEQ ID NO 83
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Val Ser Asp Val Pro Arg Asp Leu Glu Val Val Ala Ala Thr Pro Thr
1               5                   10                  15

Ser Leu Leu Ile Ser Trp Gly Lys His Ile Arg Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro His Asn Ser Val Thr Ala Thr Ile Ser Gly Leu Lys Pro
    50                  55                  60

Gly Val Asp Tyr Thr Ile Thr Val Tyr Ala Val Thr Val Ala Tyr Asn
65                  70                  75                  80

Tyr Leu Arg Asp Tyr Lys Pro Ile Ser Ile Asn Tyr Arg Thr
            85                  90

<210> SEQ ID NO 84
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Val Ser Asp Val Pro Arg Asp Leu Glu Val Val Ala Ala Thr Pro Thr
1               5                   10                  15

Ser Leu Leu Ile Ser Trp His Ser Asn Leu Leu Val Gln Arg Tyr Tyr

```
                    20                  25                  30

Arg Ile Thr Tyr Gly Glu Thr Gly Gly Asn Ser Pro Val Gln Glu Phe
                35                  40                  45

Thr Val Pro Ser Ser Ala Val Thr Ala Thr Ile Ser Gly Leu Lys Pro
    50                  55                  60

Gly Val Asp Tyr Thr Ile Thr Val Tyr Ala Val Thr Pro Gly His Leu
65                  70                  75                  80

Arg Lys Tyr Gly Pro Ile Ser Ile Asn Tyr Arg Thr
                85                  90

<210> SEQ ID NO 85
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Val Ser Asp Val Pro Arg Asp Leu Glu Val Val Ala Ala Thr Pro Thr
1               5                   10                  15

Ser Leu Leu Ile Ser Trp Asp Tyr Asp Arg Ser Lys Tyr Arg Tyr Tyr
                20                  25                  30

Arg Ile Thr Tyr Gly Glu Thr Gly Gly Asn Ser Pro Val Gln Glu Phe
                35                  40                  45

Thr Val Pro Ala Ser Tyr Pro Thr Ala Thr Ile Ser Gly Leu Lys Pro
    50                  55                  60

Gly Val Asp Tyr Thr Ile Thr Val Tyr Ala Val Thr Gln Lys Asp Ile
65                  70                  75                  80

Tyr Tyr Tyr Ile Tyr Tyr Pro Ile Ser Ile Asn Tyr Arg Thr
                85                  90

<210> SEQ ID NO 86
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Val Ser Asp Val Pro Arg Asp Leu Glu Val Val Ala Ala Thr Pro Thr
1               5                   10                  15

Ser Leu Leu Ile Ser Trp Gly Asp Glu Leu Val Ala Ala Arg Tyr Tyr
                20                  25                  30

Arg Ile Thr Tyr Gly Glu Thr Gly Gly Asn Ser Pro Val Gln Glu Phe
                35                  40                  45

Thr Val Pro Ser Phe Asn Asp Thr Ala Thr Ile Ser Gly Leu Lys Pro
    50                  55                  60

Gly Val Asp Tyr Thr Ile Thr Val Tyr Ala Val Thr His Leu Leu Gly
65                  70                  75                  80

Thr Leu Trp Leu Ile Pro Pro Ile Ser Ile Asn Tyr Arg Thr
                85                  90

<210> SEQ ID NO 87
<211> LENGTH: 92
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 87

Val Ser Asp Val Pro Arg Asp Leu Glu Val Val Ala Ala Thr Pro Thr
1               5                   10                  15

Ser Leu Leu Ile Ser Trp Ser Leu Tyr Leu Arg Val Lys Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Asn Ala Met Thr Ala Thr Ile Ser Gly Leu Lys Pro
    50                  55                  60

Gly Val Asp Tyr Thr Ile Thr Val Tyr Ala Val Thr Ser Pro Ser Leu
65                  70                  75                  80

Arg Gly Tyr Gly Pro Ile Ser Ile Asn Tyr Arg Thr
                85                  90

<210> SEQ ID NO 88
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Val Ser Asp Val Pro Arg Asp Leu Glu Val Val Ala Ala Thr Pro Thr
1               5                   10                  15

Ser Leu Leu Ile Ser Trp Ala Tyr Asp Met His Arg Lys Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Ser Lys Tyr Ser
65                  70                  75                  80

Gly His Tyr Val His Asn Pro Ile Ser Ile Asn Tyr Arg Thr
                85                  90

<210> SEQ ID NO 89
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Val Ser Asp Val Pro Arg Asp Leu Glu Val Val Ala Ala Thr Pro Thr
1               5                   10                  15

Ser Leu Leu Ile Ser Trp Leu Asp Leu Ser Leu Lys Met Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser His His Gln Thr Ala Thr Ile Ser Gly Leu Lys Pro
    50                  55                  60
```

```
Gly Val Asp Tyr Thr Ile Thr Val Tyr Ala Val Thr Glu Tyr Ala Ala
65                  70                  75                  80

Tyr Arg Met Met His Ile Pro Ile Ser Ile Asn Tyr Arg Thr
                85                  90
```

<210> SEQ ID NO 90
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

```
Val Ser Asp Val Pro Arg Asp Leu Glu Val Val Ala Ala Thr Pro Thr
1               5                   10                  15

Ser Leu Leu Ile Ser Trp Gly Leu Ile Leu Gly Arg Asp Arg Tyr Tyr
                20                  25                  30

Arg Ile Thr Tyr Gly Glu Thr Gly Gly Asn Ser Pro Val Gln Glu Phe
                35                  40                  45

Thr Val Pro Ala Phe Pro Phe Thr Ala Thr Ile Ser Gly Leu Lys Pro
        50                  55                  60

Gly Val Asp Tyr Thr Ile Thr Val Tyr Ala Val Thr Tyr Arg Gly Phe
65                  70                  75                  80

Asp Thr Phe Phe Pro Asn Pro Ile Ser Ile Asn Tyr Arg Thr
                85                  90
```

<210> SEQ ID NO 91
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 91

```
Val Ser Asp Val Pro Arg Asp Leu Glu Val Val Ala Ala Thr Pro Thr
1               5                   10                  15

Ser Leu Leu Ile Ser Trp Leu Pro Ser Pro Ala Ile Thr Arg Tyr Tyr
                20                  25                  30

Arg Ile Thr Tyr Gly Glu Thr Gly Gly Asn Ser Pro Val Gln Glu Phe
                35                  40                  45

Thr Val Pro Asp Pro Leu Ser Thr Ala Thr Ile Ser Gly Leu Lys Pro
        50                  55                  60

Gly Val Asp Tyr Thr Ile Thr Val Tyr Ala Val Thr Tyr Arg Tyr Ser
65                  70                  75                  80

Thr Trp Pro Ile Ser Ile Asn Tyr Arg Thr
                85                  90
```

<210> SEQ ID NO 92
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 92

```
Val Ser Asp Val Pro Arg Asp Leu Glu Val Val Ala Ala Thr Pro Thr
```

```
                1               5                   10                  15
        Ser Leu Leu Ile Ser Trp Val Tyr Glu Asn Asn Arg Gln Arg Tyr Tyr
                        20                  25                  30

Arg Ile Thr Tyr Gly Glu Thr Gly Asn Ser Pro Val Gln Glu Phe
                        35                  40                  45

Thr Val Pro Ser Tyr Tyr Pro Thr Ala Thr Ile Ser Gly Leu Lys Pro
                50                      55                  60

Gly Val Asp Tyr Thr Ile Thr Val Tyr Ala Val Thr Gln Gln Ser Gln
        65                      70                  75                  80

His Ala Tyr Tyr His Leu Pro Ile Ser Ile Asn Tyr Arg Thr
                        85                  90
```

<210> SEQ ID NO 93
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

```
        Val Ser Asp Val Pro Arg Asp Leu Glu Val Val Ala Ala Thr Pro Thr
        1               5                   10                  15

Ser Leu Leu Ile Ser Trp Val Glu Phe His Lys Pro Asp Arg Tyr Tyr
                        20                  25                  30

Arg Ile Thr Tyr Gly Glu Thr Gly Gly Asn Ser Pro Val Gln Glu Phe
                        35                  40                  45

Thr Val Pro Ala Glu Gln Gly Thr Ala Thr Ile Ser Gly Leu Lys Pro
                50                      55                  60

Gly Val Asp Tyr Thr Ile Thr Val Tyr Ala Val Thr Glu Tyr Ala Ala
        65                      70                  75                  80

Tyr Arg Met Met His Ile Pro Ile Ser Ile Asn Tyr Arg Thr
                        85                  90
```

<210> SEQ ID NO 94
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

```
        Val Ser Asp Val Pro Arg Asp Leu Glu Val Val Ala Ala Thr Pro Thr
        1               5                   10                  15

Ser Leu Leu Ile Ser Trp Asp Glu Ile Glu Phe Pro Val Arg Tyr Tyr
                        20                  25                  30

Arg Ile Thr Tyr Gly Glu Thr Gly Gly Asn Ser Pro Val Gln Glu Phe
                        35                  40                  45

Thr Val Pro Gly Pro Arg Gly Thr Ala Thr Ile Ser Gly Leu Lys Pro
                50                      55                  60

Gly Val Asp Tyr Thr Ile Thr Val Tyr Ala Val Thr Met His Tyr Tyr
        65                      70                  75                  80

Leu Arg Val Trp Pro Ile Ser Ile Asn Tyr Arg Thr
                        85                  90
```

<210> SEQ ID NO 95

```
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Val Ser Asp Val Pro Arg Asp Leu Glu Val Val Ala Ala Thr Pro Thr
1               5                   10                  15

Ser Leu Leu Ile Ser Trp Ser Tyr Asn Met Lys Pro Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Asp Arg Tyr Met
65                  70                  75                  80

Tyr Arg Met Leu His Lys Pro Ile Ser Ile Asn Tyr Arg Thr
                85                  90

<210> SEQ ID NO 96
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Val Ser Asp Val Pro Arg Asp Leu Glu Val Val Ala Ala Thr Pro Thr
1               5                   10                  15

Ser Leu Leu Ile Ser Trp Tyr Tyr Glu His Ile Arg Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Gly Tyr Gly Gln
65                  70                  75                  80

Tyr Tyr Tyr Tyr His Ser Pro Ile Ser Ile Asn Tyr Arg Thr
                85                  90

<210> SEQ ID NO 97
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Val Ser Asp Val Pro Arg Asp Leu Glu Val Val Ala Ala Thr Pro Thr
1               5                   10                  15

Ser Leu Leu Ile Ser Trp Tyr Asn Asp Pro Arg Arg Asn Arg Tyr Tyr
            20                  25                  30

Arg Ile Thr Tyr Gly Glu Thr Gly Gly Asn Ser Pro Val Gln Glu Phe
        35                  40                  45
```

```
Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Tyr Arg Tyr Ser
 65                  70                  75                  80

Tyr Gln Tyr Gln His Ala Pro Ile Ser Ile Asn Tyr Arg Thr
                 85                  90
```

<210> SEQ ID NO 98
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

```
Val Ser Asp Val Pro Arg Asp Leu Glu Val Val Ala Ala Thr Pro Thr
 1               5                  10                  15

Ser Leu Leu Ile Ser Trp Tyr Tyr Asp Asp His Ala Gln Arg Tyr Tyr
                 20                  25                  30

Arg Ile Thr Tyr Gly Glu Thr Gly Gly Asn Ser Pro Val Gln Glu Phe
             35                  40                  45

Thr Val Pro Ser Thr Tyr Pro Thr Ala Thr Ile Ser Gly Leu Lys Pro
    50                  55                  60

Gly Val Asp Tyr Thr Ile Thr Val Tyr Ala Val Thr Val Arg Gly Val
 65                  70                  75                  80

Tyr Tyr Tyr Tyr Tyr Gln Pro Ile Ser Ile Asn Tyr Arg Thr
                 85                  90
```

<210> SEQ ID NO 99
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

```
Val Ser Asp Val Pro Arg Asp Leu Glu Val Val Ala Ala Thr Pro Thr
 1               5                  10                  15

Ser Leu Leu Ile Ser Trp Ile Pro Thr Ser Lys Asn Gly Arg Tyr Tyr
                 20                  25                  30

Arg Ile Thr Tyr Gly Glu Thr Gly Gly Asn Ser Pro Val Gln Glu Phe
             35                  40                  45

Thr Val Pro Ser Tyr Tyr Pro Thr Ala Thr Ile Ser Gly Leu Lys Pro
    50                  55                  60

Gly Val Asp Tyr Thr Ile Thr Val Tyr Ala Val Thr Glu Val Gln His
 65                  70                  75                  80

Tyr Arg Tyr Leu His Ala Pro Ile Ser Ile Asn Tyr Arg Thr
                 85                  90
```

<210> SEQ ID NO 100
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

```
Val Ser Asp Val Pro Arg Asp Leu Glu Val Val Ala Ala Thr Pro Thr
1               5                   10                  15

Ser Leu Leu Ile Ser Trp Pro Thr His Tyr Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Tyr Tyr Pro Thr Ala Thr Ile Ser Gly Leu Lys Pro
    50                  55                  60

Gly Val Asp Tyr Thr Ile Thr Val Tyr Ala Val Thr Glu His Ser His
65                  70                  75                  80

Val Arg Arg Met His Val Pro Ile Ser Ile Asn Tyr Arg Thr
                85                  90
```

<210> SEQ ID NO 101
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

```
Val Ser Asp Val Pro Arg Asp Leu Glu Val Val Ala Ala Thr Pro Thr
1               5                   10                  15

Ser Leu Leu Ile Ser Trp Leu Met Lys Leu Tyr Leu Glu Arg Tyr Tyr
            20                  25                  30

Arg Ile Thr Tyr Gly Glu Thr Gly Gly Asn Ser Pro Val Gln Glu Phe
        35                  40                  45

Thr Val Pro Pro Ser Tyr Ile Thr Ala Thr Ile Ser Gly Leu Lys Pro
    50                  55                  60

Gly Val Asp Tyr Thr Ile Thr Val Tyr Ala Val Thr Tyr His Glu Ser
65                  70                  75                  80

Gln Glu Gly Ala Gly His Pro Ile Ser Ile Asn Tyr Arg Thr
                85                  90
```

<210> SEQ ID NO 102
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

```
Val Ser Asp Val Pro Arg Asp Leu Glu Val Val Ala Ala Thr Pro Thr
1               5                   10                  15

Ser Leu Leu Ile Ser Trp Glu Tyr Val Glu Tyr Thr His Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Val His Tyr Thr Ala Thr Ile Ser Gly Leu Lys Pro
    50                  55                  60

Gly Val Asp Tyr Thr Ile Thr Val Tyr Ala Val Thr Tyr Met Asp Thr
65                  70                  75                  80

Ser Met Tyr Val Ser Ser Pro Ile Ser Ile Asn Tyr Arg Thr
                85                  90
```

```
<210> SEQ ID NO 103
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Val Ser Asp Val Pro Arg Asp Leu Glu Val Val Ala Ala Thr Pro Thr
1               5                   10                  15

Ser Leu Leu Ile Ser Trp Lys Tyr Asp Ser Tyr Ser Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Tyr Gln Ser Ile
65                  70                  75                  80

Tyr Tyr Tyr Met His Ser Pro Ile Ser Ile Asn Tyr Arg Thr
                85                  90

<210> SEQ ID NO 104
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Val Ser Asp Val Pro Arg Asp Leu Glu Val Val Ala Ala Thr Pro Thr
1               5                   10                  15

Ser Leu Leu Ile Ser Trp Glu Tyr Asp Gly Pro Ala Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Tyr Pro Thr Ala Thr Ile Ser Gly Leu Lys Pro
    50                  55                  60

Gly Val Asp Tyr Thr Ile Thr Val Tyr Ala Val Thr Gln Thr Asn Met
65                  70                  75                  80

His Tyr Leu Met His Tyr Pro Ile Ser Ile Asn Tyr Arg Thr
                85                  90

<210> SEQ ID NO 105
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Val Ser Asp Val Pro Arg Asp Leu Glu Val Val Ala Ala Thr Pro Thr
1               5                   10                  15

Ser Leu Leu Ile Ser Trp Asp Tyr Asp Arg Ser Lys Tyr Arg Tyr Tyr
            20                  25                  30
```

Arg Ile Thr Tyr Gly Glu Thr Gly Gly Asn Ser Pro Val Gln Glu Phe
            35                  40                  45

Thr Val Pro Ala Ser Tyr Pro Thr Ala Thr Ile Ser Gly Leu Lys Pro
 50                  55                  60

Gly Val Asp Tyr Thr Ile Thr Val Tyr Ala Val Thr Gln Lys Asp Ile
 65                  70                  75                  80

Tyr Tyr Tyr Ile Tyr Asn Pro Ile Ser Ile Asn Tyr Arg Thr
                85                  90

<210> SEQ ID NO 106
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Val Ser Asp Val Pro Arg Asp Leu Glu Val Val Ala Ala Thr Pro Thr
 1               5                  10                  15

Ser Leu Leu Ile Ser Trp Tyr Tyr Met Pro His Arg Asn Arg Tyr Tyr
                20                  25                  30

Arg Ile Thr Tyr Gly Glu Thr Gly Gly Asn Ser Pro Val Gln Glu Phe
            35                  40                  45

Thr Val Pro Ser Thr Tyr Pro Thr Ala Thr Ile Ser Gly Leu Lys Pro
 50                  55                  60

Gly Val Asp Tyr Thr Ile Thr Val Tyr Ala Val Thr Asn His His Val
 65                  70                  75                  80

His Arg Leu Met His Ile Pro Ile Ser Ile Asn Tyr Arg Thr
                85                  90

<210> SEQ ID NO 107
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Val Ser Asp Val Pro Arg Asp Leu Glu Val Val Ala Ala Thr Pro Thr
 1               5                  10                  15

Ser Leu Leu Ile Ser Trp Ser Ser His Leu Pro Tyr Asp Arg Tyr Tyr
                20                  25                  30

Arg Ile Thr Tyr Gly Glu Thr Gly Gly Asn Ser Pro Val Gln Glu Phe
            35                  40                  45

Thr Val Pro Lys Tyr Lys Thr Ala Thr Ile Ser Gly Leu Lys Pro Gly
 50                  55                  60

Val Asp Tyr Thr Ile Thr Val Tyr Ala Val Thr Thr Lys Gly Val His
 65                  70                  75                  80

Tyr Leu Phe His Ser Pro Ile Ser Ile Asn Tyr Arg Thr
                85                  90

<210> SEQ ID NO 108
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Val Ser Asp Val Pro Arg Asp Leu Glu Val Val Ala Ala Thr Pro Thr
1               5                   10                  15

Ser Leu Leu Ile Ser Trp Gln Tyr Asp Arg Ser Ser Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Ala Ser Tyr Pro Thr Ala Thr Ile Ser Gly Leu Lys Pro
    50                  55                  60

Gly Val Asp Tyr Thr Ile Thr Val Tyr Ala Val Thr Arg Val Gly Thr
65                  70                  75                  80

Tyr Gln Tyr Tyr Tyr Leu Pro Ile Ser Ile Asn Tyr Arg Thr
                85                  90

<210> SEQ ID NO 109
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Val Ser Asp Val Pro Arg Asp Leu Glu Val Val Ala Ala Thr Pro Thr
1               5                   10                  15

Ser Leu Leu Ile Ser Trp Tyr Thr Pro Tyr Lys Tyr Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser His Ser Thr Ala Thr Ile Ser Gly Leu Lys Pro Gly
    50                  55                  60

Val Asp Tyr Thr Ile Thr Val Tyr Ala Val Thr Val Gly Asn Met Tyr
65                  70                  75                  80

Leu Ser Ile Val Pro Ile Ser Ile Asn Tyr Arg Thr
                85                  90

<210> SEQ ID NO 110
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Val Ser Asp Val Pro Arg Asp Leu Glu Val Val Ala Ala Thr Pro Thr
1               5                   10                  15

Ser Leu Leu Ile Ser Trp Ser Asp Ser Leu Lys Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Gln Tyr His Thr Ala Thr Ile Ser Gly Leu Lys Pro
    50                  55                  60

Gly Val Asp Tyr Thr Ile Thr Val Tyr Ala Val Thr Pro Ser Asn Ile
65                  70                  75                  80

```
Ile Gly Arg His Tyr Gly Pro Ile Ser Ile Asn Tyr Arg Thr
                85                  90
```

<210> SEQ ID NO 111
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

```
Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90
```

<210> SEQ ID NO 112
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

```
Val Ser Asp Val Pro Arg Asp Leu Glu Val Val Ala Ala Thr Pro Thr
1               5                   10                  15

Ser Leu Leu Ile Ser Trp Ser Thr Ala Leu Lys Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys His Ser His Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90
```

<210> SEQ ID NO 113
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

```
Val Ser Asp Val Pro Arg Asp Leu Glu Val Val Ala Ala Thr Pro Thr
1               5                   10                  15
```

Ser Leu Leu Ile Ser Trp Pro Thr His Tyr Lys Val Ala Arg Tyr Tyr
            20                  25                  30

Arg Ile Thr Tyr Gly Glu Thr Gly Gly Asn Ser Pro Val Gln Glu Phe
            35                  40                  45

Thr Val Pro Lys His Thr Tyr Thr Ala Thr Ile Ser Gly Leu Lys Pro
        50                  55                  60

Gly Val Asp Tyr Thr Ile Thr Val Tyr Ala Val Thr Thr Thr Lys Gly
65                  70                  75                  80

Leu Arg His Tyr Gly Pro Ile Ser Ile Asn Tyr Arg Thr
                85                  90

<210> SEQ ID NO 114
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Val Ser Asp Val Pro Arg Asp Leu Glu Val Val Ala Ala Thr Pro Thr
1               5                   10                  15

Ser Leu Leu Ile Ser Trp Ser Asp Lys Leu Lys Val Gln Arg Tyr Tyr
            20                  25                  30

Arg Ile Thr Tyr Gly Glu Thr Gly Gly Asn Ser Pro Val Gln Glu Phe
            35                  40                  45

Thr Val Pro Lys His Asp Arg Thr Ala Thr Ile Ser Gly Leu Lys Pro
        50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 115
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Val Ser Asp Val Pro Arg Asp Leu Glu Val Val Ala Ala Thr Pro Thr
1               5                   10                  15

Ser Leu Leu Ile Ser Trp Ser Lys Arg Leu Gln Val Ser Arg Tyr Tyr
            20                  25                  30

Arg Ile Thr Tyr Gly Glu Thr Gly Gly Asn Ser Pro Val Gln Glu Phe
            35                  40                  45

Thr Val Pro Tyr Asn Tyr Lys Thr Ala Thr Ile Ser Gly Leu Lys Pro
        50                  55                  60

Gly Val Asp Tyr Thr Ile Thr Val Tyr Ala Val Thr Pro Ser Asn Ile
65                  70                  75                  80

Ile Gly Arg His Tyr Gly Pro Ile Ser Ile Asn Tyr Arg Thr
                85                  90

<210> SEQ ID NO 116
<211> LENGTH: 94
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Val Ser Asp Val Pro Arg Asp Leu Glu Val Val Ala Ala Thr Pro Thr
1               5                   10                  15

Ser Leu Leu Ile Ser Trp Ser Asn Arg Leu Val Val Lys Arg Tyr Tyr
            20                  25                  30

Arg Ile Thr Tyr Gly Glu Thr Gly Gly Asn Ser Pro Val Gln Glu Phe
        35                  40                  45

Thr Val Pro His Gln Met Lys Thr Ala Thr Ile Ser Gly Leu Lys Pro
    50                  55                  60

Gly Val Asp Tyr Thr Ile Thr Val Tyr Ala Val Thr Pro Gly Gly Tyr
65                  70                  75                  80

Ser Gly Arg Asn Tyr Gly Pro Ile Ser Ile Asn Tyr Arg Thr
                85                  90

<210> SEQ ID NO 117
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Val Ser Asp Val Pro Arg Asp Leu Glu Val Val Ala Ala Thr Pro Thr
1               5                   10                  15

Ser Leu Leu Ile Ser Trp Ser Glu Asn Leu Arg Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Ser Ser Val His Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 118
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Val Ser Asp Val Pro Arg Asp Leu Glu Val Val Ala Ala Thr Pro Thr
1               5                   10                  15

Ser Leu Leu Ile Ser Trp Ser Ser Asn Leu Val Val Lys Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asp Pro Ser Thr Ala Thr Ile Ser Gly Leu Lys Pro
    50                  55                  60
```

Gly Val Asp Tyr Thr Ile Thr Val Tyr Ala Val Thr Asp Tyr Glu Met
65                  70                  75                  80

Lys Pro Arg Asn Tyr Gly Pro Ile Ser Ile Asn Tyr Arg Thr
                85                  90

<210> SEQ ID NO 119
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Val Ser Asp Val Pro Arg Asp Leu Glu Val Val Ala Ala Thr Pro Thr
1               5                   10                  15

Ser Leu Leu Ile Ser Trp Pro Thr His Tyr Lys Val Ala Arg Tyr Tyr
                20                  25                  30

Arg Ile Thr Tyr Gly Glu Thr Gly Gly Asn Ser Pro Val Gln Glu Phe
            35                  40                  45

Thr Val Pro Lys His Glu Ser Thr Ala Thr Ile Ser Gly Leu Lys Pro
        50                  55                  60

Gly Val Asp Tyr Thr Ile Thr Val Tyr Ala Val Thr Leu Asn Val Ala
65                  70                  75                  80

Tyr Ser Arg Glu Val Arg Pro Ile Ser Ile Asn Tyr Arg Thr
                85                  90

<210> SEQ ID NO 120
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Val Ser Asp Val Pro Arg Asp Leu Glu Val Val Ala Ala Thr Pro Thr
1               5                   10                  15

Ser Leu Leu Ile Ser Trp Pro Asp His Val Lys Val Gln Arg Tyr Tyr
                20                  25                  30

Arg Ile Thr Tyr Gly Glu Thr Gly Gly Asn Ser Pro Val Gln Glu Phe
            35                  40                  45

Thr Val Pro Gln His Ser Arg Thr Ala Thr Ile Ser Gly Leu Lys Pro
        50                  55                  60

Gly Val Asp Tyr Thr Ile Thr Val Tyr Ala Val Thr Tyr Thr Gly Tyr
65                  70                  75                  80

Gly Thr Glu Arg Asn Tyr Gln Pro Ile Ser Ile Asn Tyr Arg Thr
                85                  90                  95

<210> SEQ ID NO 121
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Val Ser Asp Val Pro Arg Asp Leu Glu Val Val Ala Ala Thr Pro Thr
1               5                   10                  15

Ser Leu Leu Ile Ser Trp Gly Ser His Leu Arg Val Ser Arg Tyr Tyr
            20                  25                  30

Arg Ile Thr Tyr Gly Glu Thr Gly Gly Asn Ser Pro Val Gln Glu Phe
            35                  40                  45

Thr Val Pro Tyr Asp Ser His Thr Ala Thr Ile Ser Gly Leu Lys Pro
        50                  55                  60

Gly Val Asp Tyr Thr Ile Thr Val Tyr Ala Val Thr Gln Gly Pro Asn
65                  70                  75                  80

Arg Gly Arg Asn Tyr Gln Pro Ile Ser Ile Asn Tyr Arg Thr
                85                  90

<210> SEQ ID NO 122
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Val Ser Asp Val Pro Arg Asp Leu Glu Val Val Ala Ala Thr Pro Thr
1               5                   10                  15

Ser Leu Leu Ile Ser Trp Gly Lys His Leu Val Val Gln Arg Tyr Tyr
            20                  25                  30

Arg Ile Thr Tyr Gly Glu Thr Gly Gly Asn Ser Pro Val Gln Glu Phe
            35                  40                  45

Thr Val Pro Arg Gly His Tyr Thr Ala Thr Ile Ser Gly Leu Lys Pro
        50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 123
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Val Ser Asp Val Pro Arg Asp Leu Glu Val Val Ala Ala Thr Pro Thr
1               5                   10                  15

Ser Leu Leu Ile Ser Trp Thr Thr Asn Leu Gln Val Ser Arg Tyr Tyr
            20                  25                  30

Arg Ile Thr Tyr Gly Glu Thr Gly Gly Asn Ser Pro Val Gln Glu Phe
            35                  40                  45

Thr Val Pro Lys Ala Asn Thr Thr Ala Thr Ile Ser Gly Leu Lys Pro
        50                  55                  60

Gly Val Asp Tyr Thr Ile Thr Val Tyr Ala Val Thr Val Ser Lys Gly
65                  70                  75                  80

Asn Arg Ser Tyr Gly Pro Ile Ser Ile Asn Tyr Arg Thr
                85                  90

-continued

<210> SEQ ID NO 124
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Val Ser Asp Val Pro Arg Asp Leu Glu Val Val Ala Ala Thr Pro Thr
1               5                   10                  15

Ser Leu Leu Ile Ser Trp Ala Glu His Leu Gln Val Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Arg Gly Val Tyr Thr Ala Thr Ile Ser Gly Leu Lys Pro
    50                  55                  60

Gly Val Asp Tyr Thr Ile Thr Val Tyr Ala Val Thr Pro Ser Asn Ile
65                  70                  75                  80

Ile Gly Arg His Tyr Gly Pro Ile Ser Ile Asn Tyr Arg Thr
                85                  90

<210> SEQ ID NO 125
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Val Ser Asp Val Pro Arg Asp Leu Glu Val Val Ala Ala Thr Pro Thr
1               5                   10                  15

Ser Leu Leu Ile Ser Trp Pro Gln His Leu Arg Val Gln Arg Tyr Tyr
            20                  25                  30

Arg Ile Thr Tyr Gly Glu Thr Gly Gly Asn Ser Pro Val Gln Glu Phe
        35                  40                  45

Thr Val Pro Arg Gly Ser Asp Thr Ala Thr Ile Ser Gly Leu Lys Pro
    50                  55                  60

Gly Val Asp Tyr Thr Ile Thr Val Tyr Ala Val Thr Lys Met Arg Asp
65                  70                  75                  80

Tyr Arg Pro Ile Ser Ile Asn Tyr Arg Thr
                85                  90

<210> SEQ ID NO 126
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

```
Thr Val Pro Leu Gln Pro Pro Thr Ala Thr Ile Ser Gly Leu Lys Pro
 50                  55                  60

Gly Val Asp Tyr Thr Ile Thr Val Tyr Ala Val Thr Glu Gly Pro Asn
 65                  70                  75                  80

Glu Arg Ser Leu Phe Ile Pro Ile Ser Ile Asn Tyr Arg Thr
                 85                  90

<210> SEQ ID NO 127
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
                 20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Val
 50                  55                  60

Tyr Ala Val Thr Glu Gly Pro Asn Glu Arg Ser Leu Phe Ile Pro Ile
 65                  70                  75                  80

Ser Ile Asn Tyr Arg Thr
                 85

<210> SEQ ID NO 128
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Gly Glu Val Val Ala Ala Thr Pro Thr Ser Leu Leu Ile Ser Trp Arg
  1               5                  10                  15

His Pro His Phe Pro Thr Arg Tyr Tyr Arg Ile Thr Tyr Gly Glu Thr
                 20                  25                  30

Gly Gly Asn Ser Pro Val Gln Glu Phe Thr Val Pro Leu Gln Pro Pro
             35                  40                  45

Thr Ala Thr Ile Ser Gly Leu Lys Pro Gly Val Asp Tyr Thr Ile Thr
 50                  55                  60

Val Tyr Ala Val Thr Asp Gly Arg Asn Gly Arg Leu Leu Ser Ile Pro
 65                  70                  75                  80

Ile Ser Ile Asn Tyr Arg Thr Glu Ile Asp Lys Pro Cys Gln
                 85                  90

<210> SEQ ID NO 129
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 129

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Val
    50                  55                  60

Tyr Ala Val Thr Asp Gly Arg Asn Gly Arg Leu Leu Ser Ile Pro Ile
65                  70                  75                  80

Ser Ile Asn Tyr Arg Thr
                85

<210> SEQ ID NO 130
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Gly Leu Tyr Gly His Glu Leu Leu Thr Pro Ile
65                  70                  75                  80

Ser Ile Asn Tyr Arg Thr
                85

<210> SEQ ID NO 131
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Glu Asn Gly Gln Phe Leu Leu Val Pro Ile
65                  70                  75                  80

Ser Ile Asn Tyr Arg Thr

```
                85

<210> SEQ ID NO 132
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Glu Val Val Ala Ala Thr Pro Thr Ser Leu Leu Ile Ser Trp Arg His
1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Met Gly Pro Asn Asp Asn Glu Leu Leu Thr Pro Ile
65                  70                  75                  80

Ser Ile Asn Tyr Arg Thr
                85

<210> SEQ ID NO 133
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Glu Val Val Ala Ala Thr Pro Thr Ser Leu Leu Ile Ser Trp Arg His
1               5                  10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Ala Gly Trp Asp Asp His Glu Leu Phe Ile Pro Ile
65                  70                  75                  80

Ser Ile Asn Tyr Arg Thr
                85

<210> SEQ ID NO 134
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Glu Val Val Ala Ala Thr Pro Thr Ser Leu Leu Ile Ser Trp Arg His
1               5                  10                  15

Pro His Phe Pro Thr Arg Tyr Tyr Arg Ile Thr Tyr Gly Glu Thr Gly
            20                  25                  30
```

```
Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
     50                  55                  60

Tyr Ala Val Thr Ser Gly His Asn Asp His Met Leu Met Ile Pro Ile
 65                  70                  75                  80

Ser Ile Asn Tyr Arg Thr
                85

<210> SEQ ID NO 135
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
     50                  55                  60

Tyr Ala Val Thr Ala Gly Tyr Asn Asp Gln Ile Leu Met Thr Pro Ile
 65                  70                  75                  80

Ser Ile Asn Tyr Arg Thr
                85

<210> SEQ ID NO 136
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
     50                  55                  60

Tyr Ala Val Thr Phe Gly Leu Tyr Gly Lys Glu Leu Leu Ile Pro Ile
 65                  70                  75                  80

Ser Ile Asn Tyr Arg Thr
                85

<210> SEQ ID NO 137
<211> LENGTH: 86
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 137

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Thr Gly Pro Asn Asp Arg Leu Leu Phe Val Pro Ile
65                  70                  75                  80

Ser Ile Asn Tyr Arg Thr
                85

<210> SEQ ID NO 138
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Val Tyr Asn Asp His Glu Ile Lys Thr Pro Ile
65                  70                  75                  80

Ser Ile Asn Tyr Arg Thr
                85

<210> SEQ ID NO 139
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Lys Asp Gly Arg Val Leu Leu Thr Pro Ile
```

Ser Ile Asn Tyr Arg Thr
            85

<210> SEQ ID NO 140
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Glu Val His His Asp Arg Glu Ile Lys Thr Pro Ile
65                  70                  75                  80

Ser Ile Asn Tyr Arg Thr
            85

<210> SEQ ID NO 141
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Gln Ala Pro Asn Asp Arg Val Leu Tyr Thr Pro Ile
65                  70                  75                  80

Ser Ile Asn Tyr Arg Thr
            85

<210> SEQ ID NO 142
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Glu Val Val Ala Ala Thr Pro Thr Ser Leu Leu Ile Ser Trp Arg His
1               5                   10                  15

```
Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Arg Glu Glu Asn Asp His Glu Leu Leu Ile Pro Ile
65                  70                  75                  80

Ser Ile Asn Tyr Arg Thr
                85

<210> SEQ ID NO 143
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Thr His Asn Gly His Pro Leu Met Thr Pro Ile
65                  70                  75                  80

Ser Ile Asn Tyr Arg Thr
                85

<210> SEQ ID NO 144
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Ala Leu Lys Gly His Glu Leu Leu Thr Pro Ile
65                  70                  75                  80

Ser Ile Asn Tyr Arg Thr
                85

<210> SEQ ID NO 145
<211> LENGTH: 94
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Thr Ala Thr Ile Ser Gly Leu Lys Pro
    50                  55                  60

Gly Val Asp Tyr Thr Ile Thr Gly Tyr Ala Val Thr Val Ala Gln Asn
65                  70                  75                  80

Asp His Glu Leu Ile Thr Pro Ile Ser Ile Asn Tyr Arg Thr
                85                  90

<210> SEQ ID NO 146
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Val Ser Asp Val Pro Arg Asp Leu Gln Glu Val Val Ala Ala Thr Pro
1               5                   10                  15

Thr Ser Leu Leu Ile Ser Trp Arg His Pro His Phe Pro Thr Arg Tyr
            20                  25                  30

Tyr Arg Ile Thr Tyr Gly Glu Thr Gly Gly Asn Ser Pro Val Gln Glu
        35                  40                  45

Phe Thr Val Pro Leu Gln Pro Pro Ala Ala Thr Ile Ser Gly Leu Lys
    50                  55                  60

Pro Gly Val Asp Tyr Thr Ile Thr Gly Tyr Ala Val Thr Met Ala Gln
65                  70                  75                  80

Ser Gly His Glu Leu Phe Thr Pro Ile Ser Ile Asn Tyr Arg Thr
                85                  90                  95

<210> SEQ ID NO 147
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
```

```
                    50                  55                  60

Tyr Ala Val Thr Val Glu Arg Asn Gly Arg Val Leu Met Thr Pro Ile
 65                  70                  75                  80

Ser Ile Asn Tyr Arg Thr
                85

<210> SEQ ID NO 148
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
 50                  55                  60

Tyr Ala Val Thr Val Glu Arg Asn Gly Arg His Leu Met Thr Pro Ile
 65                  70                  75                  80

Ser Ile Asn Tyr Arg Thr
                85

<210> SEQ ID NO 149
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
 50                  55                  60

Tyr Ala Val Thr Leu Glu Arg Asn Gly Arg Glu Leu Met Thr Pro Ile
 65                  70                  75                  80

Ser Ile Asn Tyr Arg Thr
                85

<210> SEQ ID NO 150
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 150
```

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Glu Glu Arg Asn Gly Arg Thr Leu Arg Thr Pro Ile
65              70                  75                  80

Ser Ile Asn Tyr Arg Thr
                85
```

<210> SEQ ID NO 151
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 151

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Asp Arg Val Leu Phe Thr Pro Ile
65              70                  75                  80

Ser Ile Asn Tyr Arg Thr
                85
```

<210> SEQ ID NO 152
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 152

```
Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Val Glu Arg Asn Gly Arg Glu Leu Met Thr Pro Ile
65              70                  75                  80

Ser Ile Asn Tyr Arg Thr
                85
```

<210> SEQ ID NO 153
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 153

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Arg Asn Gly Arg Glu Leu Met Val Pro Ile
65                  70                  75                  80

Ser Ile Asn Tyr Arg Thr
                85

<210> SEQ ID NO 154
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 154

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Arg Asn Asp Arg Lys Leu Met Val Pro Ile
65                  70                  75                  80

Ser Ile Asn Tyr Arg Thr
                85

<210> SEQ ID NO 155
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 155

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr

-continued

```
                35                  40                  45

Ala Thr Ile Ser Gly Leu Lys Pro Gly Val Asp Tyr Thr Ile Thr Gly
         50                  55                  60

Tyr Ala Val Thr Asp Gly Gln Asn Gly Arg Leu Leu Asn Val Pro Ile
 65                  70                  75                  80

Ser Ile Asn Tyr Arg Thr
                 85

<210> SEQ ID NO 156
<211> LENGTH: 87
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Glu Val Val Ala Ala Thr Pro Thr Ser Leu Leu Ile Ser Trp Arg His
 1               5                  10                  15

His Pro His Phe Pro Thr Arg Tyr Tyr Arg Ile Thr Tyr Gly Glu Thr
                20                  25                  30

Gly Gly Asn Ser Pro Val Gln Glu Phe Thr Val Pro Leu Gln Pro Pro
             35                  40                  45

Thr Ala Thr Ile Ser Gly Leu Lys Pro Gly Val Asp Tyr Thr Ile Thr
         50                  55                  60

Gly Tyr Ala Val Thr Val His Trp Asn Gly Arg Glu Leu Met Thr Pro
 65                  70                  75                  80

Ile Ser Ile Asn Tyr Arg Thr
                 85

<210> SEQ ID NO 157
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Glu Val Val Ala Ala Thr Pro Thr Ser Leu Leu Ile Ser Trp Arg His
 1               5                  10                  15

Pro His Phe Pro Thr Arg Tyr Tyr Arg Ile Thr Tyr Gly Glu Thr Gly
                20                  25                  30

Gly Asn Ser Pro Val Gln Glu Phe Thr Val Pro Leu Gln Pro Pro Thr
             35                  40                  45

Ala Thr Ile Ser Gly Leu Lys Pro Gly Val Asp Tyr Thr Ile Thr Gly
         50                  55                  60

Tyr Ala Val Thr Glu Glu Trp Asn Gly Arg Val Leu Met Thr Pro Ile
 65                  70                  75                  80

Ser Ile Asn Tyr Arg Thr
                 85

<210> SEQ ID NO 158
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 158

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly His Thr Leu Met Thr Pro Ile
65                  70                  75                  80

Ser Ile Asn Tyr Arg Thr
                85

<210> SEQ ID NO 159
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Glu Asn Gly Arg Gln Leu Met Thr Pro Ile
65                  70                  75                  80

Ser Ile Asn Tyr Arg Thr
                85

<210> SEQ ID NO 160
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Arg Asn Gly Gln Val Leu Phe Thr Pro Ile
65                  70                  75                  80

```
Ser Ile Asn Tyr Arg Thr
            85

<210> SEQ ID NO 161
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 161

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Arg Asn Gly Gln Val Leu Tyr Thr Pro Ile
65                  70                  75                  80

Ser Ile Asn Tyr Arg Thr
            85

<210> SEQ ID NO 162
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Trp Gly Tyr Lys Asp His Glu Leu Leu Ile Pro Ile
65                  70                  75                  80

Ser Ile Asn Tyr Arg Thr
            85

<210> SEQ ID NO 163
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
```

```
                    20                  25                  30

Gly Asn Ser Pro Val Gln Glu Phe Thr Val Pro Leu Gln Pro Pro Thr
            35                  40                  45

Ala Thr Ile Ser Gly Leu Lys Pro Gly Val Asp Tyr Thr Ile Thr Gly
        50                  55                  60

Tyr Ala Val Thr Leu Gly Arg Asn Asp Arg Glu Leu Leu Thr Pro Ile
65                  70                  75                  80

Ser Ile Asn Tyr Arg Thr
                85

<210> SEQ ID NO 164
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Asp Gly Pro Asn Asp Arg Leu Leu Asn Ile Pro Ile
65                  70                  75                  80

Ser Ile Asn Tyr Arg Thr
                85

<210> SEQ ID NO 165
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Phe Ala Arg Asp Gly His Glu Ile Leu Thr Pro Ile
65                  70                  75                  80

Ser Ile Asn Tyr Arg Thr
                85

<210> SEQ ID NO 166
<211> LENGTH: 86
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 166

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Leu Glu Gln Asn Gly Arg Glu Leu Met Thr Pro Ile
65                  70                  75                  80

Ser Ile Asn Tyr Arg Thr
                85

<210> SEQ ID NO 167
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60

Tyr Ala Val Thr Val Glu Glu Asn Gly Arg Val Leu Asn Thr Pro Ile
65                  70                  75                  80

Ser Ile Asn Tyr Arg Thr
                85

<210> SEQ ID NO 168
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Gly
    50                  55                  60
```

```
Tyr Ala Val Thr Leu Glu Pro Asn Gly Arg Tyr Leu Met Val Pro Ile
 65                  70                  75                  80

Ser Ile Asn Tyr Arg Thr
                 85

<210> SEQ ID NO 169
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 169

Glu Val Val Ala Ala Thr Pro Thr Ser Leu Leu Ile Ser Trp Arg His
  1               5                  10                  15

Pro His Phe Pro Thr Arg Tyr Tyr Arg Ile Thr Tyr Gly Glu Thr Gly
             20                  25                  30

Gly Asn Ser Pro Val Gln Glu Phe Thr Val Pro Leu Gln Pro Pro Thr
         35                  40                  45

Ala Thr Ile Ser Gly Leu Lys Pro Gly Val Asp Tyr Thr Ile Thr Gly
     50                  55                  60

Tyr Ala Val Thr Glu Gly Arg Asn Gly Arg Glu Leu Phe Ile Pro Ile
 65                  70                  75                  80

Ser Ile Asn Tyr Arg Thr
                 85

<210> SEQ ID NO 170
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

Val Ser Asp Val Pro Arg Asp Leu Glu Val Val Ala Ala Thr Pro Thr
  1               5                  10                  15

Ser Leu Leu Ile Ser Trp Arg His Pro His Phe Pro Thr Arg Tyr Tyr
             20                  25                  30

Arg Ile Thr Tyr Gly Glu Thr Gly Gly Asn Ser Pro Val Gln Glu Phe
             35                  40                  45

Thr Val Pro Leu Gln Pro Pro Ala Ala Thr Ile Ser Gly Leu Lys Pro
         50                  55                  60

Gly Val Asp Tyr Thr Ile Thr Gly Tyr Ala Val Thr Trp Glu Arg Asn
 65                  70                  75                  80

Gly Arg Glu Leu Phe Thr Pro Ile Ser Ile Asn Tyr Arg Thr
                 85                  90

<210> SEQ ID NO 171
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Val Ser Asp Val Pro Arg Asp Leu Glu Val Val Ala Ala Thr Pro Thr
```

-continued

```
                1               5                   10                  15
Ser Leu Leu Ile Ser Trp Arg His Pro His Phe Pro Thr Arg Tyr Tyr
                20                  25                  30

Arg Ile Thr Tyr Gly Glu Thr Gly Asn Ser Pro Val Gln Glu Phe
                35                  40                  45

Thr Val Pro Leu Gln Pro Pro Ala Ala Thr Ile Ser Gly Leu Lys Pro
                50                  55                  60

Gly Val Asp Tyr Thr Ile Thr Gly Tyr Ala Val Thr Lys Glu Arg Asn
 65                 70                  75                  80

Gly Arg Glu Leu Phe Thr Pro Ile Ser Ile Asn Tyr Arg Thr
                85                  90

<210> SEQ ID NO 172
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr His Tyr Tyr
                20                  25                  30

Arg Ile Thr Tyr Gly Glu Thr Gly Gly Asn Ser Pro Val Gln Glu Phe
                35                  40                  45

Thr Val Pro Leu Gln Pro Pro Ala Ala Thr Ile Ser Gly Leu Lys Pro
                50                  55                  60

Gly Val Asp Tyr Thr Ile Thr Gly Tyr Ala Val Thr Thr Glu Arg Thr
 65                 70                  75                  80

Gly Arg Glu Leu Phe Thr Pro Ile Ser Ile Asn Tyr Arg Thr
                85                  90

<210> SEQ ID NO 173
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Val Ser Asp Val Pro Arg Asp Leu Glu Val Val Ala Ala Thr Pro Thr
 1               5                  10                  15

Ser Leu Leu Ile Ser Trp Arg His Pro His Phe Pro Thr His Tyr Tyr
                20                  25                  30

Arg Ile Thr Tyr Gly Glu Thr Gly Gly Asn Ser Pro Val Gln Glu Phe
                35                  40                  45

Thr Val Pro Leu Gln Pro Pro Ala Ala Thr Ile Ser Gly Leu Lys Pro
                50                  55                  60

Gly Val Asp Tyr Thr Ile Thr Gly Tyr Ala Val Thr Lys Glu Arg Ser
 65                 70                  75                  80

Gly Arg Glu Leu Phe Thr Pro Ile Ser Ile Asn Tyr Arg Thr
                85                  90

<210> SEQ ID NO 174
```

<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 174

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr His Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Ala Ala Thr Ile Ser Gly Leu Lys Pro
    50                  55                  60

Gly Val Asp Tyr Thr Ile Thr Gly Tyr Ala Val Thr Leu Glu Arg Asp
65                  70                  75                  80

Gly Arg Glu Leu Phe Thr Pro Ile Ser Ile Asn Tyr Arg Thr
                85                  90

<210> SEQ ID NO 175
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (72)..(72)
<223> OTHER INFORMATION: /replace="Val"
<220> FEATURE:
<221> NAME/KEY: misc_feature
<222> LOCATION: (72)..(72)
<223> OTHER INFORMATION: /note="Residue given in the sequence has no preference with respect to that in the annotation for said position"

<400> SEQUENCE: 175

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
            20                  25                  30

Arg Ile Thr Tyr Gly Glu Thr Gly Gly Asn Ser Pro Val Gln Glu Phe
        35                  40                  45

Thr Val Pro Leu Gln Pro Pro Leu Ala Thr Ile Ser Gly Leu Lys Pro
    50                  55                  60

Gly Val Asp Tyr Thr Ile Thr Gly Tyr Ala Val Thr Lys Glu Arg Asn
65                  70                  75                  80

Gly Arg Glu Leu Phe Thr Pro Ile Ser Ile Asn Tyr Arg Thr
                85                  90

<210> SEQ ID NO 176
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 176

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Thr Thr Ala Thr Ile Ser Gly Leu Lys Pro
        50                  55                  60

Gly Val Asp Tyr Thr Ile Thr Gly Tyr Ala Val Thr Trp Glu Arg Asn
65                  70                  75                  80

Gly Arg Glu Leu Phe Thr Pro Ile Ser Ile Asn Tyr Arg Thr
                85                  90

<210> SEQ ID NO 177
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177

Val Ser Asp Val Pro Arg Asp Leu Glu Val Val Ala Ala Thr Pro Thr
1               5                   10                  15

Ser Leu Leu Ile Ser Trp Arg His Pro His Phe Pro Thr Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Gln Pro Thr Val Ala Thr Ile Ser Gly Leu Lys Pro
        50                  55                  60

Gly Val Asp Tyr Thr Ile Thr Gly Tyr Ala Val Thr Leu Glu Arg Asn
65                  70                  75                  80

Asp Arg Glu Leu Phe Thr Pro Ile Ser Ile Asn Tyr Arg Thr
                85                  90

<210> SEQ ID NO 178
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Met Gly Glu Val Val Ala Ala Thr Pro Thr Ser Leu Leu Ile Ser Trp
1               5                   10                  15

Arg His Pro His Phe Pro Thr Arg Tyr Tyr Arg Ile Thr Tyr Gly Glu
                20                  25                  30

Thr Gly Gly Asn Ser Pro Val Gln Glu Phe Thr Val Pro Leu Gln Pro
            35                  40                  45

Pro Thr Ala Thr Ile Ser Gly Leu Lys Pro Gly Val Asp Tyr Thr Ile
        50                  55                  60

Thr Val Tyr Ala Val Thr Asp Gly Arg Asn Gly Arg Leu Leu Ser Ile
65                  70                  75                  80

Pro Ile Ser Ile Asn Tyr Arg Thr Glu Ile Asp Lys Pro Ser Gln
                85                  90                  95

<210> SEQ ID NO 179
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 179

Met Gly Glu Val Val Ala Ala Thr Pro Thr Ser Leu Leu Ile Ser Trp
1               5                   10                  15

Arg His Pro His Phe Pro Thr Arg Tyr Tyr Arg Ile Thr Tyr Gly Glu
            20                  25                  30

Thr Gly Gly Asn Ser Pro Val Gln Glu Phe Thr Val Pro Leu Gln Pro
        35                  40                  45

Pro Thr Ala Thr Ile Ser Gly Leu Lys Pro Gly Val Asp Tyr Thr Ile
    50                  55                  60

Thr Val Tyr Ala Val Thr Asp Gly Arg Asn Gly Arg Leu Leu Ser Ile
65                  70                  75                  80

Pro Ile Ser Ile Asn Tyr Arg Thr Glu Ile Asp Lys Pro Cys Gln
                85                  90                  95

<210> SEQ ID NO 180
<211> LENGTH: 102
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 180

Met Val Ser Asp Val Pro Arg Asp Leu Glu Val Val Ala Ala Thr Pro
1               5                   10                  15

Thr Ser Leu Leu Ile Ser Trp Arg His Pro His Phe Pro Thr Arg Tyr
            20                  25                  30

Tyr Arg Ile Thr Tyr Gly Glu Thr Gly Gly Asn Ser Pro Val Gln Glu
        35                  40                  45

Phe Thr Val Pro Leu Gln Pro Pro Thr Ala Thr Ile Ser Gly Leu Lys
    50                  55                  60

Pro Gly Val Asp Tyr Thr Ile Thr Val Tyr Ala Val Thr Asp Gly Arg
65                  70                  75                  80

Asn Gly Arg Leu Leu Ser Ile Pro Ile Ser Ile Asn Tyr Arg Thr Glu
                85                  90                  95

Ile Asp Lys Pro Ser Gln
            100

<210> SEQ ID NO 181
<211> LENGTH: 88
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 181

Met Gly Glu Val Val Ala Ala Thr Pro Thr Ser Leu Leu Ile Ser Trp
1               5                   10                  15

Arg His Pro His Phe Pro Thr Arg Tyr Tyr Arg Ile Thr Tyr Gly Glu

```
                    20                  25                  30

Thr Gly Gly Asn Ser Pro Val Gln Glu Phe Thr Val Pro Leu Gln Pro
            35                  40                  45

Pro Thr Ala Thr Ile Ser Gly Leu Lys Pro Gly Val Asp Tyr Thr Ile
    50                  55                  60

Thr Val Tyr Ala Val Thr Asp Gly Trp Asn Gly Arg Leu Leu Ser Ile
65                  70                  75                  80

Pro Ile Ser Ile Asn Tyr Arg Thr
                85

<210> SEQ ID NO 182
<211> LENGTH: 88
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Met Gly Glu Val Val Ala Ala Thr Pro Thr Ser Leu Leu Ile Ser Trp
1               5                   10                  15

Arg His Pro His Phe Pro Thr Arg Tyr Tyr Arg Ile Thr Tyr Gly Glu
            20                  25                  30

Thr Gly Gly Asn Ser Pro Val Gln Glu Phe Thr Val Pro Leu Gln Pro
        35                      40                  45

Pro Thr Ala Thr Ile Ser Gly Leu Lys Pro Gly Val Asp Tyr Thr Ile
    50                  55                  60

Thr Val Tyr Ala Val Thr Glu Gly Pro Asn Glu Arg Ser Leu Phe Ile
65                  70                  75                  80

Pro Ile Ser Ile Asn Tyr Arg Thr
                85

<210> SEQ ID NO 183
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

Met Val Ser Asp Val Pro Arg Asp Leu Glu Val Val Ala Ala Thr Pro
1               5                   10                  15

Thr Ser Leu Leu Ile Ser Trp Arg His Pro His Phe Pro Thr Arg Tyr
            20                  25                  30

Tyr Arg Ile Thr Tyr Gly Glu Thr Gly Gly Asn Ser Pro Val Gln Glu
            35                  40                  45

Phe Thr Val Pro Leu Gln Pro Pro Thr Ala Thr Ile Ser Gly Leu Lys
    50                  55                  60

Pro Gly Val Asp Tyr Thr Ile Thr Val Tyr Ala Val Thr Glu Gly Pro
65                  70                  75                  80

Asn Glu Arg Ser Leu Phe Ile Pro Ile Ser Ile Asn Tyr Arg Thr
                85                  90                  95

<210> SEQ ID NO 184
<211> LENGTH: 90
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 184

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Arg Phe Arg Asp
65                  70                  75                  80

Tyr Gln Pro Ile Ser Ile Asn Tyr Arg Thr
                85                  90

<210> SEQ ID NO 185
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Arg Ile Arg Asp
65                  70                  75                  80

Tyr Gly Pro Ile Ser Ile Asn Tyr Arg Thr
                85                  90

<210> SEQ ID NO 186
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60
```

```
Gly Val Asp Tyr Thr Ile Thr Val Tyr Ala Val Thr Ala Tyr Arg Asp
 65                  70                  75                  80

Tyr Gln Pro Ile Ser Ile Asn Tyr Arg Thr
                 85                  90

<210> SEQ ID NO 187
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 187

Val Ser Asp Val Pro Arg Asp Leu Glu Val Val Ala Ala Thr Pro Thr
 1               5                  10                  15

Ser Leu Leu Ile Ser Trp Ser Ala Arg Leu Lys Val Ala Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Lys Asn Val Tyr Thr Ala Thr Ile Ser Gly Leu Lys Pro
         50                  55                  60

Gly Val Asp Tyr Thr Ile Thr Val Tyr Ala Val Thr Arg Glu Arg Asp
 65                  70                  75                  80

Tyr Arg Pro Ile Ser Ile Asn Tyr Arg Thr
                 85                  90

<210> SEQ ID NO 188
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 188

Val Ser Asp Val Pro Arg Asp Leu Glu Val Val Ala Ala Thr Pro Thr
 1               5                  10                  15

Ser Leu Leu Ile Ser Trp Ser Ala Arg Leu Lys Val Ala Arg Tyr Tyr
                 20                  25                  30

Arg Ile Thr Tyr Gly Glu Thr Gly Gly Asn Ser Pro Val Gln Glu Phe
                 35                  40                  45

Thr Val Pro Lys Asn Val Tyr Thr Ala Thr Ile Ser Gly Leu Lys Pro
         50                  55                  60

Gly Val Asp Tyr Thr Ile Thr Val Tyr Ala Val Thr Ala Val Arg Asp
 65                  70                  75                  80

Tyr Arg Pro Ile Ser Ile Asn Tyr Arg Thr
                 85                  90

<210> SEQ ID NO 189
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189

Val Ser Asp Val Pro Arg Asp Leu Glu Val Val Ala Ala Thr Pro Thr
```

```
                1               5                  10                  15
        Ser Leu Leu Ile Ser Trp Ser Ala Arg Leu Lys Val Ala Arg Tyr Tyr
                        20                  25                  30

Arg Ile Thr Tyr Gly Glu Thr Gly Gly Asn Ser Pro Val Gln Glu Phe
                        35                  40                  45

Thr Val Pro Lys Asn Val Tyr Thr Ala Thr Ile Ser Gly Leu Lys Pro
                        50                  55                  60

Gly Val Asp Tyr Thr Ile Thr Val Tyr Ala Val Thr Glu Leu Arg Asn
         65                 70                  75                  80

Tyr Gly Pro Ile Ser Ile Asn Tyr Arg Thr
                        85                  90

<210> SEQ ID NO 190
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190

Val Ser Asp Val Pro Arg Asp Leu Glu Val Val Ala Ala Thr Pro Thr
         1               5                  10                  15

Ser Leu Leu Ile Ser Trp Ser Ala Arg Leu Lys Val Ala Arg Tyr Tyr
                        20                  25                  30

Arg Ile Thr Tyr Gly Glu Thr Gly Gly Asn Ser Pro Val Gln Glu Phe
                        35                  40                  45

Thr Val Pro Lys Asn Val Tyr Thr Ala Thr Ile Ser Gly Leu Lys Pro
                        50                  55                  60

Gly Val Asp Tyr Thr Ile Thr Val Tyr Ala Val Thr Ser Leu Arg Asp
         65                 70                  75                  80

Tyr Ala Pro Ile Ser Ile Asn Tyr Arg Thr
                        85                  90

<210> SEQ ID NO 191
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 191

Val Ser Asp Val Pro Arg Asp Leu Glu Val Val Ala Ala Thr Pro Thr
         1               5                  10                  15

Ser Leu Leu Ile Ser Trp Ser Ala Arg Leu Lys Val Ala Arg Tyr Tyr
                        20                  25                  30

Arg Ile Thr Tyr Gly Glu Thr Gly Gly Asn Ser Pro Val Gln Glu Phe
                        35                  40                  45

Thr Val Pro Lys Asn Val Tyr Thr Ala Thr Ile Ser Gly Leu Lys Pro
                        50                  55                  60

Gly Val Asp Tyr Thr Ile Thr Val Tyr Ala Val Thr Gln Leu Arg Asp
         65                 70                  75                  80

Tyr Ser Pro Ile Ser Ile Asn Tyr Arg Thr
                        85                  90

<210> SEQ ID NO 192
```

<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 192

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Asn Leu Arg Asp
65                  70                  75                  80

Tyr Gly Pro Ile Ser Ile Asn Tyr Arg Thr
                85                  90

<210> SEQ ID NO 193
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 193

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Glu Arg Arg Asp
65                  70                  75                  80

Tyr Arg Pro Ile Ser Ile Asn Tyr Arg Thr
                85                  90

<210> SEQ ID NO 194
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 194

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

```
Thr Val Pro Lys Asn Val Tyr Thr Ala Thr Ile Ser Gly Leu Lys Pro
        50                  55                  60

Gly Val Asp Tyr Thr Ile Thr Val Tyr Ala Val Thr Leu Val Arg Asn
 65                  70                  75                  80

Tyr Gly Pro Ile Ser Ile Asn Tyr Arg Thr
                 85                  90

<210> SEQ ID NO 195
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Val Ser Asp Val Pro Arg Asp Leu Glu Val Val Ala Ala Thr Pro Thr
 1               5                  10                  15

Ser Leu Leu Ile Ser Trp Ser Ala Arg Leu Lys Val Ala Arg Tyr Tyr
                 20                  25                  30

Arg Ile Thr Tyr Gly Glu Thr Gly Gly Asn Ser Pro Val Gln Glu Phe
             35                  40                  45

Thr Val Pro Lys Asn Val Tyr Thr Ala Thr Ile Ser Gly Leu Lys Pro
        50                  55                  60

Gly Val Asp Tyr Thr Ile Thr Val Tyr Ala Val Thr Thr Ile Arg Asp
 65                  70                  75                  80

Tyr Arg Pro Ile Ser Ile Asn Tyr Arg Thr
                 85                  90

<210> SEQ ID NO 196
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Val Ser Asp Val Pro Arg Asp Leu Glu Val Val Ala Ala Thr Pro Thr
 1               5                  10                  15

Ser Leu Leu Ile Ser Trp Ser Ala Arg Leu Lys Val Ala Arg Tyr Tyr
                 20                  25                  30

Arg Ile Thr Tyr Gly Glu Thr Gly Gly Asn Ser Pro Val Gln Glu Phe
             35                  40                  45

Thr Val Pro Lys Asn Val Tyr Thr Ala Thr Ile Ser Gly Leu Lys Pro
        50                  55                  60

Gly Val Asp Tyr Thr Ile Thr Val Tyr Ala Val Thr Leu Leu Arg Asp
 65                  70                  75                  80

Tyr Gly Pro Ile Ser Ile Asn Tyr Arg Thr
                 85                  90

<210> SEQ ID NO 197
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 197

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Leu Thr Arg Asp
65                  70                  75                  80

Tyr Lys Pro Ile Ser Ile Asn Tyr Arg Thr
                85                  90

<210> SEQ ID NO 198
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 198

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Val Val Arg Asp
65                  70                  75                  80

Tyr Arg Pro Ile Ser Ile Asn Tyr Arg Thr
                85                  90

<210> SEQ ID NO 199
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Ser Tyr Arg Asp
65                  70                  75                  80

Tyr Trp Pro Ile Ser Ile Asn Tyr Arg Thr
                85                  90

<210> SEQ ID NO 200
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Met Ser Arg Asp
65                  70                  75                  80

Tyr Gly Pro Ile Ser Ile Asn Tyr Arg Thr
            85                  90

<210> SEQ ID NO 201
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
        35                  40                  45

Thr Val Pro Lys Asn Val Tyr Thr Ala Thr Ile Ser Gly Leu Lys Pro
    50                  55                  60

Gly Val Asp Tyr Thr Ile Thr Val Tyr Ala Val Thr Ser Leu Arg Asp
65                  70                  75                  80

Tyr Gly Pro Ile Ser Ile Asn Tyr Arg Thr
            85                  90

<210> SEQ ID NO 202
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Val Ser Asp Val Pro Arg Asp Leu Glu Val Val Ala Ala Thr Pro Thr
1               5                   10                  15

Ser Leu Leu Ile Ser Trp Ser Ala Arg Leu Lys Val Ala Arg Tyr Tyr
            20                  25                  30

Arg Ile Thr Tyr Gly Glu Thr Gly Gly Asn Ser Pro Val Gln Glu Phe
            35                  40                  45

Thr Val Pro Lys Asn Val Tyr Thr Ala Thr Ile Ser Gly Leu Lys Pro
 50                  55                  60

Gly Val Asp Tyr Thr Ile Thr Val Tyr Ala Val Thr Gly Val Arg Asn
65                  70                  75                  80

Tyr Gly Pro Ile Ser Ile Asn Tyr Arg Thr
                85                  90

<210> SEQ ID NO 203
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Gly Val Ser Asp Val Pro Arg Asp Leu Glu Val Val Ala Ala Thr Pro
1               5                   10                  15

Thr Ser Leu Leu Ile Ser Trp Ser Ala Arg Leu Lys Val Ala Arg Tyr
            20                  25                  30

Tyr Arg Ile Thr Tyr Gly Glu Thr Gly Gly Asn Ser Pro Val Gln Glu
        35                  40                  45

Phe Thr Val Pro Lys Asn Val Tyr Thr Ala Thr Ile Ser Gly Leu Lys
    50                  55                  60

Pro Gly Val Asp Tyr Thr Ile Thr Val Tyr Ala Val Thr Arg Phe Arg
65                  70                  75                  80

Asp Tyr Gln Pro Ile Ser Ile Asn Tyr Arg Thr Glu Ile Asp Lys Pro
                85                  90                  95

Cys Gln

<210> SEQ ID NO 204
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

Gly Val Ser Asp Val Pro Arg Asp Leu Glu Val Val Ala Ala Thr Pro
1               5                   10                  15

Thr Ser Leu Leu Ile Ser Trp Ser Ala Arg Leu Lys Val Ala Arg Tyr
            20                  25                  30

Tyr Arg Ile Thr Tyr Gly Glu Thr Gly Gly Asn Ser Pro Val Gln Glu
        35                  40                  45

Phe Thr Val Pro Lys Asn Val Tyr Thr Ala Thr Ile Ser Gly Leu Lys
    50                  55                  60

Pro Gly Val Asp Tyr Thr Ile Thr Val Tyr Ala Val Thr Arg Phe Arg
65                  70                  75                  80

Asp Tyr Gln Pro Ile Ser Ile Asn Tyr Arg Thr Glu Ile Asp Lys Pro
                85                  90                  95

Ser Gln

<210> SEQ ID NO 205
<211> LENGTH: 93

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 205

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Val
    50                  55                  60

Tyr Ala Val Thr Asp Gly Arg Asn Gly Arg Leu Leu Ser Ile Pro Ile
65                  70                  75                  80

Ser Ile Asn Tyr Arg Thr Glu Ile Asp Lys Pro Ser Gln
                85                  90

<210> SEQ ID NO 206
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Val
    50                  55                  60

Tyr Ala Val Thr Asp Gly Arg Asn Gly Arg Leu Leu Ser Ile Pro Ile
65                  70                  75                  80

Ser Ile Asn Tyr Arg Thr Glu Ile Asp Lys Pro Cys Gln
                85                  90

<210> SEQ ID NO 207
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Val Ser Asp Val Pro Arg Asp Leu Glu Val Val Ala Ala Thr Pro Thr
1               5                   10                  15

Ser Leu Leu Ile Ser Trp Ala Arg Tyr Ala Gly Ser Asp Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp Val Pro Phe Thr Ala Thr Ile Ser Gly Leu Lys Pro

```
                50             55                60
Gly Val Asp Tyr Thr Ile Thr Val Tyr Ala Val Thr Met Gly His Ala
 65                 70                  75                  80

Pro Thr Val Asp Ile His Trp Thr Pro Ser Pro Ile Ser Ile Asn Tyr
                    85                  90                  95

Arg Thr

<210> SEQ ID NO 208
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

Val Ser Asp Val Pro Arg Asp Leu Glu Val Val Ala Ala Thr Pro Thr
 1               5                  10                  15

Ser Leu Leu Ile Ser Trp Ala Arg Tyr Ala Glu Cys Gly Arg Tyr Tyr
                20                  25                  30

Arg Ile Thr Tyr Gly Glu Thr Gly Gly Asn Ser Pro Val Gln Glu Phe
            35                  40                  45

Thr Val Pro Asp Val Pro Trp Thr Ala Thr Ile Ser Gly Leu Lys Pro
        50                  55                  60

Gly Val Asp Tyr Thr Ile Thr Val Tyr Ala Val Thr Leu Gly Lys Pro
 65                 70                  75                  80

Pro Leu Pro Gly Trp Val Ser Gly Leu Asp Pro Ile Ser Ile Asn Tyr
                    85                  90                  95

Arg Thr

<210> SEQ ID NO 209
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Val Ser Asp Val Pro Arg Asp Leu Glu Val Val Ala Ala Thr Pro Thr
 1               5                  10                  15

Ser Leu Leu Ile Ser Trp Asp Arg Met Leu Ser Phe Leu Arg Tyr Tyr
                20                  25                  30

Arg Ile Thr Tyr Gly Glu Thr Gly Gly Asn Ser Pro Val Gln Glu Phe
            35                  40                  45

Thr Val Pro Leu Ile Tyr Pro Thr Ala Thr Ile Ser Gly Leu Lys Pro
        50                  55                  60

Gly Val Asp Tyr Thr Ile Thr Val Tyr Ala Val Thr Val Gln Leu Leu
 65                 70                  75                  80

Asp Gln Cys Leu Arg Ile His Gly Pro Ile Ser Ile Asn Tyr Arg Thr
                    85                  90                  95

<210> SEQ ID NO 210
<211> LENGTH: 96
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 210

Val Ser Asp Val Pro Arg Asp Leu Glu Val Val Ala Ala Thr Pro Thr
1               5                   10                  15

Ser Leu Leu Ile Ser Trp Leu Leu Leu Gly Ala Pro Cys Arg Tyr Tyr
            20                  25                  30

Arg Ile Thr Tyr Gly Glu Thr Gly Gly Asn Ser Pro Val Gln Glu Phe
        35                  40                  45

Thr Val Pro Trp Met Gly Leu Thr Ala Thr Ile Ser Gly Leu Lys Pro
    50                  55                  60

Gly Val Asp Tyr Thr Ile Thr Val Tyr Ala Val Thr Ser Glu Arg Ala
65                  70                  75                  80

Pro Cys Val Lys Val Trp Arg Cys Pro Ile Ser Ile Asn Tyr Arg Thr
                85                  90                  95

<210> SEQ ID NO 211
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 211

Val Ser Asp Val Pro Arg Asp Leu Glu Val Val Ala Ala Thr Pro Thr
1               5                   10                  15

Ser Leu Leu Ile Ser Trp Met Arg Trp Tyr Ala Pro Arg Arg Tyr Tyr
            20                  25                  30

Arg Ile Thr Tyr Gly Glu Thr Gly Gly Asn Ser Pro Val Gln Glu Phe
        35                  40                  45

Thr Val Pro Phe Trp Gln Gly Thr Ala Thr Ile Ser Gly Leu Lys Pro
    50                  55                  60

Gly Val Asp Tyr Thr Ile Thr Val Tyr Ala Val Thr Arg Gly Gln Ser
65                  70                  75                  80

Gly Leu Gly Met Pro Ile Ser Ile Asn Tyr Arg Thr
                85                  90

<210> SEQ ID NO 212
<211> LENGTH: 96
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Val Ser Asp Val Pro Arg Asp Leu Glu Val Val Ala Ala Thr Pro Thr
1               5                   10                  15

Ser Leu Leu Ile Ser Trp Arg Leu Thr Ala Pro Leu Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp Ile Pro Phe Thr Ala Thr Ile Ser Gly Leu Lys Pro
    50                  55                  60

Gly Val Asp Tyr Thr Ile Thr Val Tyr Ala Val Thr Leu Ser Asp Ser
65                  70                  75                  80

```
Ala His Gly Gly Leu Arg Asp Val Pro Ile Ser Ile Asn Tyr Arg Thr
            85                  90                  95

<210> SEQ ID NO 213
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 213

Val Ser Asp Val Pro Arg Asp Leu Glu Val Val Ala Ala Thr Pro Thr
1               5                   10                  15

Ser Leu Leu Ile Ser Trp Ser Arg Tyr Ala Pro Gly Gly Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp Val Pro Trp Thr Ala Thr Ile Ser Gly Leu Lys Pro
    50                  55                  60

Gly Val Asp Tyr Thr Ile Thr Val Tyr Ala Val Thr Leu Ser Asn Tyr
65                  70                  75                  80

Glu Tyr Leu Ala Arg Asn Pro Ile Ser Ile Asn Tyr Arg Thr
                85                  90

<210> SEQ ID NO 214
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 214

Val Ser Asp Val Pro Arg Asp Leu Glu Val Val Ala Ala Thr Pro Thr
1               5                   10                  15

Ser Leu Leu Ile Ser Trp Tyr His Tyr Tyr Ser Gly Ser Gln Arg Tyr
            20                  25                  30

Tyr Arg Ile Thr Tyr Gly Glu Thr Gly Gly Asn Ser Pro Val Gln Glu
        35                  40                  45

Phe Thr Val Pro His Glu Val Tyr Thr Ala Thr Ile Ser Gly Leu Lys
    50                  55                  60

Pro Gly Val Asp Tyr Thr Ile Thr Val Tyr Ala Val Thr Asp Tyr Ala
65                  70                  75                  80

Tyr Lys Glu Tyr Glu Tyr Pro Ile Ser Ile Asn Tyr Arg Thr
                85                  90                  95

<210> SEQ ID NO 215
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 215

Val Ser Asp Val Pro Arg Asp Leu Glu Val Val Ala Ala Thr Pro Thr
1               5                   10                  15
```

Ser Leu Leu Ile Ser Trp Gln Val Pro Arg Pro Met Tyr Gln Arg Tyr
            20                  25                  30

Tyr Arg Ile Thr Tyr Gly Glu Thr Gly Gly Asn Ser Pro Val Gln Glu
        35                  40                  45

Phe Thr Val Pro Gly Gly Val Arg Thr Ala Thr Ile Ser Gly Leu Lys
50                  55                  60

Pro Gly Val Asp Tyr Thr Ile Thr Val Tyr Ala Val Thr Asp Tyr Met
65                  70                  75                  80

His Ser Glu Tyr Arg Gln Tyr Pro Ile Ser Ile Asn Tyr Arg Thr
                85                  90                  95

<210> SEQ ID NO 216
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 216

Val Ser Asp Val Pro Arg Asp Leu Glu Val Val Ala Ala Thr Pro Thr
1               5                   10                  15

Ser Leu Leu Ile Ser Trp Tyr Ser Asp Tyr Tyr Asp Asn Arg Tyr Tyr
            20                  25                  30

Arg Ile Thr Tyr Gly Glu Thr Gly Gly Asn Ser Pro Val Gln Glu Phe
        35                  40                  45

Thr Val Pro Arg Tyr Met Met Thr Ala Thr Ile Ser Gly Leu Lys Pro
50                  55                  60

Gly Val Asp Tyr Thr Ile Thr Val Tyr Ala Val Thr Tyr Ser Tyr His
65                  70                  75                  80

Asp Pro Asn Pro Met Met Pro Ile Ser Ile Asn Tyr Arg Thr
                85                  90

<210> SEQ ID NO 217
<211> LENGTH: 92
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 217

Val Ser Asp Val Pro Arg Asp Leu Glu Val Val Ala Ala Thr Pro Thr
1               5                   10                  15

Ser Leu Leu Ile Ser Trp Gln Gln Gln His Thr Asn Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Arg Ala Ser Thr Ala Thr Ile Ser Gly Leu Lys Pro
50                  55                  60

Gly Val Asp Tyr Thr Ile Thr Val Tyr Ala Val Thr Glu His Pro Tyr
65                  70                  75                  80

Tyr Gly Asp Pro Pro Ile Ser Ile Asn Tyr Arg Thr
                85                  90

<210> SEQ ID NO 218
<211> LENGTH: 96
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 218

```
Val Ser Asp Val Pro Arg Asp Leu Glu Val Val Ala Ala Thr Pro Thr
1               5                   10                  15
Ser Leu Leu Ile Ser Trp Ile Arg Arg Ala Lys Pro Gly Arg Tyr Tyr
                20                  25                  30
Arg Ile Thr Tyr Gly Glu Thr Gly Gly Asn Ser Pro Val Gln Glu Phe
                35                  40                  45
Thr Val Pro Asp Val Pro Trp Thr Ala Thr Ile Ser Gly Leu Lys Pro
            50                  55                  60
Gly Val Asp Tyr Thr Ile Thr Val Tyr Ala Val Thr Leu Asp Gly Val
65                  70                  75                  80
Arg Arg Val Gly Tyr Leu Asp His Pro Ile Ser Ile Asn Tyr Arg Thr
                85                  90                  95
```

<210> SEQ ID NO 219
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 219

```
Val Ser Asp Val Pro Arg Asp Leu Glu Val Val Ala Ala Thr Pro Thr
1               5                   10                  15
Ser Leu Leu Ile Ser Trp Thr Tyr Arg His Tyr Pro Glu Arg Tyr Tyr
                20                  25                  30
Arg Ile Thr Tyr Gly Glu Thr Gly Gly Asn Ser Pro Val Gln Glu Phe
                35                  40                  45
Thr Val Pro Asp Pro Asp Ser Thr Ala Thr Ile Ser Gly Leu Lys Pro
            50                  55                  60
Gly Val Asp Tyr Thr Ile Thr Val Tyr Ala Val Thr Tyr Asn His Ser
65                  70                  75                  80
Ser Thr Pro Ile Ser Ile Asn Tyr Arg Thr
                85                  90
```

<210> SEQ ID NO 220
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 220

```
Val Ser Asp Val Pro Arg Asp Leu Glu Val Val Ala Ala Thr Pro Thr
1               5                   10                  15
Ser Leu Leu Ile Ser Trp Tyr Ser Arg Tyr Gln Ser Tyr Arg Tyr Tyr
                20                  25                  30
Arg Ile Thr Tyr Gly Glu Thr Gly Gly Asn Ser Pro Val Gln Glu Phe
                35                  40                  45
Thr Val Pro His Ala Ser Asn Thr Ala Thr Ile Ser Gly Leu Lys Pro
            50                  55                  60
```

```
Gly Val Asp Tyr Thr Ile Thr Val Tyr Ala Val Thr Val Asp Tyr Thr
 65                  70                  75                  80

Ala Val Gln Val Ser Tyr Pro Ile Ser Ile Asn Tyr Arg Thr
                 85                  90
```

<210> SEQ ID NO 221
<211> LENGTH: 93
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 221

```
Val Ser Asp Val Pro Arg Asp Leu Glu Val Val Ala Ala Thr Pro Thr
 1               5                  10                  15

Ser Leu Leu Ile Ser Trp Glu Ser Lys Tyr Val Asn Tyr Arg Tyr Tyr
                20                  25                  30

Arg Ile Thr Tyr Gly Glu Thr Gly Gly Asn Ser Pro Val Gln Glu Phe
                35                  40                  45

Thr Val Pro His Leu Met Thr Ala Thr Ile Ser Gly Leu Lys Pro Gly
             50                  55                  60

Val Asp Tyr Thr Ile Thr Val Tyr Ala Val Thr Val Gly Gly Asp His
 65                  70                  75                  80

Met Tyr Ser Ser Leu Pro Ile Ser Ile Asn Tyr Arg Thr
                 85                  90
```

<210> SEQ ID NO 222
<211> LENGTH: 90
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 222

```
Val Ser Asp Val Pro Arg Asp Leu Glu Val Val Ala Ala Thr Pro Thr
 1               5                  10                  15

Ser Leu Leu Ile Ser Trp Tyr Tyr Arg Lys Tyr Pro Gly Arg Tyr Tyr
                20                  25                  30

Arg Ile Thr Tyr Gly Glu Thr Gly Gly Asn Ser Pro Val Gln Glu Phe
                35                  40                  45

Thr Val Pro Asp Glu His Thr Thr Ala Thr Ile Ser Gly Leu Lys Pro
             50                  55                  60

Gly Val Asp Tyr Thr Ile Thr Val Tyr Ala Val Thr Tyr Asp Ser Pro
 65                  70                  75                  80

Ser Gln Pro Ile Ser Ile Asn Tyr Arg Thr
                 85                  90
```

<210> SEQ ID NO 223
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 223

```
Val Ser Asp Val Pro Arg Asp Leu Glu Val Val Ala Ala Thr Pro Thr
1               5                   10                  15

Ser Leu Leu Ile Ser Trp Tyr Ser Arg Tyr Gln Ser Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro His Ala Ser Asn Thr Ala Thr Ile Ser Gly Leu Lys Pro
    50                  55                  60

Gly Val Asp Tyr Thr Ile Thr Val Tyr Ala Val Thr Val Asp Tyr Thr
65                  70                  75                  80

Ala Val Gln Val Ser Tyr Pro Ile Ser Ile Asn Tyr Arg Thr
                85                  90
```

<210> SEQ ID NO 224
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 224

```
Val Ser Asp Val Pro Arg Asp Leu Glu Val Val Ala Ala Thr Pro Thr
1               5                   10                  15

Ser Leu Leu Ile Ser Trp Asn Arg His Ala Met Ala Ser Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp Val Pro Phe Thr Ala Thr Ile Ser Gly Leu Lys Pro
    50                  55                  60

Gly Val Asp Tyr Thr Ile Thr Val Tyr Ala Val Thr Met Ser Asp Lys
65                  70                  75                  80

Ala Met Asp Met Arg Thr Pro Ser Ile Gly Pro Ile Ser Ile Asn Tyr
                85                  90                  95

Arg Thr
```

<210> SEQ ID NO 225
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 225

```
Val Ser Asp Val Pro Arg Asp Leu Glu Val Val Ala Ala Thr Pro Thr
1               5                   10                  15

Ser Leu Leu Ile Ser Trp His Ser Asn Tyr Val Asp Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro His Ile Ser Asp Ile Thr Ala Thr Ile Ser Gly Leu Lys
    50                  55                  60

Pro Gly Val Asp Tyr Thr Ile Thr Val Tyr Ala Val Thr Val Glu Asp
65                  70                  75                  80

Met Val Arg Glu Ser Tyr Pro Pro Ile Ser Ile Asn Tyr Arg Thr
                85                  90                  95
```

<210> SEQ ID NO 226
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 226

Val Ser Asp Val Pro Arg Asp Leu Glu Val Val Ala Ala Thr Pro Thr
1               5                   10                  15

Ser Leu Leu Ile Ser Trp Ser Gly Ser Tyr Lys Ser Tyr Arg Tyr Tyr
            20                  25                  30

Arg Ile Thr Tyr Gly Glu Thr Gly Gly Asn Ser Pro Val Gln Glu Phe
        35                  40                  45

Thr Val Pro His Tyr Asp His Ala Thr Ala Thr Ile Ser Gly Leu Lys
    50                  55                  60

Pro Gly Val Asp Tyr Thr Ile Thr Val Tyr Ala Val Thr Val Asp Tyr
65                  70                  75                  80

Thr Ala Val Gln Val Ser Tyr Pro Ile Ser Ile Asn Tyr Arg Thr
                85                  90                  95

<210> SEQ ID NO 227
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 227

Val Ser Asp Val Pro Arg Asp Leu Glu Val Val Ala Ala Thr Pro Thr
1               5                   10                  15

Ser Leu Leu Ile Ser Trp Leu Arg Val Pro Ala Tyr Asp Arg Tyr Tyr
            20                  25                  30

Arg Ile Thr Tyr Gly Glu Thr Gly Gly Asn Ser Pro Val Gln Glu Phe
        35                  40                  45

Thr Val Pro Asp Val Pro Trp Thr Ala Thr Ile Ser Gly Leu Lys Pro
    50                  55                  60

Gly Val Asp Tyr Thr Ile Thr Val Tyr Ala Val Thr Leu Asp Glu Ser
65                  70                  75                  80

Asp Met Arg Val Gly Val Pro Ile Ser Ile Asn Tyr Arg Thr
                85                  90

<210> SEQ ID NO 228
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 228

Val Ser Asp Val Pro Arg Asp Leu Glu Val Val Ala Ala Thr Pro Thr
1               5                   10                  15

Ser Leu Leu Ile Ser Trp Tyr Leu Ser His Ser Tyr Met Arg Tyr Tyr
            20                  25                  30

```
Arg Ile Thr Tyr Gly Glu Thr Gly Gly Asn Ser Pro Val Gln Glu Phe
            35                  40                  45

Thr Val Pro Val Ile His Tyr Thr Ala Thr Ile Ser Gly Leu Lys Pro
 50                  55                  60

Gly Val Asp Tyr Thr Ile Thr Val Tyr Ala Val Thr Ser Asp Lys Ile
 65                  70                  75                  80

Ser Val Thr Val Ser Gly Pro Ile Ser Ile Asn Tyr Arg Thr
                 85                  90
```

<210> SEQ ID NO 229
<211> LENGTH: 94
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 229

```
Val Ser Asp Val Pro Arg Asp Leu Glu Val Val Ala Ala Thr Pro Thr
 1               5                  10                  15

Ser Leu Leu Ile Ser Trp Lys Ser Val Tyr Val Asp Tyr Arg Tyr Tyr
                 20                  25                  30

Arg Ile Thr Tyr Gly Glu Thr Gly Gly Asn Ser Pro Val Gln Glu Phe
            35                  40                  45

Thr Val Pro His Ser Asn Leu Thr Ala Thr Ile Ser Gly Leu Lys Pro
 50                  55                  60

Gly Val Asp Tyr Thr Ile Thr Val Tyr Ala Val Thr Val Tyr Glu Ser
 65                  70                  75                  80

Tyr Val Ala Asn Asp Ser Pro Ile Ser Ile Asn Tyr Arg Thr
                 85                  90
```

<210> SEQ ID NO 230
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 230

```
Val Ser Asp Val Pro Arg Asp Leu Glu Val Val Ala Ala Thr Pro Thr
 1               5                  10                  15

Ser Leu Leu Ile Ser Trp His Asn Thr Tyr Lys Asp Tyr Arg Tyr Tyr
                 20                  25                  30

Arg Ile Thr Tyr Gly Glu Thr Gly Gly Asn Ser Pro Val Gln Glu Phe
            35                  40                  45

Thr Val Pro His Met Ala Tyr Asn Thr Ala Thr Ile Ser Gly Leu Lys
 50                  55                  60

Pro Gly Val Asp Tyr Thr Ile Thr Val Tyr Ala Val Thr Val Thr Met
 65                  70                  75                  80

Gln Ala Leu Leu Tyr Ser Ile Pro Ile Ser Ile Asn Tyr Arg Thr
                 85                  90                  95
```

<210> SEQ ID NO 231
<211> LENGTH: 102
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic polypeptide"

<400> SEQUENCE: 231

Val Ser Asp Val Pro Arg Asp Leu Glu Val Val Ala Ala Thr Pro Thr
1               5                   10                  15

Ser Leu Leu Ile Ser Trp Gln Val Pro Arg Pro Met Tyr Gln Arg Tyr
            20                  25                  30

Tyr Arg Ile Thr Tyr Gly Glu Thr Gly Gly Asn Ser Pro Val Gln Glu
        35                  40                  45

Phe Thr Val Pro Gly Gly Val Arg Thr Ala Thr Ile Ser Gly Leu Lys
    50                  55                  60

Pro Gly Val Asp Tyr Thr Ile Thr Val Tyr Ala Val Thr Asp Tyr Met
65                  70                  75                  80

His Ser Glu Tyr Arg Gln Tyr Pro Ile Ser Ile Asn Tyr Arg Thr Glu
                85                  90                  95

Ile Asp Lys Pro Cys Gln
            100

<210> SEQ ID NO 232
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Pro Ser Thr Ser Thr Ser Thr
1               5

<210> SEQ ID NO 233
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Glu Ile Asp Lys Pro Ser Gln
1               5

<210> SEQ ID NO 234
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Gly Ser Gly Ser Gly Ser Gly Ser Gly Ser
1               5                   10

<210> SEQ ID NO 235
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 235

Glu Ile Asp Lys Pro Cys Gln
1               5

<210> SEQ ID NO 236
<211> LENGTH: 91
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 236

Gly Val Ser Asp Val Pro Arg Asp Leu Glu Val Val Ala Ala Thr Pro
1               5                   10                  15

Thr Ser Leu Leu Ile Ser Trp Ser Ala Arg Leu Lys Val Ala Arg Tyr
                20                  25                  30

Tyr Arg Ile Thr Tyr Gly Glu Thr Gly Gly Asn Ser Pro Val Gln Glu
            35                  40                  45

Phe Thr Val Pro Lys Asn Val Tyr Thr Ala Thr Ile Ser Gly Leu Lys
    50                  55                  60

Pro Gly Val Asp Tyr Thr Ile Thr Val Tyr Ala Val Thr Arg Phe Arg
65                  70                  75                  80

Asp Tyr Gln Pro Ile Ser Ile Asn Tyr Arg Thr
                85                  90

<210> SEQ ID NO 237
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 237
taatacgact cactataggg acaattacta tttacaatta caatg                45

<210> SEQ ID NO 238
<211> LENGTH: 94
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 238
gggacaatta ctatttacaa ttacaatggt ttctgatgtg ccgcgcgacc tggaagtggt     60
tgctgccacc cccaccagcc tgctgatcag ctgg                                 94

<210> SEQ ID NO 239
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)

<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other

<400> SEQUENCE: 239
agcctgctga tcagctggnn snnsnnsnns nnsnnsnnsc gatattaccg catcact    57

<210> SEQ ID NO 240
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other

<400> SEQUENCE: 240
agcctgctga tcagctggnv hnvhnvhnvh nvhnvhnvhn vhtattaccg catcact    57

<210> SEQ ID NO 241
<211> LENGTH: 57

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(39)
<223> OTHER INFORMATION: a, c, t, g, unknown or other

<400> SEQUENCE: 241
agcctgctga tcagctggnn nnnnnnnnnn nnnnnnnnnc gatattaccg catcact         57

<210> SEQ ID NO 242
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 242
aggcacagtg aactcctgga cagggctatt gcctcctgtt tcgccgtaag tgatgcggta     60
atatcg                                                                66

<210> SEQ ID NO 243
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other

<400> SEQUENCE: 243
caggagttca ctgtgcctnn snnsnnsnns acagctacca tcagcggc                 48

<210> SEQ ID NO 244
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(30)
<223> OTHER INFORMATION: a, c, t, g, unknown or other

<400> SEQUENCE: 244
caggagttca ctgtgcctnn nnnnnnnnnn acagctacca tcagcggc                 48
```

```
<210> SEQ ID NO 245
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 245
agtgacagca tacacagtga tggtataatc aacgccaggt ttaaggccgc tgatggtagc    60
tgt                                                                 63

<210> SEQ ID NO 246
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other

<400> SEQUENCE: 246
actgtgtatg ctgtcactnn snnsnnsnns nnsnnsccaa tttccattaa ttac          54

<210> SEQ ID NO 247
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(36)
<223> OTHER INFORMATION: a, c, t, g, unknown or other

<400> SEQUENCE: 247
actgtgtatg ctgtcactnn nnnnnnnnnn nnnnnnccaa tttccattaa ttac          54

<210> SEQ ID NO 248
<211> LENGTH: 60
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other

<400> SEQUENCE: 248
actgtgtatg ctgtcactnn snnsnnsnns nnsnnsnnsn nsccaatttc cattaattac    60

<210> SEQ ID NO 249
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(42)
<223> OTHER INFORMATION: a, c, t, g, unknown or other

<400> SEQUENCE: 249
actgtgtatg ctgtcactnn nnnnnnnnnn nnnnnnnnnn nnccaatttc cattaattac    60

<210> SEQ ID NO 250
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
```

```
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other

<400> SEQUENCE: 250
actgtgtatg ctgtcactnn snnsnnsnns nnsnnsnnsn nsnnsnnscc aatttccatt    60
aattac                                                              66

<210> SEQ ID NO 251
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(48)
<223> OTHER INFORMATION: a, c, t, g, unknown or other

<400> SEQUENCE: 251
actgtgtatg ctgtcactnn nnnnnnnnnn nnnnnnnnnn nnnnnnnncc aatttccatt    60
aattac                                                              66

<210> SEQ ID NO 252
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
```

```
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other

<400> SEQUENCE: 252
actgtgtatg ctgtcactnn snnsnnsnns nnsnnsnnsn nsnnsnnsnn snnsccaatt      60
tccattaatt ac                                                         72

<210> SEQ ID NO 253
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
```

<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: modified_base
<222> LOCATION: (58)..(59)
<223> OTHER INFORMATION: a, c, t, g, unknown or other

<400> SEQUENCE: 253
actgtgtatg ctgtcactnn snnsnnsnns nnsnnsnnsn nsnnsnnsnn snnsnnsnns    60
ccaatttcca ttaattac                                                 78

<210> SEQ ID NO 254
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 254
ttaaatagcg gatgccttgt cgtcgtcgtc cttgtagtct gtgcggtaat taatggaaat    60
tgg                                                                 63

<210> SEQ ID NO 255
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 255
tttttttttt tttttttttt aaatagcgga tgccttgtcg tcgtcgtcct tgta          54

<210> SEQ ID NO 256
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 256
agcctgctga tcagctggca ggttccgcgt ccgatgtacc aatattaccg catcacttac    60

<210> SEQ ID NO 257
<211> LENGTH: 48

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 257
caggagttca ctgtgcctgg tggtgttcgt acagctacca tcagcggc                    48

<210> SEQ ID NO 258
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 258
actgtgtatg ctgtcactga ctacatgcat tctgaatacc gtcagtaccc aatttccatt       60
aattac                                                                  66

<210> SEQ ID NO 259
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 259
aggcacagtg aactcctgga cagggctatt gcctcctgtt tcgccgtaag tgatgcggta       60
ata                                                                     63

<210> SEQ ID NO 260
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 260
agcctgctga tcagctgg                                                     18

<210> SEQ ID NO 261
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 261
caggagttca ctgtgcct                                                     18

<210> SEQ ID NO 262
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
```

```
      Synthetic primer"

<400> SEQUENCE: 262
actgtgtatg ctgtcact                                                  18

<210> SEQ ID NO 263
<211> LENGTH: 10
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
uagcggaugc                                                           10

<210> SEQ ID NO 264
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 264

His His His His His His
1               5
```